US012760290B2

(12) United States Patent
Segura et al.

(10) Patent No.: US 12,760,290 B2
(45) **Date of Patent: *Oct. 13, 2026**

(54) ORAL CARE COMPOSITION COMPRISING A FRUCTANASE

(71) Applicant: Novozymes A/S, Bagsvaerd (DK)

(72) Inventors: Dorotea Raventos Segura, Rungsted (DK); Lorena González Palmén, Akarp (SE); Jesper Salomon, Holte (DK); Marc Dominique Morant, Frederiksberg (DK); Mette Rose Joergensen, Birkeroed (DK); Thomas Thomasen Durhuus, Copenhagen (DK); Manish Kumar Tiwari, Charlottenlund (DK)

(73) Assignee: Novozymes A/S, Bagsvaerd (DK)

( * ) Notice: Subject to any disclaimer, the term of this patent is extended or adjusted under 35 U.S.C. 154(b) by 542 days.

This patent is subject to a terminal disclaimer.

(21) Appl. No.: 18/042,251

(22) PCT Filed: Aug. 23, 2021

(86) PCT No.: PCT/EP2021/073296

§ 371 (c)(1),
(2) Date: Feb. 20, 2023

(87) PCT Pub. No.: WO2022/043273

PCT Pub. Date: Mar. 3, 2022

(65) Prior Publication Data

US 2023/0332124 A1 Oct. 19, 2023

(30) Foreign Application Priority Data

Aug. 24, 2020 (EP) .................................... 20192387

(51) Int. Cl.

*A61K 8/66* (2006.01)
*A61Q 11/00* (2006.01)
*A61Q 11/02* (2006.01)
*C12N 9/24* (2006.01)

(52) U.S. Cl.

CPC .............. *C12N 9/2402* (2013.01); *A61K 8/66* (2013.01); *A61Q 11/00* (2013.01); *A61Q 11/02* (2013.01); *C12Y 301/21001* (2013.01); *C12Y 302/01007* (2013.01); *C12Y 302/01064* (2013.01); *C12Y 302/01065* (2013.01); *C12Y 302/0108* (2013.01); *C12Y 302/01153* (2013.01); *C12Y 302/01154* (2013.01)

(58) Field of Classification Search

None

See application file for complete search history.

(56) References Cited

U.S. PATENT DOCUMENTS

| | | | |
|---|---|---|---|
| 2002/0006385 | A1 | 1/2002 | Tsuchiya |
| 2020/0016245 | A1 | 1/2020 | Rumbaugh et al. |

FOREIGN PATENT DOCUMENTS

| | | | |
|---|---|---|---|
| CA | 1003351 | A | 1/1977 |
| CN | 110066777 | A | 7/2019 |
| GB | 1420529 | A | 1/1976 |
| GB | 2206585 | A | 1/1989 |
| GB | 2468136 | A | 9/2010 |
| JP | 2006129729 | A | 5/2006 |
| JP | 2019119677 | A2 | 7/2019 |
| WO | 1997038669 | A1 | 10/1997 |
| WO | 1998016191 | A1 | 4/1998 |
| WO | 1998057653 | A1 | 12/1998 |
| WO | 2000017331 | A1 | 3/2000 |
| WO | 2007045450 | A2 | 4/2007 |
| WO | 2009126773 | A1 | 10/2009 |
| WO | 2015109405 | A1 | 7/2015 |
| WO | 2017197280 | A1 | 11/2017 |
| WO | 2017220864 | A1 | 12/2017 |
| WO | 2020099490 | A1 | 5/2020 |
| WO | 2020099491 | A1 | 5/2020 |

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340,).*
Mikayama et al. (Nov. 1993. Proc. Natl.Acad.Sci. USA, vol. 90 : 10056-10060).*
Rudinger et al. (Jun. 1976. Peptide Hormones. Biol. Council. pp. 5-7).*
Blatch et al., Bacteriol, 1993, 3058-3066, 175(10).
Flemming et al., Nature Reviews Microbiology, 2010, 623-633, 8.
Kusuya et al, EBI Accession No. A0A401KQK6, 2019.
Liu et al, Critical reviews in microbiology, 2012, 152-165, 39(2).
Pleszczynska et al, Biotechnol Appl Biochem, 2016, 337-346, 64(3).
Singh et al, International journal of biological_macromolecules, 2016, 312-322, 96.
Wanker et al., 1995, Applied and Environmental Microbiology, 61, 1953-1958.

* cited by examiner

*Primary Examiner* — Jennifer E Graser
(74) *Attorney, Agent, or Firm* — Eric J. Fechter

(57) ABSTRACT

The present invention relates to an oral care composition comprising a fructanase, use of said composition as medicaments, use of said composition in treatment of oral disease, methods of treatment comprising administering said composition to a human or animal subject, methods of removing biofilm comprising contacting the biofilm with said composition, kits of parts comprising said composition, and fructanases.

18 Claims, 1 Drawing Sheet

Specification includes a Sequence Listing.

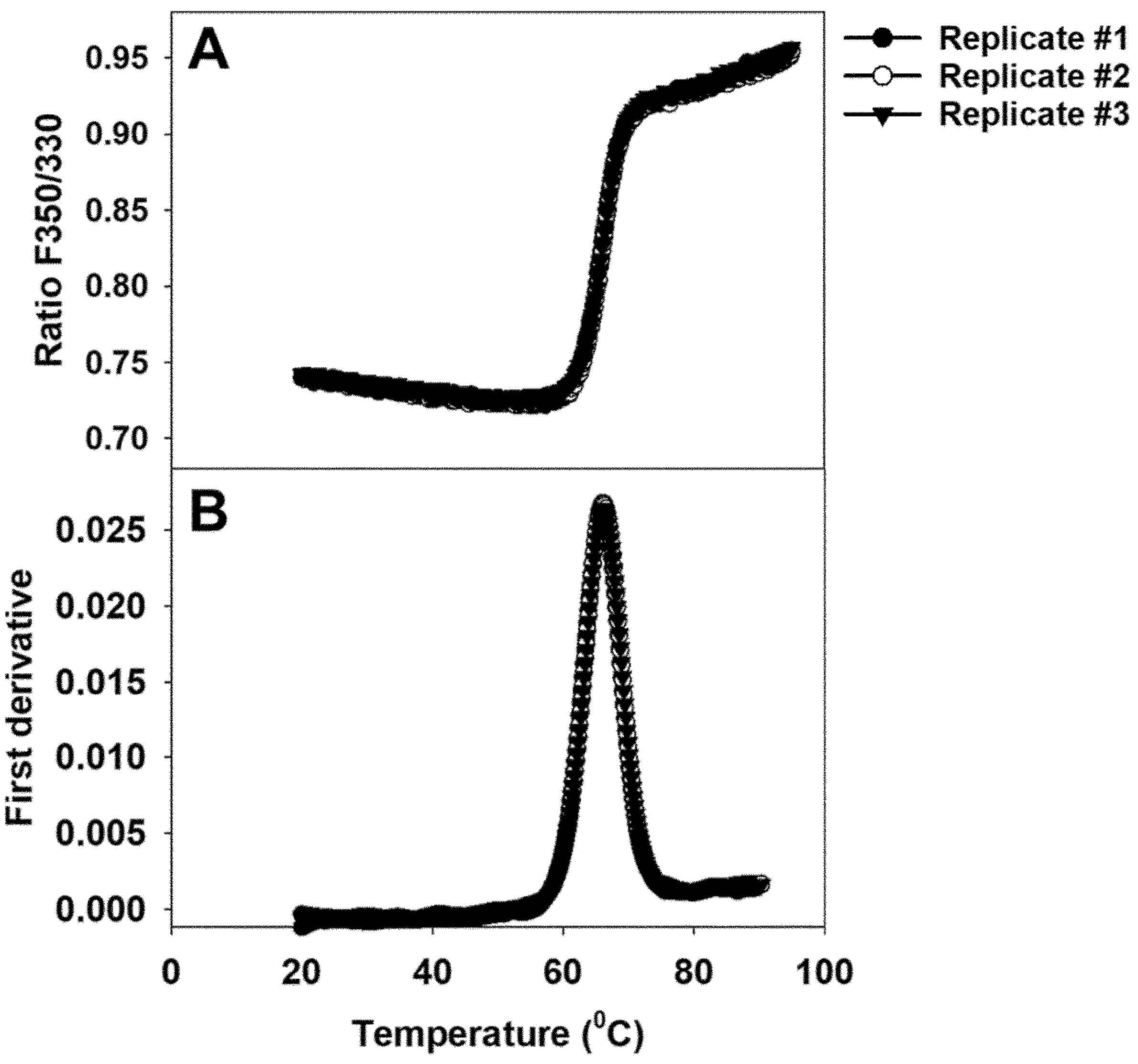
A
B
Ratio F350/330
0.95
0.90
0.85
0.80
0.75
0.70
First derivative
0.025
0.020
0.015
0.010
0.005
0.000
0
20
40
60
80
100
Temperature (⁰C)
Replicate #1
Replicate #2
Replicate #3

SEQUENCE LISTING

```
<160> NUMBER OF SEQ ID NOS: 16

<210> SEQ ID NO 1
<211> LENGTH: 1411
<212> TYPE: PRT
<213> ORGANISM: Penicillium ochrochloron

<400> SEQUENCE: 1

Gln Thr Tyr Asp Glu Leu Tyr Arg Pro Gln Tyr His Phe Thr Pro Pro
1               5                   10                  15

Val Asn Trp Met Asn Asp Pro Asn Gly Leu Leu Tyr His Asn Gly Leu
            20                  25                  30

Tyr His Leu Tyr Tyr Gln Tyr Asn Pro Gly Gly Asn Thr Trp Gly Ala
        35                  40                  45

Met Ser Trp Gly His Ala Thr Ser Thr Asp Leu Thr His Trp Asn His
    50                  55                  60

Gln Pro Ile Ala Leu Leu Ala Arg Gly Tyr Pro Gly Asp Ile Thr Glu
65                  70                  75                  80

Met Phe Phe Ser Gly Ser Ala Val Ala Asp Thr Gln Asn Thr Ser Gly
                85                  90                  95

Phe Gly Thr Ser Gly Lys Val Pro Phe Val Ala Met Tyr Thr Ser Tyr
            100                 105                 110

Tyr Pro Ala Ser Gln Asn Leu Pro Ser Gly Lys Leu Val Asn Gly Gly
        115                 120                 125

Gln Gln Ala Gln Ser Ile Ala Tyr Ser Leu Asp Glu Gly Met Thr Trp
    130                 135                 140

Thr Thr Tyr Asp Ala Ala Asn Pro Val Ile Leu Asn Pro Pro Thr Pro
145                 150                 155                 160

Tyr Thr Asp Gln Trp Arg Asp Phe Arg Asp Pro Phe Leu Phe Trp His
```

-continued

```
                165                 170                 175

Glu Ala Ser Gln Lys Trp Ile Ser Val Val Ser Leu Ala Gln Leu His
            180                 185                 190

Lys Leu Leu Ile Tyr Thr Ser Pro Asn Leu Lys Asp Trp Thr Tyr Ser
        195                 200                 205

Ser Glu Phe Gly Pro Trp Asn Ala Val Gly Gly Val Trp Glu Cys Pro
    210                 215                 220

Ser Leu Phe Pro Leu Ala Val Asp Gly Asp Asp Ala Asn Thr Lys Trp
225                 230                 235                 240

Ile Met Gln Ile Gly Leu Asn Pro Gly Gly Pro Pro Gly Val Thr Gly
                245                 250                 255

Ser Gly Thr Gln Tyr Ile Val Gly Thr Phe Asp Gly Thr Lys Phe Val
            260                 265                 270

Ala Asp Pro Asn Ser Pro Leu Ser Ala His Thr Ser Thr Ser Thr Thr
        275                 280                 285

Thr Ser Ala Ser Val Thr Thr Ser Ala Ser Ile Thr Thr Ser Ala Ser
    290                 295                 300

Ile Thr Pro Thr Thr Thr Lys Ala Thr Ala Thr Ala Thr Ala Thr Gly
305                 310                 315                 320

Asp Ile Ile Phe Gln Asp Phe Glu Gly Ala Gly Asp Phe Ala Ser Arg
                325                 330                 335

Gly Trp Val Ala Thr Gly Gly Leu Leu Gly Ala Ala Pro Ala Lys Gly
            340                 345                 350

Thr Leu Ala Gly Gln Gln Thr Val Thr Gly Tyr Ala Gly Ser Gln Leu
        355                 360                 365

Val Asn Thr Phe Leu Ser Gly Asp Ser Thr Thr Gly Thr Leu Thr Ser
    370                 375                 380

Pro Ala Phe Thr Ile Ser Leu Pro Tyr Val Asn Phe Leu Ile Gly Gly
385                 390                 395                 400

Gly Asn Ala Pro Gly Thr Glu Cys Ile Asn Leu Lys Val Gln Gly Gln
                405                 410                 415

Ala Val Arg Thr Ala Thr Gly Ala Asn Val Glu Gln Leu Ala Pro Thr
            420                 425                 430

Thr Trp Asn Val Thr Asp Leu Met Gly Gln Thr Ala Val Leu Glu Ile
        435                 440                 445

Val Asp Gln Gln Thr Gly Gly Trp Gly His Ile Leu Ile Asp Gln Ile
    450                 455                 460

Thr Phe Thr Ser Ser Thr Ser Thr Asn Asn Leu His Lys Arg Ser Val
465                 470                 475                 480

Ser Ser Val Thr Trp Asp Phe Asn Gly Thr Ser Thr Phe Ala Asp Tyr
                485                 490                 495

Gly Trp Thr Pro Ser Gly Asp Phe Val Gly Lys Gly Pro Ala Gln Gly
            500                 505                 510

Thr Leu Ala Gly Gln Gln Val Val Thr Gly Asn Met Gly Asn Phe Val
        515                 520                 525

Asn Thr Phe Leu Ser Gly Asp Gly Thr Thr Gly Thr Leu Thr Ser Pro
    530                 535                 540

Ala Phe Thr Ile Thr Gln Lys Lys Ile Asn Phe Leu Ile Gly Gly Gly
545                 550                 555                 560

Asn Ser Pro Gly Met Glu Cys Ile Asn Leu Lys Ile Gln Gly Gln Val
                565                 570                 575

Val Arg Thr Ala Thr Gly Ala Asn Ala Glu Gln Leu Val Pro Thr Thr
            580                 585                 590
```

```
Trp Asp Val Thr Asp Leu Ile Gly Gln Ser Ala Val Ile Glu Ile Val
        595                 600                 605

Asp Leu Ser Thr Thr Gly Trp Gly His Ile Leu Ile Asp Glu Ile Ser
    610                 615                 620

Phe Ser Asn Ile Ser Ile Val Pro Tyr Gly Pro Asn Trp Leu Asp Tyr
625                 630                 635                 640

Gly Pro Asp Phe Tyr Ala Ala Thr Thr Phe Asn Gly Leu Ser Ser Thr
                645                 650                 655

Asn Arg Ile Asp Ile Ala Trp Met Asn Asn Trp Gln Tyr Ala Ser Ala
            660                 665                 670

Ile Pro Thr Ser Pro Trp Arg Ser Met Leu Ser Val Ala Arg Lys Leu
        675                 680                 685

Ser Leu Lys Thr Ile Asp Asp Arg Pro Arg Leu Ile Gln Gln Pro Glu
    690                 695                 700

Ala Asn Trp Thr Ser Leu Gln Thr Thr Thr Tyr Ser Thr Ser Phe Asp
705                 710                 715                 720

Thr Val Ala Glu Gly Asn Gln Leu Val Gln Leu Ser Gly Lys Leu Leu
                725                 730                 735

Asp Ile Thr Val Ala Phe Ser Asp Arg Val Ala Ala Ser Ser Ser Ser
            740                 745                 750

Gln Phe Gly Ile Ile Leu Arg Ala Thr Ser Asp Leu Ala Gln Gln Thr
        755                 760                 765

Arg Ile Gly Tyr Asp Phe Ser Thr Lys Arg Leu Phe Val Asp Arg Thr
    770                 775                 780

Lys Ser Gly Asn Val Gly Phe Asp Gly Thr Phe Pro Ser Thr Tyr Phe
785                 790                 795                 800

Ala Pro Leu Ala Pro Ser Gly Asp Gly Arg Val Thr Met Arg Ile Leu
                805                 810                 815

Leu Asp Arg Ser Ser Val Glu Val Phe Gly Gly Gln Gly Glu Val Thr
            820                 825                 830

Ile Ser Ala Gln Ile Phe Pro Gln Asp Asn Gly Val Asp Val Arg Leu
        835                 840                 845

Phe Ser Arg Gly Gly Ser Thr Asn Ala Ile Thr Ile Asp Ala Ile Val
    850                 855                 860

Leu Asp Ser Val Tyr Asp Ser Ser Thr Pro Ser Ala Ser Leu Ser Thr
865                 870                 875                 880

Ser Ser Thr Ser Ile Gly Thr Val Thr Thr Thr Phe Ser Asn Thr Val
                885                 890                 895

Thr Thr Ser Val Gly Asn Thr Leu Thr Thr Ser Thr Arg Thr Val Thr
            900                 905                 910

Ser Ala Ser Pro Thr Ser Thr Ala Pro Tyr Asp Phe Arg Pro Val Phe
        915                 920                 925

His Phe Val Pro Glu Glu Asn Trp Met Asn Glu Pro Asn Gly Leu Ile
    930                 935                 940

Lys Ile Asp Ser Thr Trp His Leu Phe Phe Gln His Asn Pro Thr Gly
945                 950                 955                 960

Asn Phe Trp Gly Asn Leu Ser Trp Gly His Ala Thr Ser Ile Asp Leu
                965                 970                 975

Val Ser Trp Asp Tyr Lys Pro Val Ala Ile Ser Ser Ala Asp Gly Ile
            980                 985                 990

Gln Ala Phe Thr Gly Thr Ser Tyr  Phe Asp Ala Met Asn  Leu Ser Gly
        995                 1000                1005
```

```
Leu Gly  Thr Ser Ser Asn Gln  Pro Tyr Leu Ala Phe  Tyr Thr Gly
    1010                 1015                 1020

Tyr Ala  Pro Ser Ser Gly Ile  Gln Asp Gln Arg Leu  Ala Tyr Ser
    1025                 1030                 1035

Leu Asp  Gln Gly Ala Thr Trp  Met Lys Tyr Gln Gly  Asn Pro Ile
    1040                 1045                 1050

Ile Ser  Gln Ser Gln Glu Ala  Pro His Asp Ile Thr  Gln Gly Leu
    1055                 1060                 1065

Glu Ile  Arg Asp Pro Lys Val  Phe Tyr His Ser Pro  Thr Ser Arg
    1070                 1075                 1080

Trp Val  Met Ile Leu Ala His  Gly Gly Gln Asn Lys  Leu Thr Phe
    1085                 1090                 1095

Trp Thr  Ser Thr Asp Ala Lys  Asn Trp Thr Trp Arg  Ser Asn Phe
    1100                 1105                 1110

Ala Ala  Ser Asn Ile Leu Gly  Phe Pro Ser Gly Val  Asn Gly Trp
    1115                 1120                 1125

Glu Val  Pro Asp Phe Phe Glu  Leu Arg Ile Gln Gly  Thr Thr Gln
    1130                 1135                 1140

Tyr Lys  Trp Val Leu Ile Val  Thr Pro Ala Ala Gly  Ser Pro Ala
    1145                 1150                 1155

Gly Gly  Asn Gly Val Phe Ala  Leu Thr Gly Ser Phe  Asp Gly Glu
    1160                 1165                 1170

Val Phe  Thr Ala Asp Ala Val  Asp Pro Thr Thr Leu  Trp Leu Asp
    1175                 1180                 1185

Tyr Gly  Arg Asp Trp Asp Gly  Val Met Ser Trp Glu  Asn Val Pro
    1190                 1195                 1200

Ala Ser  Asp Gly Arg Arg Val  Leu Ala Ala Val Met  Asn Ser Tyr
    1205                 1210                 1215

Gly Gly  Asn Pro Pro Thr Asn  Thr Trp Lys Gly Met  Leu Ser Phe
    1220                 1225                 1230

Pro Arg  Thr Leu Glu Leu Lys  Gln Leu Asn Gly Lys  Leu Arg Phe
    1235                 1240                 1245

Leu Gln  Leu Pro Val Ser Glu  Leu Asp Ala Val Gly  Ala Ser Val
    1250                 1255                 1260

Ala Thr  Ile Thr Asn Gln Thr  Leu Ala Pro Gly Gln  Thr Leu Leu
    1265                 1270                 1275

Ser Asn  Ile His Ser Arg Ser  Leu Asp Ile Leu Ile  Thr Phe Val
    1280                 1285                 1290

Pro Ala  Gln Gly Ser Thr Leu  Ser Leu Ser Val Arg  Lys Gly Gly
    1295                 1300                 1305

Ser Gln  Gln Thr Val Ile Glu  Tyr Val Gln Ser Asn  Asn Gln Leu
    1310                 1315                 1320

Ser Val  Asp Arg Asn Glu Ser  Gly Asn Thr Ser Tyr  Asp Pro Ala
    1325                 1330                 1335

Ala Gly  Gly Val His Ser Ala  Ala Leu His Ala Asp  Glu Asn Gly
    1340                 1345                 1350

Lys Val  Gln Leu Arg Val Leu  Val Asp Glu Cys Ser  Ile Glu Val
    1355                 1360                 1365

Tyr Gly  Gly Gln Gly Glu Ala  Val Ile Ser Asp Leu  Ile Phe Pro
    1370                 1375                 1380

Asp Phe  Ser Ser Asp Gly Leu  Ala Leu Ser Thr Ser  Gln Gly Asn
    1385                 1390                 1395

Val Val  Leu Glu Ser Val Asp  Val Arg Ser Ile Leu  Leu
```

1400 1405 1410

<210> SEQ ID NO 2
<211> LENGTH: 653
<212> TYPE: PRT
<213> ORGANISM: Bacillus licheniformis

<400> SEQUENCE: 2

Ala Asp Pro Asp Tyr Tyr Asn Glu Asp His Arg Pro Lys Tyr His Phe
1 5 10 15

Thr Pro Glu Ala Asn Trp Met Asn Asp Pro Asn Gly Met Val Tyr Tyr
20 25 30

Ala Gly Glu Tyr His Leu Phe Tyr Gln Tyr His Pro Tyr Gly Leu Arg
35 40 45

Trp Gly Pro Met His Trp Gly His Ala Val Ser Lys Asp Leu Val Lys
50 55 60

Trp Glu His Leu Pro Val Ala Leu Tyr Pro Asp Glu Lys Gly Thr Ile
65 70 75 80

Phe Ser Gly Ser Ala Val Val Asp Arg His Asn Thr Thr Gly Phe Gln
85 90 95

Thr Gly Thr Glu Lys Pro Leu Val Ala Ile Tyr Thr Gln Asp Arg Asp
100 105 110

Gly Glu Gln Val Gln Ser Ile Ala Tyr Ser Asn Asp Lys Gly Arg Thr
115 120 125

Trp Thr Lys Tyr Ser Gly Asn Pro Val Ile Pro Asn Pro Gly Lys Arg
130 135 140

Asp Phe Arg Asp Pro Lys Val Val Trp His Lys Gln Thr Asn Lys Trp
145 150 155 160

Val Met Leu Leu Ala Gly Gly Asp Arg Ile Leu Ile Tyr Thr Ser Pro
165 170 175

Asp Leu Lys Gln Trp Thr Tyr Ala Ser Glu Phe Gly Lys Gly Glu Gly
180 185 190

Ser His Gly Gly Val Trp Glu Cys Pro Asp Leu Phe Glu Leu Pro Val
195 200 205

Glu Gly Arg Pro Asn Glu Thr Lys Trp Val Met Gln Val Ser Val Gly
210 215 220

Asp Gly Ala Val Ser Gly Gly Ser Gly Met Gln Tyr Phe Val Gly Ser
225 230 235 240

Phe Asp Gly Thr Thr Phe Lys Asn Glu Asn Pro Pro Asn Arg Val Leu
245 250 255

Trp Thr Asp Tyr Gly Lys Asp Phe Tyr Ala Ala Val Ser Trp Ser Asp
260 265 270

Ile Pro Gln Ser Asp Gly Arg Arg Leu Trp Leu Gly Trp Met Ser Asn
275 280 285

Trp Gln Tyr Ala Asn Asp Val Pro Thr Ser Pro Trp Arg Ser Ala Met
290 295 300

Ser Ile Pro Arg Glu Leu Lys Leu Lys Ala Phe Ser Glu Gly Phe Arg
305 310 315 320

Ile Val Gln Ala Pro Val Ala Glu Leu Lys Ser Ile Arg Gly Ala Ser
325 330 335

Gln Arg Trp Lys Asp Lys Ile Ile Ser Pro Arg Asn Arg Asn Phe Leu
340 345 350

Lys Ala Leu Ser Gly Asp Ala Tyr Glu Ile Asn Ala Glu Phe Gln Val
355 360 365

```
Asn Thr Gly Thr Ala Ala Glu Phe Gly Phe Lys Val Arg Thr Gly Glu
    370                 375                 380

Asn Gln Tyr Thr Lys Ile Gly Tyr Ser Lys Asn Ser Ala Ser Leu Phe
385                 390                 395                 400

Val Asp Arg Ser Gln Ser Gly Asn Val Ser Phe His Pro Asn Phe Asn
                405                 410                 415

Thr Gly Lys His Ala Ala Pro Leu Gln Pro Val Gly Gly Lys Val Lys
            420                 425                 430

Met Arg Ile Tyr Val Asp Arg Ser Ser Val Glu Val Phe Gly Asn Asp
        435                 440                 445

Gly Arg Gln Val Ile Thr Asp Ile Ile Leu Pro Asp Arg Ser Ser Lys
    450                 455                 460

Gly Val Glu Ala Tyr Ala Ser Asn Gly Phe Val Lys Leu Asn Ser Met
465                 470                 475                 480

Thr Val His Pro Leu Lys Lys Val Trp Gly Thr Ser Pro Phe Gln Ser
                485                 490                 495

Asn Leu Thr Gly Trp Thr Thr Val Asn Gly Val Trp Ala Asp Thr Ile
            500                 505                 510

Asp Gly Lys Gln Gly Arg Ser Asp Gly Asp Ser Phe Ile Leu Ser Ser
        515                 520                 525

Ala Lys Gly Thr Asp Phe Thr Tyr Glu Ala Asp Val Thr Val Lys Asp
    530                 535                 540

Gly Asn Gly Arg Gly Ala Gly Ala Leu Val Phe Arg Ala Asp Lys Asp
545                 550                 555                 560

Val Gln Asn Gly Tyr Leu Ala Asn Val Asp Ala Lys His Asp Val Val
                565                 570                 575

Lys Phe Phe Lys Phe Glu Asn Gly Ser Ala Ser Val Ile Ala Glu His
            580                 585                 590

Arg Thr Pro Leu Glu Ala Gly Arg Lys Tyr His Leu Lys Ala Val Ala
        595                 600                 605

Arg Gly Ser Asn Phe Tyr Ile Tyr Leu Asp Asp Arg Leu Val Ile Ser
    610                 615                 620

Ala Arg Asp Ser Thr Phe Thr Glu Gly Val Phe Gly Leu Asn Ala Trp
625                 630                 635                 640

Asp Ala Thr Ala Val Phe Gln His Val Tyr Ala Asp Arg
                645                 650


<210> SEQ ID NO 3
<211> LENGTH: 653
<212> TYPE: PRT
<213> ORGANISM: Bacillus licheniformis

<400> SEQUENCE: 3

Ala Asp Pro Asp Tyr Tyr Asn Glu Asp His Arg Pro Lys Tyr His Phe
1               5                   10                  15

Thr Pro Glu Ala Asn Trp Met Asn Asp Pro Asn Gly Met Val Tyr Tyr
            20                  25                  30

Ala Gly Glu Tyr His Leu Phe Tyr Gln Tyr His Pro Tyr Gly Leu Arg
        35                  40                  45

Trp Gly Pro Met His Trp Gly His Ala Val Ser Lys Asp Leu Val Lys
    50                  55                  60

Trp Glu His Leu Pro Val Ala Leu Tyr Pro Asp Glu Lys Gly Thr Ile
65                  70                  75                  80

Phe Ser Gly Ser Ala Val Val Asp Arg His Asn Thr Thr Gly Phe Gln
                85                  90                  95
```

```
Thr Gly Ala Glu Lys Pro Leu Val Ala Ile Tyr Thr Gln Asp Arg Asp
            100                 105                 110

Gly Glu Gln Val Gln Ser Ile Ala Tyr Ser Asn Asp Lys Gly Arg Thr
        115                 120                 125

Trp Thr Lys Tyr Ser Gly Asn Pro Val Ile Pro Asn Pro Gly Lys Lys
    130                 135                 140

Asp Phe Arg Asp Pro Lys Val Ile Trp His Glu Gln Thr Lys Lys Trp
145                 150                 155                 160

Val Met Met Leu Ala Gly Gly Asp Arg Ile Leu Ile Tyr Thr Ser Pro
                165                 170                 175

Asp Leu Lys Gln Trp Thr Tyr Ala Ser Glu Phe Gly Glu Gly Glu Gly
            180                 185                 190

Ser His Gly Gly Val Trp Glu Cys Pro Asp Leu Phe Glu Leu Pro Val
        195                 200                 205

Glu Gly Arg Pro Asn Glu Thr Lys Trp Val Met Gln Val Ser Val Gly
    210                 215                 220

Asp Gly Ala Val Ser Gly Gly Ser Gly Met Gln Tyr Phe Val Gly Ser
225                 230                 235                 240

Phe Asp Gly Thr Thr Phe Lys Asn Glu Asn Pro Pro Asn Arg Val Leu
                245                 250                 255

Trp Thr Asp Tyr Gly Lys Asp Phe Tyr Ala Ala Val Ser Trp Ser Asp
            260                 265                 270

Ile Pro Gln Ser Asp Gly Arg Arg Leu Trp Leu Gly Trp Met Ser Asn
        275                 280                 285

Trp Gln Tyr Ala Asn Asp Val Pro Thr Ser Pro Trp Arg Ser Ala Met
    290                 295                 300

Ser Ile Pro Arg Glu Leu Lys Leu Lys Ala Phe Ser Glu Gly Leu Arg
305                 310                 315                 320

Ile Val Gln Thr Pro Val Ala Glu Leu Gln Ser Ile Arg Gly Ala Ser
                325                 330                 335

Gln Thr Trp Lys Asn Lys Ile Ile Ser Pro Arg Asn Gly Asn Phe Leu
            340                 345                 350

Lys Ala Leu Ser Gly Asp Ala Tyr Glu Ile Asn Ala Glu Phe Gln Val
        355                 360                 365

Asn Thr Gly Ala Ala Ala Glu Phe Gly Phe Lys Val Arg Thr Gly Glu
    370                 375                 380

Asn Glu Tyr Thr Lys Ile Gly Tyr Ser Lys Asn Ser Ala Ser Leu Phe
385                 390                 395                 400

Val Asp Arg Ser Gln Ser Gly Asn Val Ser Phe Asn Pro Asn Phe Asn
                405                 410                 415

Thr Gly Lys His Ala Ala Pro Leu Gln Pro Val Gly Gly Lys Val Lys
            420                 425                 430

Met Arg Ile Tyr Val Asp Arg Ser Ser Val Glu Val Phe Gly Asn Asp
        435                 440                 445

Gly Arg Gln Val Ile Thr Asp Ile Ile Leu Pro Asp Arg Ser Ser Lys
    450                 455                 460

Gly Leu Glu Val Tyr Ala Ser Asn Gly Phe Val Lys Leu Asn Ser Met
465                 470                 475                 480

Thr Val His Pro Leu Lys Lys Val Trp Gly Ala Ser Pro Phe Gln Ser
                485                 490                 495

Asn Leu Thr Gly Trp Thr Thr Val Asn Gly Val Trp Ala Asp Thr Ile
            500                 505                 510
```

```
Ala Gly Lys Gln Gly Arg Ser Asp Gly Asp Ser Phe Ile Leu Ser Ser
        515                 520                 525

Ala Lys Gly Thr Asp Phe Thr Tyr Glu Ala Asp Val Thr Ile Lys Asp
    530                 535                 540

Gly Asn Gly Arg Gly Ala Gly Ala Leu Val Phe Arg Ala Asp Lys Asp
545                 550                 555                 560

Val Lys Asn Gly Tyr Leu Ala Asn Val Asp Ala Lys His Asp Val Val
                565                 570                 575

Lys Phe Phe Lys Phe Glu Asn Gly Ser Ala Ser Val Ile Ala Glu His
            580                 585                 590

Arg Thr Pro Ile Glu Ala Gly Arg Lys Tyr His Leu Lys Thr Val Ala
        595                 600                 605

Arg Gly Ala Asn Phe Thr Ile Tyr Leu Asp Asp Gln Leu Val Ile Ser
    610                 615                 620

Ala Arg Asp Ser Thr Phe Ala Asp Gly Ala Phe Gly Leu Asn Ala Trp
625                 630                 635                 640

Asp Ala Thr Ala Val Phe Gln Gln Val Tyr Ala Lys Arg
                645                 650


<210> SEQ ID NO 4
<211> LENGTH: 631
<212> TYPE: PRT
<213> ORGANISM: Arthrobacter sp. Leaf337

<400> SEQUENCE: 4

Gly Gln Gln Pro Ala Pro Ala Gly Pro Ala Ala Gly Ala Leu Ala Asp
1               5                   10                  15

Val Ala Asp Ala Gln Ala Glu Ala Lys Lys Asp Ser Gly Arg Tyr Gly
            20                  25                  30

Ser Phe Trp Leu Ala Gly Gly Asp Arg Ser Leu Glu Asn Leu Ala Arg
        35                  40                  45

Pro Leu Arg Thr Asp Gly Val Ser Asp Leu Arg Ala Ile Asp Cys Ala
    50                  55                  60

Asp Gly Trp Val Ala Ala Ala Arg Val Gly Gln Ala Val Thr Val Arg
65                  70                  75                  80

Ser Ser Glu Gln Asp Ser Ala Val Leu Ala Lys Ala Ala Arg Ala Gly
                85                  90                  95

Ser Ala Asp Ile Ser Arg Pro Asp Cys Val Thr Pro Glu Ala Val Asp
            100                 105                 110

Ala Met Leu Ala Asp Leu Gly Ala Gly Pro Glu Gln Pro Ala Pro Ala
        115                 120                 125

Glu Ser Ala Phe Ala Arg Pro Glu Gly Ala Ser Gly Tyr Arg Pro Gly
    130                 135                 140

Tyr His Ile Thr Pro Arg Glu Asn Trp Met Asn Asp Pro Gln Arg Pro
145                 150                 155                 160

Phe Leu Leu Asp Gly Leu Trp His Tyr Tyr Tyr Leu Tyr Asn Ala Gly
                165                 170                 175

Tyr Pro Glu Glu Asn Gly Thr Glu Trp Tyr His Leu Thr Ser Thr Asp
            180                 185                 190

Leu Val His Trp Lys Asp Glu Gly Val Ala Ile Glu Lys Tyr Lys Asn
        195                 200                 205

Gly Leu Gly Asp Ile Glu Thr Gly Ser Ala Val Val Asp Tyr Glu Asn
    210                 215                 220

Ser Ala Gly Phe Gly Lys Gly Ala Val Val Ala Val Met Thr Gln Gln
225                 230                 235                 240
```

Asp Glu Gly Ile Gln Arg Gln Ser Leu Phe Tyr Ser Thr Asp Lys Gly
245 250 255

Tyr Ser Phe Lys Pro Tyr Asp Gly Asn Pro Val Met Asp Asn Pro Gly
260 265 270

Glu Gln His Trp Arg Asp Pro Lys Ile Ile Arg Asp Glu Ala Asn Asp
275 280 285

Gln Trp Val Met Ala Leu Ala Glu Gly Gly Lys Ile Gly Leu Tyr Ala
290 295 300

Ser Ala Asn Leu Lys Glu Trp Asn Tyr Leu Ser Gly Phe Glu Arg Lys
305 310 315 320

Gly Leu Gly Ile Leu Glu Cys Pro Glu Leu Phe Gln Leu Asp Val Asp
325 330 335

Gly Asp Pro Ala Lys Arg Thr Trp Val Leu Ala Ala Ser Ala Asn Gly
340 345 350

Ala Glu Glu Gly Arg Ala Thr Gly Val Ala Tyr Trp Thr Gly Asn Trp
355 360 365

Asp Gly Thr Arg Phe Glu Pro Ser Asp Asp Lys His Gln Trp Leu Asp
370 375 380

Asp Gly Ser Asp Phe Tyr Ala Ala Val Thr Trp Asp Asp Pro Arg Leu
385 390 395 400

Thr Glu Gly Gln Arg Met Gly Ser Arg His Ser Ile Ala Trp Leu Asn
405 410 415

Asn Trp Ala Tyr Ala Arg Lys Leu Pro Thr Gln Asp Trp His Gly Gly
420 425 430

Ala Asp Thr Val Val Arg Asp Ile Arg Leu Lys Thr Val Ser Gly Lys
435 440 445

Pro Thr Leu Val Ser Thr Pro Thr Asn Ala Leu Lys Ser Leu Gln Gly
450 455 460

Glu Thr Val Thr Ala Gly Glu Arg Lys Leu Thr Pro Asp Gly Ala Ala
465 470 475 480

Ser Leu Pro Glu Gln Gly Leu Pro Asp Gln Gly Leu Pro Ala Pro Ala
485 490 495

Gly Gly Ala Tyr Arg Leu Asp Leu Thr Leu Glu Arg Ala Ala Gly Asp
500 505 510

Asp Gly Ser Glu Ala Arg Val Glu Leu Leu Ala Glu Asn Gly Val Phe
515 520 525

Ala Thr Val Gly Tyr Asp Phe Glu Ser Glu Ala Ala Phe Val Ser Arg
530 535 540

Asp Gly Ala Ala Lys Glu Thr Ala Gly Leu Ala Pro Asp Tyr Gly Ala
545 550 555 560

Val Arg Arg Thr Ala Ser Ala Pro Arg Asp Gly Lys Val Glu Leu Thr
565 570 575

Val Tyr Val Asp His Ser Thr Val Glu Val Phe Val Asn Gly Gly Glu
580 585 590

Arg Thr Leu Thr Ser Leu Val Phe Pro Ser Gly Ala Pro Thr Gly Leu
595 600 605

Lys Ala Leu Thr Lys Asp Gly Thr Leu Thr Leu Lys Ser Phe Ser Tyr
610 615 620

Thr Pro Met Ala Ala Ala Ser
625 630

<210> SEQ ID NO 5
<211> LENGTH: 653

<212> TYPE: PRT
<213> ORGANISM: Bacillus subtilis

<400> SEQUENCE: 5

```
Ala Asp Ser Ser Tyr Tyr Asp Glu Asp Tyr Arg Pro Gln Tyr His Phe
1               5                   10                  15

Thr Pro Glu Ala Asn Trp Met Asn Asp Pro Asn Gly Met Val Tyr Tyr
            20                  25                  30

Ala Gly Glu Tyr His Leu Phe Tyr Gln Tyr His Pro Tyr Gly Leu Gln
        35                  40                  45

Trp Gly Pro Met His Trp Gly His Ala Val Ser Lys Asp Leu Val Thr
    50                  55                  60

Trp Glu His Leu Pro Val Ala Leu Tyr Pro Asp Glu Lys Gly Thr Ile
65                  70                  75                  80

Phe Ser Gly Ser Ala Val Val Asp Lys Asn Asn Thr Ser Gly Phe Gln
                85                  90                  95

Thr Gly Lys Glu Lys Pro Leu Val Ala Ile Tyr Thr Gln Asp Arg Glu
            100                 105                 110

Gly His Gln Val Gln Ser Ile Ala Tyr Ser Asn Asp Lys Gly Arg Thr
        115                 120                 125

Trp Thr Lys Tyr Ala Gly Asn Pro Val Ile Pro Asn Pro Gly Lys Lys
    130                 135                 140

Asp Phe Arg Asp Pro Lys Val Phe Trp Tyr Glu Lys Glu Lys Lys Trp
145                 150                 155                 160

Val Met Val Leu Ala Ala Gly Asp Arg Ile Leu Ile Tyr Thr Ser Lys
                165                 170                 175

Asn Leu Lys Gln Trp Arg Tyr Ala Ser Glu Phe Gly Gln Asp Gln Gly
            180                 185                 190

Ser His Gly Gly Val Trp Glu Cys Pro Asp Leu Phe Glu Leu Pro Val
        195                 200                 205

Asp Gly Asn Pro Asn Arg Lys Lys Trp Val Met Gln Val Ser Val Gly
    210                 215                 220

Asn Gly Ala Val Ser Gly Gly Ser Gly Met Gln Tyr Phe Val Gly Asp
225                 230                 235                 240

Phe Asp Gly Thr His Phe Lys Asn Glu Asn Pro Ser Asn Lys Val Leu
                245                 250                 255

Trp Thr Asp Tyr Gly Arg Asp Phe Tyr Ala Ala Val Ser Trp Ser Asp
            260                 265                 270

Ile Pro Ser Thr Asp Ser Arg Arg Leu Trp Leu Gly Trp Met Ser Asn
        275                 280                 285

Trp Gln Tyr Ala Asn Asp Val Pro Thr Ser Pro Trp Arg Ser Ala Thr
    290                 295                 300

Ser Ile Pro Arg Glu Leu Lys Leu Lys Ala Phe Thr Glu Gly Val Arg
305                 310                 315                 320

Val Val Gln Thr Pro Val Lys Glu Leu Glu Thr Ile Arg Gly Thr Ser
                325                 330                 335

Lys Lys Trp Lys Asn Leu Thr Ile Ser Pro Ala Ser His Asn Val Leu
            340                 345                 350

Ala Gly Gln Ser Gly Asp Ala Tyr Glu Ile Asn Ala Glu Phe Lys Val
        355                 360                 365

Ser Pro Gly Ser Ala Ala Glu Phe Gly Phe Lys Val Arg Thr Gly Glu
    370                 375                 380

Asn Gln Ser Thr Lys Val Gly Tyr Asp Arg Arg Asn Ala Lys Leu Phe
385                 390                 395                 400
```

```
Val Asp Arg Ser Glu Ser Gly Asn Asp Thr Phe Ser Pro Ala Phe Asn
                405                 410                 415

Thr Gly Lys Glu Thr Ala Pro Leu Lys Pro Val Asn Gly Lys Val Lys
            420                 425                 430

Met Arg Ile Phe Val Asp Arg Ser Ser Val Glu Val Phe Gly Asn Asp
        435                 440                 445

Gly Lys Gln Val Ile Thr Asp Ile Ile Leu Pro Asp Arg Ser Ser Lys
    450                 455                 460

Gly Leu Glu Leu Tyr Ala Ala Asn Gly Gly Val Lys Val Lys Ser Leu
465                 470                 475                 480

Thr Ile His Pro Leu Lys Lys Val Trp Gly Thr Ser Pro Phe Met Ser
                485                 490                 495

Asn Leu Thr Gly Trp Thr Thr Val Asn Gly Thr Trp Ala Asp Thr Ile
            500                 505                 510

Glu Gly Lys Gln Gly Arg Ser Asp Gly Asp Ser Phe Ile Leu Ser Ser
        515                 520                 525

Ala Ser Gly Ser Asp Phe Thr Tyr Glu Ser Asp Ile Thr Ile Lys Asp
    530                 535                 540

Gly Asn Gly Arg Gly Ala Gly Ala Leu Met Phe Arg Ser Asp Lys Asp
545                 550                 555                 560

Ala Lys Asn Gly Tyr Leu Ala Asn Val Asp Ala Lys His Asp Leu Val
                565                 570                 575

Lys Phe Phe Lys Phe Glu Asn Gly Ala Ala Ser Val Ile Ala Glu Tyr
            580                 585                 590

Lys Thr Pro Ile Asp Val Asn Lys Lys Tyr His Leu Lys Thr Glu Ala
        595                 600                 605

Glu Gly Asp Arg Phe Lys Ile Tyr Leu Asp Asp Arg Leu Val Ile Asp
    610                 615                 620

Ala Asn Asp Ser Ala Phe Ser Glu Gly Gln Phe Gly Leu Asn Val Trp
625                 630                 635                 640

Asp Ala Thr Ala Val Phe Gln Asn Val Lys Lys Glu Ser
                645                 650


<210> SEQ ID NO 6
<211> LENGTH: 506
<212> TYPE: PRT
<213> ORGANISM: Flavobacterium banpakuense

<400> SEQUENCE: 6

Gln Asn Thr Ala Val Ser Val Ser Thr Ser Ser Glu Glu Gln Met Tyr
1               5                   10                  15

Arg Pro Asn Phe His Phe Thr Pro Lys Lys Gly Trp Met Asn Asp Pro
            20                  25                  30

Asn Gly Met Phe Tyr Ala Asn Gly Leu Tyr His Leu Ser Tyr Gln His
        35                  40                  45

Tyr Pro Asp Gly Asn Lys Trp Gly Pro Met His Trp Gly His Ala Val
    50                  55                  60

Ser Lys Asp Leu Ile Lys Trp Glu Glu Gln Pro Ile Ala Ile Tyr Pro
65                  70                  75                  80

Asp Asn Asp Lys Tyr Ile Phe Ser Gly Ser Ser Val Val Asp Thr Asn
                85                  90                  95

Asn Thr Ser Gly Leu Gly Thr Gly Lys Thr Ala Pro Ile Val Ala Ile
            100                 105                 110

Tyr Thr Leu His Asn Met Thr Lys Glu Lys Glu Asn Lys Ile Asp Val
```

```
        115                 120                 125

Glu Gln Gln Asp Ile Ala Tyr Ser Asn Asp Asn Gly Phe Thr Trp Gln
    130                 135                 140

Lys Phe Glu Glu Gly Asn Pro Val Ile Lys Asn Pro Gly Ile Arg Asp
145                 150                 155                 160

Phe Arg Asp Pro Lys Met Thr Trp Asn Glu Thr His Lys Gln Trp Ile
                165                 170                 175

Leu Val Leu Ala Ala Gln Asp Arg Ala Gln Phe Tyr Lys Ser Lys Asp
            180                 185                 190

Leu Lys Asn Trp Glu Tyr Leu Ser Asp Phe Gly Lys Asn Ile Gly Ala
        195                 200                 205

His Gly Gly Val Trp Glu Cys Pro Asp Phe Phe Glu Ile Lys Val Lys
    210                 215                 220

Gly Thr Asn Glu Thr Lys Trp Val Leu Ile Gln Ser Leu Asn Pro Gly
225                 230                 235                 240

Gly Ala Asn Gly Gly Ser Gly Thr Gln Tyr Phe Ile Gly Asp Phe Asp
                245                 250                 255

Gly Lys Thr Phe Thr Leu Asp Ser Asn Phe Ala Lys Arg Val Glu Asn
            260                 265                 270

Glu Lys Ala Val Trp Ile Asp Tyr Gly Lys Asp Asn Tyr Ala Gly Val
        275                 280                 285

Thr Trp Asn Asn Val Pro Ser Ala Asp Gly Arg Arg Leu Phe Ile Gly
    290                 295                 300

Trp Met Ser Asn Trp Asp Tyr Ala Gln Asp Val Pro Thr Ser Thr Trp
305                 310                 315                 320

Arg Ser Ala Thr Thr Ile Ala Arg Glu Ile Gln Leu Ile Lys Lys Gly
                325                 330                 335

Asn Lys Tyr Ser Leu Val Ser Asn Pro Val Lys Glu Ile Asn Lys Tyr
            340                 345                 350

Val Ser Lys Thr Ile Lys Gly Lys Asn Leu Lys Gly Lys Gly Met Leu
        355                 360                 365

Ser Ile Leu Glu Pro Gly Lys Ile Asp Leu Thr Gln Ala Ile Val Asn
    370                 375                 380

Phe Asn Leu Lys Asn Leu Lys Gln Asp Thr Tyr Ser Ile Met Leu Ser
385                 390                 395                 400

Asn Ala Ala Gly Glu Ser Leu Thr Phe Gly Leu Asn Asn Ser Asp His
                405                 410                 415

Tyr Leu Phe Leu Asp Arg Ser Lys Ala Gly Lys Asn Asp Phe Ser Asp
            420                 425                 430

Lys Phe Ala Ser Thr Ile Thr Lys Ala Ala Leu Glu Gly Ser Gln Lys
        435                 440                 445

Val Gly Val Phe Lys Ile Ile Leu Asp Lys Thr Ser Ile Glu Ile Phe
    450                 455                 460

Tyr Asn Asn Gly Glu Lys Val Leu Thr Glu Ile Phe Phe Thr Asn Gln
465                 470                 475                 480

Pro Phe Thr Ser Leu Ser Val Ser Ser Asn Glu Gly Ile Glu Leu Asn
                485                 490                 495

Asn Leu Val Leu Asn Gln Leu Asn Ile Asn
            500                 505
```

<210> SEQ ID NO 7
<211> LENGTH: 518
<212> TYPE: PRT
<213> ORGANISM: Aspergillus niger

<400> SEQUENCE: 7

Phe Asn Tyr Asp Gln Pro Tyr Arg Gly Gln Tyr His Phe Ser Pro Gln
1 5 10 15

Lys Asn Trp Met Asn Asp Pro Asn Gly Leu Leu Tyr His Asn Gly Thr
20 25 30

Tyr His Leu Phe Phe Gln Tyr Asn Pro Gly Gly Ile Glu Trp Gly Asn
35 40 45

Ile Ser Trp Gly His Ala Thr Ser Glu Asp Leu Thr His Trp Glu Glu
50 55 60

Gln Pro Val Ala Leu Leu Ala Arg Gly Tyr Gly Ser Asp Val Thr Glu
65 70 75 80

Met Tyr Phe Ser Gly Ser Ala Val Ala Asp Val Asn Asn Thr Ser Gly
85 90 95

Phe Gly Lys Asp Gly Lys Thr Pro Leu Val Ala Met Tyr Thr Ser Tyr
100 105 110

Tyr Pro Val Ala Gln Thr Leu Pro Ser Gly Gln Thr Val Gln Glu Asp
115 120 125

Gln Gln Ser Gln Ser Ile Ala Tyr Ser Leu Asp Asp Gly Leu Thr Trp
130 135 140

Thr Thr Tyr Asp Ala Ala Asn Pro Val Ile Pro Asn Pro Pro Gln Pro
145 150 155 160

Tyr Gln Ala Gln Tyr Gln Asn Phe Arg Asp Pro Phe Val Phe Trp His
165 170 175

Asp Glu Ser His Lys Trp Val Val Val Thr Ser Ile Ala Glu Leu His
180 185 190

Lys Leu Ala Ile Tyr Thr Ser Asp Asn Leu Lys Asp Trp Lys Leu Val
195 200 205

Ser Glu Phe Gly Pro Tyr Asn Ala Gln Gly Gly Val Trp Glu Cys Pro
210 215 220

Gly Leu Phe Lys Leu Pro Leu Asp Gly Gly Ser Ser Thr Lys Trp Val
225 230 235 240

Ile Thr Ser Gly Leu Asn Pro Gly Gly Pro Pro Gly Thr Val Gly Ser
245 250 255

Gly Thr Gln Tyr Phe Val Gly Glu Phe Asp Gly Thr Thr Phe Thr Pro
260 265 270

Asp Ala Asp Thr Val Tyr Pro Gly Asn Ser Thr Ala Asn Trp Met Asp
275 280 285

Trp Gly Pro Asp Phe Tyr Ala Ala Ala Gly Tyr Asn Gly Leu Ser Ile
290 295 300

Lys Asp His Val His Ile Gly Trp Met Asn Asn Trp Gln Tyr Gly Ala
305 310 315 320

Asn Ile Pro Thr Tyr Pro Trp Arg Ser Ala Met Ala Ile Pro Arg His
325 330 335

Leu Ala Leu Lys Thr Ile Asn Asn Lys Thr Thr Leu Val Gln Gln Pro
340 345 350

Gln Glu Ala Trp Ser Ser Ile Ser Ser Lys His Pro Leu Tyr Ser Arg
355 360 365

Thr Tyr Ser Thr Phe Ser Glu Gly Ser Thr Asn Ala Ser Thr Thr Gly
370 375 380

Glu Thr Phe Arg Val Asp Leu Ser Phe Ser Ala Thr Ser Lys Ala Ser
385 390 395 400

Thr Phe Ala Ile Ala Leu Arg Ala Ser Ala Asn Phe Thr Glu Gln Thr

```
                405                 410                 415

Leu Ala Gly Tyr Asp Phe Ala Lys Gln Gln Ile Phe Leu Asp Arg Thr
            420                 425                 430

Lys Ser Gly Asp Val Ser Phe Asp Asn Thr Phe Ala Ser Val Tyr His
        435                 440                 445

Gly Pro Leu Val Pro Asp Ser Thr Gly Met Val Arg Leu Ser Ile Phe
    450                 455                 460

Val Asp Arg Ser Ser Val Glu Val Phe Gly Gly Gln Gly Glu Thr Thr
465                 470                 475                 480

Leu Thr Ala Gln Ile Phe Pro Ser Asn Asp Ala Val His Ala Arg Leu
                485                 490                 495

Val Ser Thr Gly Gly Ala Thr Glu Asp Val Arg Val Asp Val His Asn
            500                 505                 510

Ile Thr Ser Thr Trp Asn
        515


<210> SEQ ID NO 8
<211> LENGTH: 27
<212> TYPE: PRT
<213> ORGANISM: Artificial Sequence
<220> FEATURE:
<223> OTHER INFORMATION: Signal peptide

<400> SEQUENCE: 8

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25


<210> SEQ ID NO 9
<211> LENGTH: 8
<212> TYPE: PRT
<213> ORGANISM: Artificial Sequence
<220> FEATURE:
<223> OTHER INFORMATION: His-tag

<400> SEQUENCE: 9

His His His His His His Pro Arg
1               5


<210> SEQ ID NO 10
<211> LENGTH: 182
<212> TYPE: PRT
<213> ORGANISM: Bacillus cibi

<400> SEQUENCE: 10

Thr Pro Pro Gly Thr Pro Ser Lys Ser Ala Ala Gln Ser Gln Leu Asn
1               5                   10                  15

Ala Leu Thr Val Lys Thr Glu Gly Ser Met Ser Gly Tyr Ser Arg Asp
            20                  25                  30

Leu Phe Pro His Trp Ile Ser Gln Gly Ser Gly Cys Asp Thr Arg Gln
        35                  40                  45

Val Val Leu Lys Arg Asp Ala Asp Ser Tyr Ser Gly Asn Cys Pro Val
    50                  55                  60

Thr Ser Gly Ser Trp Tyr Ser Tyr Tyr Asp Gly Val Thr Phe Thr Asn
65                  70                  75                  80

Pro Ser Asp Leu Asp Ile Asp His Ile Val Pro Leu Ala Glu Ala Trp
                85                  90                  95

Arg Ser Gly Ala Ser Ser Trp Thr Thr Ser Lys Arg Gln Asp Phe Ala
```

```
            100                 105                 110

Asn Asp Leu Ser Gly Pro Gln Leu Ile Ala Val Ser Ala Ser Thr Asn
        115                 120                 125

Arg Ser Lys Gly Asp Gln Asp Pro Ser Thr Trp Gln Pro Pro Arg Ser
    130                 135                 140

Gly Ala Ala Cys Gly Tyr Ser Lys Trp Trp Ile Ser Thr Lys Tyr Lys
145                 150                 155                 160

Trp Gly Leu Ser Leu Gln Ser Ser Glu Lys Thr Ala Leu Gln Gly Met
                165                 170                 175

Leu Asn Ser Cys Ser Tyr
            180


<210> SEQ ID NO 11
<211> LENGTH: 610
<212> TYPE: PRT
<213> ORGANISM: Trichoderma harzianum

<400> SEQUENCE: 11

Ala Pro Ala Asn Val Ala Ile Arg Ser Leu Glu Glu Arg Ala Ser Ser
1               5                   10                  15

Ala Asp Arg Leu Val Phe Cys His Phe Met Ile Gly Ile Val Gly Asp
            20                  25                  30

Arg Gly Ser Ser Ala Asp Tyr Asp Asp Asp Met Gln Arg Ala Lys Ala
        35                  40                  45

Ala Gly Ile Asp Ala Phe Ala Leu Asn Ile Gly Val Asp Gly Tyr Thr
    50                  55                  60

Asp Gln Gln Leu Gly Tyr Ala Tyr Asp Ser Ala Asp Arg Asn Gly Met
65                  70                  75                  80

Lys Val Phe Ile Ser Phe Asp Phe Asn Trp Trp Ser Pro Gly Asn Ala
                85                  90                  95

Val Gly Val Gly Gln Lys Ile Ala Gln Tyr Ala Ser Arg Pro Ala Gln
            100                 105                 110

Leu Tyr Val Asp Asn Arg Pro Phe Ala Ser Ser Phe Ala Gly Asp Gly
        115                 120                 125

Leu Asp Val Asn Ala Leu Arg Ser Ala Ala Gly Ser Asn Val Tyr Phe
    130                 135                 140

Val Pro Asn Phe His Pro Gly Gln Ser Ser Pro Ser Asn Ile Asp Gly
145                 150                 155                 160

Ala Leu Asn Trp Met Ala Trp Asp Asn Asp Gly Asn Asn Lys Ala Pro
                165                 170                 175

Lys Pro Gly Gln Thr Val Thr Val Ala Asp Gly Asp Asn Ala Tyr Lys
            180                 185                 190

Asn Trp Leu Gly Gly Lys Pro Tyr Leu Ala Pro Val Ser Pro Trp Phe
        195                 200                 205

Phe Thr His Phe Gly Pro Glu Val Ser Tyr Ser Lys Asn Trp Val Phe
    210                 215                 220

Pro Gly Gly Pro Leu Ile Tyr Asn Arg Trp Gln Gln Val Leu Gln Gln
225                 230                 235                 240

Gly Phe Pro Met Val Glu Ile Val Thr Trp Asn Asp Tyr Gly Glu Ser
                245                 250                 255

His Tyr Val Gly Pro Leu Lys Ser Lys His Phe Asp Asp Gly Asn Ser
            260                 265                 270

Lys Trp Val Asn Asp Met Pro His Asp Gly Phe Leu Asp Leu Ser Lys
        275                 280                 285
```

```
Pro Phe Ile Ala Ala Tyr Lys Asn Arg Asp Thr Asp Ile Ser Lys Tyr
    290                 295                 300

Val Gln Asn Glu Gln Leu Val Tyr Trp Tyr Arg Arg Asn Leu Lys Ala
305                 310                 315                 320

Leu Asp Cys Asp Ala Thr Asp Thr Thr Ser Asn Arg Pro Ala Asn Asn
                325                 330                 335

Gly Ser Gly Asn Tyr Phe Met Gly Arg Pro Asp Gly Trp Gln Thr Met
            340                 345                 350

Asp Asp Thr Val Tyr Val Ala Ala Leu Leu Lys Thr Ala Gly Ser Val
        355                 360                 365

Thr Val Thr Ser Gly Gly Thr Thr Gln Thr Phe Gln Ala Asn Ala Gly
    370                 375                 380

Ala Asn Leu Phe Gln Ile Pro Ala Ser Ile Gly Gln Gln Lys Phe Ala
385                 390                 395                 400

Leu Thr Arg Asn Gly Gln Thr Val Phe Ser Gly Thr Ser Leu Met Asp
                405                 410                 415

Ile Thr Asn Val Cys Ser Cys Gly Ile Tyr Asn Phe Asn Pro Tyr Val
            420                 425                 430

Gly Thr Ile Pro Ala Gly Phe Asp Asp Pro Leu Gln Ala Asp Gly Leu
        435                 440                 445

Phe Ser Leu Thr Ile Gly Leu His Val Thr Thr Cys Gln Ala Lys Pro
    450                 455                 460

Ser Leu Gly Thr Asn Pro Pro Val Thr Ser Gly Pro Val Ser Ser Leu
465                 470                 475                 480

Pro Ala Ser Ser Thr Thr Arg Ala Ser Ser Pro Pro Val Ser Ser Thr
                485                 490                 495

Arg Val Ser Ser Pro Pro Val Ser Ser Pro Pro Val Ser Arg Thr Ser
            500                 505                 510

Ser Pro Pro Pro Pro Pro Ala Ser Ser Thr Pro Pro Ser Gly Gln Val
        515                 520                 525

Cys Val Ala Gly Thr Val Ala Asp Gly Glu Ser Gly Asn Tyr Ile Gly
    530                 535                 540

Leu Cys Gln Phe Ser Cys Asn Tyr Gly Tyr Cys Pro Pro Gly Pro Cys
545                 550                 555                 560

Lys Cys Thr Ala Phe Gly Ala Pro Ile Ser Pro Pro Ala Ser Asn Gly
                565                 570                 575

Arg Asn Gly Cys Pro Leu Pro Gly Glu Gly Asp Gly Tyr Leu Gly Leu
            580                 585                 590

Cys Ser Phe Ser Cys Asn His Asn Tyr Cys Pro Pro Thr Ala Cys Gln
        595                 600                 605

Tyr Cys
    610
```

<210> SEQ ID NO 12
<211> LENGTH: 4
<212> TYPE: PRT
<213> ORGANISM: Artificial Sequence
<220> FEATURE:
<223> OTHER INFORMATION: Motif

<400> SEQUENCE: 12

```
Trp Met Asn Asp
1
```

<210> SEQ ID NO 13
<211> LENGTH: 41

-continued

```
<212> TYPE: DNA
<213> ORGANISM: Artificial Sequence
<220> FEATURE:
<223> OTHER INFORMATION: Primer

<400> SEQUENCE: 13

acacaactgg ggatccacca tggcttctcg gcttgtgaca g                          41


<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14

agatctcgag aagcttatca gagcaaaatc gaccgcacg                             39


<210> SEQ ID NO 15
<211> LENGTH: 45
<212> TYPE: DNA
<213> ORGANISM: Artificial Sequence
<220> FEATURE:
<223> OTHER INFORMATION: Primer

<400> SEQUENCE: 15

caactggggg cagtgagagc gatatggctc gtcttttgaa ggccg                      45


<210> SEQ ID NO 16
<211> LENGTH: 59
<212> TYPE: DNA
<213> ORGANISM: Artificial Sequence
<220> FEATURE:
<223> OTHER INFORMATION: Primer

<400> SEQUENCE: 16

ctaccgccag cagtgtctgc gatttaattc cacgtcgaag taatattgtg aacatcaac        59
```

ORAL CARE COMPOSITION COMPRISING A FRUCTANASE

CROSS-REFERENCE TO RELATED APPLICATIONS

This application is a 35 U.S.C. 371 national application of PCT/EP2021/073296, filed Aug. 23, 2021, which claims priority or the benefit from European Patent Application No. 20192387.7. filed Aug. 24, 2020. The contents of these applications are fully incorporated herein by reference.

REFERENCE TO A SEQUENCE LISTING

This application contains a Sequence Listing in computer readable form that was submitted as an ASCII text file named 15232-WO-PCT SQ listing_ST25.txt (created on Aug. 23, 2021, 51,920 bytes in size), which is incorporated herein by reference.

FIELD OF THE INVENTION

The present invention relates to an oral care composition comprising a fructanase, use of said composition as medicaments, use of said composition in treatment of oral disease, methods of treatment comprising administering said composition to a human or animal subject, methods of removing biofilm comprising contacting an object with said composition, kits of parts comprising said composition, and fructanases.

BACKGROUND OF THE INVENTION

Biofilms are communities of bacteria that are found on solid surfaces in many different environments, including surfaces of the oral cavity. Oral biofilm, or dental plague, contains many of the bacteria that are associated with oral health issues such as oral malodor, demineralization, dental caries, tooth decay, potential loss of teeth and gum disease (gingivitis and periodontitis).

The formation of oral biofilm occurs in three stages known as the lag phase, growth phase, and steady state, respectively. In the lag phase, glycoproteins from saliva bind to an oral surface such as teeth and create a structure termed the pellicle that functions as attachment site for bacteria. In the growth phase, co-aggregation occurs, i.e., secondary bacterial colonizers attach to the primary bacterial colonizers, causing the diversity of the biofilm to increase and the biofilm to grow and mature. In the steady state, the biofilm growth slows down and eventually stops. This stage-based formation cycle causes biofilms to exist in several consecutive layers, which makes physical abrasion of biofilm more difficult.

Within a biofilm, the residing bacterial cells are distributed in an extracellular polymeric matrix that consists primarily of water, proteins, exopolysaccharides, lipopolysaccharides, lipids, surfactants, and extracellular DNA, with exopolysaccharides occupying a major fraction of the dry weight of biofilm (H. C. Flemming, and J. Wingender (2010), *Nat. Rev. Microbiol.* 8, 623-633). The exopolysaccharides are mainly glucose and fructose homopolymers, including (1-3)-α-D-glucans, (1-4)-α-D-glucans, (1-6)-α-D-glucans and (2-6)-β-D-fructans. These polysaccharides are synthesized from ingested sucrose by glucosyltransferases and fructosyltransferases secreted by oral bacteria such as *Streptococcus* spp., *Lactobacillus* spp., and *Actinomyces* spp.). *Mutans* and dextrans are particularly important glucans in the formation of dental plaque. *Mutans* have a highly branched structure with main chains composed of glucose molecules linked with (1-3)-α bonds and (1-6)-α-glycosidic linkages in their side chains. Dextrans are also high molecular weight polymers of glucose containing numerous consecutive (1-6)-α-linkages in their backbone and side chains, which begin from the (1-3)-α-linkage (M. Pleszczynska et al. (2016), *Biotechnol. Appl. Biochem.* 64(3), 337-346). Fructans are primarily linear polysaccharides and consist mainly of β-(2,6)-linked fructosyl residues and some β-(2,1)-linked branches.

Because of the increased resistance to anti-microbial agents as well as the mechanical properties of biofilm, many current oral care products are rather inefficient in addressing biofilm formation and alleviating the associated oral health issues. The main focus for biofilm removal has been on mechanical abrasion. However, this approach is difficult due to the multilayered nature of biofilms and is further compromised by the fact that mechanical removal of biofilm, e.g., by brushing the teeth, expands and deepens the areas in the oral cavity where biofilms attach and expand, thus potentially increasing the severity of the problem rather than reducing it.

In view of the important role of biofilm in oral disease, there is a need in the art for oral care compositions that can effectively target oral biofilm. WO 1997/38669 (Novozymes) describes oral care compositions comprising a mutanase and a dextranase, WO 1998/57653 (Novozymes) provides oral care compositions comprising a dextranase and a pullulanase, WO 2000/17331 discloses oral care compositions comprising *Paenibacillus* fructanases, and WO 2020/099490 (Novozymes) describes oral care compositions comprising a mutanase and a DNase. However, there is a still need for further and improved oral care compositions that can more effectively degrade oral biofilm

SUMMARY OF THE INVENTION

The present invention provides oral care compositions comprising a fructanase useful for prevention and removal of oral biofilm.

In a first aspect, the present invention relates to an oral care composition comprising (a) a fructanase comprising a GH32 domain, a GH32C domain, and belonging to the WMND clade and comprising the motif WMND (SEQ ID NO: 12); and (b) at least one oral care ingredient; wherein the fructanase has at least two enzymatic activities selected from the group consisting of fructan-degrading activity, levan-degrading activity, inulin-degrading activity, and sucrose-degrading activity.

In a second aspect, the present invention relates to a composition according to the first aspect for use as a medicament.

In a third aspect, the present invention relates to a composition according to the first aspect for use in the treatment of oral disease.

In a fourth aspect, the present invention relates to use of a composition according to the first aspect for treatment or prophylactic treatment of a human or animal subject.

In a fifth aspect, the present invention relates to a method of treatment of a human or animal subject, the method comprising administering a composition according to the first aspect to a human or animal subject.

In a sixth aspect, the present invention relates to a method for removing oral biofilm, the method comprising contacting the oral biofilm with an oral composition according to the first aspect.

In a seventh aspect, the present invention relates to a kit of parts comprising:

a) an oral composition according to the first aspect; and b) instructions for use.

In an eight aspect, the present invention relates to a fructanase having a sequence identity of at least 60% to a polypeptide selected from the group consisting of SEQ ID NO:1, SEQ ID NO:2, SEQ ID NO:3, SEQ ID NO:4, SEQ ID NO:5, SEQ ID NO:6, and SEQ ID NO:7; wherein the polypeptide comprises a GH32 domain, a GH32C domain, belongs to the WMND clade and comprises the motif WMND (SEQ ID NO:12); and wherein the polypeptide has at least two enzymatic activities selected from the group consisting of fructan-degrading activity, levan-degrading activity, inulin-degrading activity, and sucrose-degrading activity.

Definitions

Clade: The term "clade" means a group of polypeptides clustered together on the basis of homologous features traced to a common ancestor. Polypeptide clades can be visualized as phylogenetic trees and a clade is a group of polypeptides that consists of a common ancestor and all its lineal descendants. Polypeptides forming a group within the clade (a subclade) of the phylogenetic tree can also share common properties and are more closely related than other polypeptides in the clade.

Denture: The term "denture" is meant to cover dentures as such as well as braces, aligners, retainers, and the like.

DNase: The term "DNase" means a polypeptide having DNase (deoxyribonuclease) activity that catalyzes the hydrolytic cleavage of phosphodiester linkages in a DNA backbone, thus degrading DNA. Exo-deoxyribonuclease cut or cleaves residues at the end of the DNA backbone where endo-deoxyribonucleases cleaves or cut within the DNA backbone. A DNase may cleave only double-stranded DNA or may cleave double stranded and single stranded DNA. The term "DNases" and the expression "a polypeptide having DNase activity" are used interchangeably throughout this application. For purposes of the present invention, DNase activity may be determined according to the procedure described in Assay I or Assay II of WO 2020/099491 (reproduced in the Examples below).

Fragment: The term "fragment" means a polypeptide having one or more amino acids absent from the amino and/or carboxyl terminus of a mature polypeptide or domain, where the fragment has fructanase activity.

Fructanase: The term "fructanase" means polypeptide having fructanase activity that catalyzes the hydrolytic cleavage of the glycosidic linkages in fructans, thus degrading fructans. The term "fructanase" and the expression "a polypeptide having fructanase activity" are used interchangeably throughout this application.

Fructans are polymers of fructose molecules that is found in certain classes of Gram-positive and Gram-negative bacteria, for example in *Bacillus, Streptococcus, Pseudomonas, Erwinia* and *Actinomyces*, as well as in some fungi, for example *Aspergillus* and *Penicillium*. Fructan molecules produced by bacteria consist mainly of β-(2,6)-linked fructosyl residues and some β-(2,1)-linked branches. Some fructans are called levans and can reach a degree of polymerization (DP) of more than 100,000 fructosyl units. (Vijn and Smeekens, Plant Physiology 1999, Vol. 120: 351-359; Van den Ende, *J Exp Bot.* 2018, Vol. 69 (18): 4227-4231). Another major type of fructan, inulin, comprises primarily β-(2,1)-linked fructosyl residues and some β-(2,6)-linked branches. Thus, fructanases are polypeptides that degrade fructan, levan, and/or inulin, and the term "fructanase activity" comprises fructan-degrading activity, levan-degrading activity, and/or inulin-degrading activity. In addition, many fructanases also degrade sucrose, a disaccharide containing glucose and fructose. Thus, many fructanases also have sucrose-degrading activity. For purposes of the present invention, fructan-degrading activity, levan-degrading activity, inulin-degrading activity, and sucrose-degrading activity (i.e., enzymatic activities) may be determined according to the methods described in Example 4 below.

The fructanases of the invention have at least two enzymatic activities selected from the group consisting of fructan-degrading activity, levan-degrading activity, inulin-degrading activity, and sucrose-degrading activity.

In a preferred embodiment, the fructanases have at least two enzymatic activities selected from the group consisting of fructan-degrading activity, levan-degrading activity, and inulin-degrading activity.

Fructanases of the invention belong to the glycosyl hydrolase 32 (GH32) family that contains enzymes that hydrolyze fructose-containing polysaccharides. The GH32 family includes inulinases (EC 3.2.1.7), 2,6-β-fructan 6-levanbiohydrolases (EC 3.2.1.64), levanases (EC 3.2.1.65), fructan β-fructosidases (EC 3.2.1.80), fructan β-(2,1)-fructosidases (EC 3.2.1.153), and fructan β-(2,6)-fructosidases (EC 3.2.1.154). These enzymatic activities provide degradation of the fructose-containing polysaccharides fructan, levan, and inulin.

Thus, in a preferred embodiment, the fructanases comprise at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), and fructan β-(2,6)-fructosidase activity (EC 3.2.1.154), wherein the fructanases degrade at least two, e.g., three, polysaccharides selected from the group consisting of fructan, levan, and inulin.

The fructanases may have endo-acting activity and/or exo-acting activity. Endo-acting activity implies random cleavage of the glycosidic linkages of the polysaccharide substrate, whereas exo-acting activity implies that the fructanases act from the non-reducing and/or reducing end of the polysaccharide substrate.

Mutanase: The term "mutanase" means a polypeptide having mutanase activity that catalyzes the hydrolytic cleavage of −1,3-glycosidic linkages in mutan, thereby degrading mutan. The term "mutanase" and the expression "a polypeptide having mutanase activity" are used interchangeably throughout this application. For purposes of the present invention, mutanase activity may be determined according to the procedure described in WO 2017/083228 or in A. Wiater et al., *Mycological Research*, vol. 105, pp. 1357-1363, 2001.

Parent or parent fructanase: The term "parent" or "parent fructanase" means a fructanase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Variant: The term "variant" means a fructanase comprising an alteration, i.e., a substitution, insertion, and/or deletion, at one or more positions compared to a parent fructanase. A substitution means replacement of the amino acid occupying a position with a different amino acid; a deletion means removal of the amino acid occupying a position; and an insertion means adding an amino acid adjacent to and immediately following the amino acid occupying a position.

Motif Nomenclature

For purposes of the present invention, the nomenclature [G/N] or [GN] means that the amino acid at this position may be a glycine (Gly, G) or an asparagine (Asn, N). Likewise, the nomenclature [T/D/S] or [TDS] means that the amino acid at this position may be a threonine (Thr, T), aspartic acid (Asp, D), or serine (Ser, S), and so forth for other combinations as described herein. Unless otherwise limited further, the amino acid X is defined such that it may be any of the natural amino acids.

BRIEF DESCRIPTION OF THE FIGURES

FIG. 1 shows an example of the thermal stability data generated using the nanoDSF instrument. Panel A is an example of the data obtained (the ratio of the fluorescence emission at 350 nm to 330 nm) in triplicate for SEQ ID NO:2 as a function of temperature. Panel B shows the first derivative of the raw data in Panel A. The peak maximum in the first derivative plot corresponds to the mid-point of the thermal unfolding transition, referred to as Tm. In this example, the Tm corresponds to 66.1° C. and is highly reproducible within the three replicates.

SEQUENCE OVERVIEW

SEQ ID NO:1 is a fructanase isolated from *Penicillium ochrochloron.*

SEQ ID NO:2 is a fructanase isolated from *Bacillus licheniformis.*

SEQ ID NO:3 is a fructanase isolated from *Bacillus licheniformis* S16.

SEQ ID NO:4 is a fructanase isolated from *Arthrobacter* sp. Leaf337.

SEQ ID NO:5 is a fructanase isolated from *Bacillus subtilis.*

SEQ ID NO:6 is a fructanase isolated from *Flavobacterium banpakuense.*

SEQ ID NO:7 is a fructanase isolated from *Aspergillus niger.*

SEQ ID NO:8 is the secretion signal used during expression of SEQ ID NOs:2-6.

SEQ ID NO:9 is the His-tag used during expression of SEQ ID NOs:2-6.

SEQ ID NO:10 is a DNase isolated from *Bacillus cibi.*

SEQ ID NO: 11 is a mutanase isolated from *Trichoderma harzianum.*

SEQ ID NO:12 is the motif WMND.

SEQ ID NO:13 is a primer.

SEQ ID NO:14 is a primer.

SEQ ID NO:15 is a primer.

SEQ ID NO:16 is a primer.

DETAILED DESCRIPTION OF THE INVENTION

The present invention relates to oral care compositions comprising fructanases that are particularly suitable for oral care applications. These fructanases all comprise a GH32 domain, a GH32C domain, belong to the WMND clade, and comprise the sequence motif WMND (SEQ ID NO:12). These fructanases are able to degrade the fructose-containing poly- and disaccharides fructan, levan, inulin, and sucrose, and they are highly active in prevention and removal of oral biofilm. It is speculated that the ability of these fructanases to degrade especially fructan, levan, and inulin provides the good effects on prevention and removal of oral biofilm. In addition, these fructanases are highly stable when co-formulated with a wide range of oral care ingredients, making them very suitable for use in oral care formulations.

Thus, the present invention relates to an oral care composition comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two enzymatic activities selected from the group consisting of fructan-degrading activity, levan-degrading activity, inulin-degrading activity, and sucrose-degrading activity.

Fructanases

In the context of the present invention, suitable fructanases are those of the glycosyl hydrolase 32 (GH32) family that comprises a GH32 domain, a GH32C domain, belong to the WMND clade, and comprise the WMND motif. Such fructanases are generally of microbial origin, preferably of bacterial or fungal origin.

In an embodiment, the fructanase is selected from the group consisting of:

a) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:1, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

b) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:2, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

c) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:3, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

d) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:4, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

e) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:5, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

f) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:6, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity;

g) a polypeptide having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to SEQ ID NO:7, wherein the polypeptide comprises a GH32 domain, a GH32C domain, belongs to the WMND clade and comprises the motif WMND (SEQ ID NO:12), and wherein the polypeptide has at least two enzymatic activities selected from the group consisting of fructan-degrading activity, levan-degrading activity, inulin-degrading activity, and sucrose-degrading activity; and h) a fragment of the polypeptide of (a), (b), (c), (d), (e), (f) or (g), wherein said fragment comprises a GH32 domain, a GH32C domain, belongs to the WMND clade and comprises the motif WMND (SEQ ID NO:12), and wherein the fragment has at least two enzymatic activities selected from the group consisting of fructan-degrading activity, levan-degrading activity, inulin-degrading activity, and sucrose-degrading activity.

In one embodiment, the fructanase is selected from the group consisting of:

a) a polypeptide comprising, consisting essentially of, or consisting of SEQ ID NO:1;
b) a polypeptide comprising, consisting essentially of, or consisting of SEQ ID NO:2;
c) a polypeptide comprising, consisting essentially of, or consisting of SEQ ID NO:3;
d) a polypeptide comprising, consisting essentially of, or consisting of SEQ ID NO:4;
e) a polypeptide comprising, consisting essentially of, or consisting of SEQ ID NO:5;
f) a polypeptide comprising, consisting essentially of, or consisting of SEQ ID NO:6; and
g) a polypeptide comprising, consisting essentially of, or consisting of SEQ ID NO:7.

The fructanases have at least two, e.g., at least three, or four, enzymatic activities selected from the group consisting of fructan-degrading activity, levan-degrading activity, inulin-degrading activity, and sucrose-degrading activity. The fructanase may have endo-acting activity and/or exo-acting activity, preferably exo-acting activity. Preferably, the fructanases have at least two, e.g., three, enzymatic activities selected from the group consisting of fructan-degrading activity, levan-degrading activity, and inulin-degrading activity.

Preferably, the fructanase has fructan-degrading activity, levan-degrading activity, and inulin-degrading activity.

Preferably, the fructanase has fructan-degrading activity and levan-degrading activity.

Preferably, the fructanase has fructan-degrading activity and inulin-degrading activity.

Preferably, the fructanase has levan-degrading activity and inulin-degrading activity.

The fructanase may have on par or improved enzymatic activity, in particular, and independently, on par or improved fructan-degrading activity, on par or improved levan-degrading activity, on par or improved inulin-degrading activity, and on par or improved sucrose-degrading activity. In some embodiments, the at least two enzymatic activities are, independently, on par or improved compared to a fructanase that does not comprise a GH32 domain, a GH32C domain, belong to the WMND clade, and comprise the sequence motif WMND (SEQ ID NO:12).

Preferably, the fructanase has, independently, i) on par or improved fructan-degrading activity, e.g., 100%, 105%, 110%, 115%, 120%, 125%, 130%, 140%, 150%, 175%, 200%, 250%, 300%, 400%, 500%, or more, fructan-degrading activity, ii) on par or improved levan-degrading activity, e.g., 100%, 105%, 110%, 115%, 120%, 125%, 130%, 140%, 150%, 175%, 200%, 250%, 300%, 400%, 500%, or more, levan-degrading activity, iii) on par or improved inulin-degrading activity, e.g., 100%, 105%, 110%, 115%, 120%, 125%, 130%, 140%, 150%, 175%, 200%, 250%, 300%, 400%, 500%, or more, inulin-degrading activity, and iv) iii) on par or improved sucrose-degrading activity, e.g., 100%, 105%, 110%, 115%, 120%, 125%, 130%, 140%, 150%, 175%, 200%, 250%, 300%, 400%, 500%, or more, sucrose-degrading activity.

Preferably, the fructanase has, independently, i) on par or improved fructan-degrading activity, e.g., 100%, 105%, 110%, 115%, 120%, 125%, 130%, 140%, 150%, 175%, 200%, 250%, 300%, 400%, 500%, or more, fructan-degrading activity, ii) on par or improved levan-degrading activity, e.g., 100%, 105%, 110%, 115%, 120%, 125%, 130%, 140%, 150%, 175%, 200%, 250%, 300%, 400%, 500%, or more, levan-degrading activity, and iii) on par or improved inulin-degrading activity, e.g., 100%, 105%, 110%, 115%, 120%, 125%, 130%, 140%, 150%, 175%, 200%, 250%, 300%, 400%, 500%, or more, inulin-degrading activity.

Preferably, the fructanase has, independently, i) on par or improved fructan-degrading activity, e.g., 100%, 105%, 110%, 115%, 120%, 125%, 130%, 140%, 150%, 175%, 200%, 250%, 300%, 400%, 500%, or more, fructan-degrading activity, and ii) on par or improved levan-degrading activity, e.g., 100%, 105%, 110%, 115%, 120%, 125%, 130%, 140%, 150%, 175%, 200%, 250%, 300%, 400%, 500%, or more, levan-degrading activity.

Preferably, the fructanase has, independently, i) on par or improved fructan-degrading activity, e.g., 100%, 105%, 110%, 115%, 120%, 125%, 130%, 140%, 150%, 175%, 200%, 250%, 300%, 400%, 500%, or more, fructan-degrading activity, and ii) on par or improved inulin-degrading activity, e.g., 100%, 105%, 110%, 115%, 120%, 125%, 130%, 140%, 150%, 175%, 200%, 250%, 300%, 400%, 500%, or more, inulin-degrading activity.

Preferably, the fructanase has, independently, i) on par or improved levan-degrading activity, e.g., 100%, 105%, 110%, 115%, 120%, 125%, 130%, 140%, 150%, 175%, 200%, 250%, 300%, 400%, 500%, or more, levan-degrading activity, and ii) on par or improved inulin-degrading activity, e.g., 100%, 105%, 110%, 115%, 120%, 125%, 130%, 140%, 150%, 175%, 200%, 250%, 300%, 400%, 500%, or more, inulin-degrading activity.

Preferably, the fructanase comprises at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), and fructan β-(2,6)-fructosidase activity (EC 3.2.1.154). These enzymatic activities all imply the degradation of the fructose-containing polysaccharides fructan, levan, and inulin. The at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), and fructan β-(2,6)-fructosidase activity (EC 3.2.1.154) may be, independently, on par or improved, e.g., 100%, 105%, 110%, 115%, 120%, 125%, 130%, 140%, 150%, 175%, 200%, 250%, 300%, 400%, 500%, or more. In some embodiments, the at least two enzymatic activities are, independently, on par or improved compared to a fructanase that does not comprise a GH32 domain, a GH32C domain, belong to the WMND clade, and comprise the sequence motif WMND (SEQ ID NO:12).

The fructanases are highly stabile in formulations and/or formats suitable for oral care, in particular formulations or formats such as toothpastes, mouthwashes, lozenges, mints, gums, candy, etc. The high stability, e.g., on par or improved stability, may be on par or improved physical and/or chemical stability. On par or improved chemical stability, i.e., on par or improved stability in the presence of another agent (e.g., another enzyme, an active ingredient, an excipient, or a solvent) may occur when the fructanase and the other agent are co-formulated and/or co-administered, preferably upon co-formulation.

In the context of the present invention, the term "on par chemical stability" means that the chemical stability of a fructanase in the presence of (or, alternatively stated, co-formulated with) a particular oral care ingredient or component is within +/−5% of the chemical stability of the same fructanase alone (i.e., in the absence of said oral care ingredient).

In the context of the present invention, the term "improved chemical stability" means that the chemical stability of a fructanase in the presence of (or, alternatively stated, co-formulated with) a particular oral care ingredient or component is improved more than 5%, e.g., 10%, 15%, 20%, 25%, 30%, 40%, 50%, 60%, 70%, 80%, 90%, 100%, or even more, compared to the chemical stability of the same fructanase alone (i.e., in the absence of said oral care ingredient).

For purposes of the present invention, chemical stability may be determined according to Example 3 below as thermal stability defined by the thermal unfolding transition midpoint (Tm) in the presence of a particular oral care ingredient.

In one embodiment, the fructanase has on par or improved chemical stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol.

In one embodiment, the fructanase has on par or improved chemical stability in the presence of at least one oral care ingredient selected from the group consisting of benzoate (e.g., sodium benzoate), arginine, EDTA, ethanol, glycerol, sodium phosphate, sorbitol, potassium sorbate, fluoride (e.g., sodium fluoride), hydrogen peroxide, and mannitol.

In one embodiment, the oral care composition comprises benzoate, e.g., sodium benzoate, and the fructanase has on par or improved chemical stability in the presence of benzoate, e.g., sodium benzoate. Preferably, the fructanase has on par or improved chemical stability in the presence of 0.01-5% benzoate, more preferably 0.05-2.5% benzoate, even more preferably 0.1-1% benzoate, most preferably 0.1-0.5% benzoate. Preferably, the fructanase has on par or improved chemical stability in the presence of 1-100 mM benzoate, more preferably 5-50 mM benzoate, most preferably 10-35 mM benzoate.

In one embodiment, the oral care composition comprises arginine, and the fructanase has on par or improved chemical stability in the presence of arginine. Preferably, the fructanase has on par or improved chemical stability in the presence of 1-500 mM arginine, more preferably 25-250 mM arginine, even more preferably 25-100 mM arginine, most preferably 30-90 mM arginine.

In one embodiment, the oral care composition comprises EDTA, and the fructanase has on par or improved chemical stability in the presence of EDTA. Preferably, the fructanase has on par or improved chemical stability in the presence 0.1-10 mM EDTA, more preferably 0.5-5 mM EDTA, most preferably 1 mM EDTA.

In one embodiment, the oral care composition comprises ethanol, and the fructanase has on par or improved chemical stability in the presence of ethanol. Preferably, the fructanase has on par or improved chemical stability in the presence of 0.1-20% ethanol, more preferably 1-10% ethanol, even more preferably 2.5-7.5% ethanol, most preferably 5% ethanol. Preferably, the fructanase has on par or improved chemical stability in the presence of 1-100000 mM ethanol, more preferably 100-10000 mM ethanol, most preferably 1000 mM ethanol.

In one embodiment, the oral care composition comprises glycerol, and the fructanase has on par or improved chemical stability in the presence of glycerol. Preferably, the fructanase has on par or improved chemical stability in the presence of 1-50% glycerol, more preferably 5-40% glycerol, most preferably 10-30% glycerol. Preferably, the fructanase has on par or improved chemical stability in the presence of 100-10000 mM glycerol, more preferably 500-5000 mM glycerol, even more preferably 750-4000 mM glycerol, most preferably 1000-3250 mM glycerol.

In one embodiment, the oral care composition comprises phosphate, e.g., sodium phosphate or potassium phosphate, and the fructanase has on par or improved chemical stability in the presence of phosphate, e.g., sodium phosphate or potassium phosphate. Preferably, the fructanase has on par or improved chemical stability in the presence of 1-50 mM phosphate, more preferably 2.5-25 mM phosphate, even more preferably 5-10 mM phosphate.

In one embodiment, the oral care composition comprises sorbitol, and the fructanase has on par or improved chemical stability in the presence of sorbitol. Preferably, the fructanase has on par or improved chemical stability in the presence of 0.1-70% sorbitol, more preferably 1-60% sorbitol, even more preferably 5-50% sorbitol, most preferably 10-40% sorbitol. Preferably, the fructanase has on par or improved chemical stability in the presence of 100-10000 mM sorbitol, more preferably 250-5000 mM sorbitol, even more preferably 500-2500 mM sorbitol, most preferably 550-2200 mM sorbitol.

In one embodiment, the oral care composition comprises sorbate, e.g., sodium sorbate, potassium sorbate, or calcium sorbate, and the fructanase has on par or improved chemical stability in the presence of sorbate, e.g., sodium sorbate, potassium sorbate, or calcium sorbate. Preferably, the fructanase has on par or improved chemical stability in the presence of 0.01-5% sorbate, more preferably 0.05-2.5% sorbate, even more preferably 0.1-1% sorbate, most preferably 0.1-0.5% sorbate. Preferably, the fructanase has on par or improved chemical stability in the presence of 1-100 mM sorbate, more preferably 5-75 mM sorbate, even more preferably 7.5-50 mM sorbate, most preferably 10-35 mM sorbate.

In one embodiment, the oral care composition comprises fluoride, e.g., sodium fluoride, sodium monofluorophosphate, calcium fluoride, or stannous fluoride, and the fructanase has on par or improved chemical stability in the presence of fluoride, e.g., sodium fluoride, sodium monofluorophosphate, calcium fluoride, or stannous fluoride. Preferably, the fructanase has on par or improved chemical stability in the presence of 1-5000 ppm fluoride, more preferably 500-2500 ppm fluoride, most preferably 1,000-1500 ppm fluoride. Preferably, the fructanase has on par or improved chemical stability in the presence of 1-100 mM fluoride, more preferably 5-75 mM fluoride, even more preferably 10-50 mM fluoride, most preferably 20-40 mM fluoride.

In one embodiment, the oral care composition comprises peroxide, e.g., hydrogen peroxide, and the fructanase has on par or improved chemical stability in the presence of peroxide, e.g., hydrogen peroxide. Preferably, the fructanase has on par or improved chemical stability in the presence of 1-1000 mM peroxide, more preferably 50-750 mM peroxide, most preferably 100-500 mM peroxide.

In one embodiment, the oral care composition comprises mannitol, and the fructanase has on par or improved chemical stability in the presence of mannitol. Preferably, the fructanase has on par or improved chemical stability in the presence of 1-1000 mM mannitol, more preferably 150-750 mM mannitol, most preferably 250-550 mM mannitol.

The fructanases prevent and/or remove oral biofilm. In an embodiment, the fructanase has on par or improved effect on biofilm prevention, e.g., 100%, 105%, 110%, 115%, 120%, 125%, 130%, 140%, 150%, 175%, 200%, 250%, 300%, 400%, 500%, or more. In a preferred embodiments the fructanase has on par or improved effect on biofilm prevention compared to a fructanase that does not comprise a GH32 domain, a GH32C domain, belong to the WMND clade, and comprise the sequence motif WMND (SEQ ID NO:12). In an embodiment, the fructanase has on par or improved effect on biofilm removal, e.g., 100%, 105%, 110%, 115%, 120%, 125%, 130%, 140%, 150%, 175%, 200%, 250%, 300%, 400%, 500%, or more. In a preferred embodiment, the fructanase has on par or improved effect on biofilm removal compared to a fructanase that does not comprise a GH32 domain, a GH32C domain, belong to the WMND clade, and comprise the sequence motif WMND (SEQ ID NO:12).

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:1, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Penicillium*, e.g., obtainable from *Penicillium ochrochloron*. In a preferred embodiment, the polypeptide comprises, consists essentially of, or consists of SEQ ID NO:1 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:1. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:2, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus licheniformis*. In a preferred embodiment, the polypeptide comprises, consists essentially of, or consists of SEQ ID NO:2 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:2. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:3, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus licheniformis*, preferably *Bacillus licheniformis* S16. In a preferred embodiment, the polypeptide comprises, consists essentially of, or consists of SEQ ID NO:3 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:3. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:4, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Arthrobacter*, e.g., obtainable from *Arthrobacter* sp. Leaf337. In a preferred embodiment, the polypeptide comprises, consists essentially of, or consists of SEQ ID NO:4 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:4. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:5, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus subtilis. In a preferred embodiment, the polypeptide comprises, consists essentially of, or consists of SEQ ID NO:*5 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:5. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:6, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Flavobacterium*, e.g., obtainable from *Flavobacterium banpakuense*. In a preferred embodiment, the polypeptide comprises, consists essentially of, or consists of SEQ ID NO:6 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:6. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the oral care compositions of the present invention comprises a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:7, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Aspergillus*, e.g., obtainable from *Aspergillus niger*. In a preferred embodiment, the polypeptide comprises, consists essentially of, or consists of SEQ ID NO:7 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:7. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a fructanase having a sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, to a polypeptide selected from the group consisting of SEQ ID NO:1, SEQ ID NO:2, SEQ ID NO:3, SEQ ID NO:4, SEQ ID NO:5, SEQ ID NO:6, and SEQ ID NO:7, wherein the polypeptide comprises a GH32 domain, a GH32C domain, belongs to the WMND clade and comprises the motif WMND (SEQ ID NO:12); and wherein the polypeptide has at least two enzymatic activities selected from the group consisting of fructan-degrading activity, levan-degrading activity, inulin-degrading activity, and sucrose-degrading activity In one aspect, the present invention relates to a fructanase selected from the group consisting of:

a) a polypeptide comprising, consisting essentially of, or consisting of SEQ ID NO:1;
b) a polypeptide comprising, consisting essentially of, or consisting of SEQ ID NO:2;
c) a polypeptide comprising, consisting essentially of, or consisting of SEQ ID NO:3;
d) a polypeptide comprising, consisting essentially of, or consisting of SEQ ID NO:4;
e) a polypeptide comprising, consisting essentially of, or consisting of SEQ ID NO:5;
f) a polypeptide comprising, consisting essentially of, or consisting of SEQ ID NO:6; and
g) a polypeptide comprising, consisting essentially of, or consisting of SEQ ID NO:7.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:1, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Penicillium*, e.g., obtainable from *Penicillium ochrochloron*. In a preferred embodiment, the polypeptide comprises, consists essentially of, or consists of SEQ ID NO:1 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:1. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:2, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus licheniformis*. In a preferred embodiment, the polypeptide comprises, consists essentially of, or consists of SEQ ID NO:2 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:2. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:3, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus licheniformis*, preferably *Bacillus licheniformis* S16. In a preferred embodiment, the polypeptide comprises, consists essentially of, or consists of SEQ ID NO:3 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:3. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:4, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Arthrobacter*, e.g., obtainable from *Arthrobacter* sp. Leaf337. In a preferred embodiment, the polypeptide comprises, consists essentially of, or consists of SEQ ID NO:4 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:4. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:5, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Bacillus*, e.g., obtainable from *Bacillus subtilis*. In a preferred embodiment, the polypeptide comprises, consists essentially of, or consists of SEQ ID NO:5 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:5. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:6, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Flavobacterium*, e.g., obtainable from *Flavobacterium banpakuense*. In a preferred embodiment, the polypeptide comprises, consists essentially of, or consists of SEQ ID NO:6 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:6. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

In one aspect, the present invention relates to a polypeptide, preferably an isolated or purified polypeptide, having a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% to SEQ ID NO:7, wherein the polypeptide comprises a GH32 domain, a GH32C domain, belongs to the WMND clade and comprises the motif WMND (SEQ ID NO:12), and wherein the polypeptide has at least two, e.g., at least three, or four, enzymatic activities selected from the group consisting of fructan-degrading activity, levan-degrading activity, inulin-degrading activity, and sucrose-degrading activity. In one embodiment, the polypeptide is obtainable from *Aspergillus*, e.g., obtainable from *Aspergillus niger*. In a preferred embodiment, the polypeptide comprises, consists essentially of, or consists of SEQ ID NO:7 or a fragment or variant thereof having fructanase activity. In one embodiment, the polypeptide differs by up to 10 amino acids, e.g., 1, 2, 3, 4, 5, 6, 7, 8, 9, or 10, from SEQ ID NO:7. In a preferred embodiment, the polypeptide has at least two, e.g., three, enzymatic activities selected from the group consisting of fructan-degrading activity, levan-degrading activity, and inulin-degrading activity. Preferably, the polypeptide has endo-acting activity and/or exo-acting activity, most preferably exo-acting activity. In a preferred embodiment, the polypeptide has at least two, e.g., at least three, at least four, at least five, or six, enzymatic activities selected from the group consisting of inulinase activity (EC 3.2.1.7), 2,6-β-fructan 6-levanbiohydrolase activity (EC 3.2.1.64), levanase activity (EC 3.2.1.65), fructan β-fructosidase activity (EC 3.2.1.80), fructan β-(2,1)-fructosidase activity (EC 3.2.1.153), fructan β-(2,6)-fructosidase activity (EC 3.2.1.154), and degrades at least two polysaccharides selected from the group consisting of fructan, levan, and inulin. In one embodiment, the polypeptide has on par or improved stability in the presence of at least one oral care ingredient selected from the group consisting of benzoate (preferably sodium benzoate), arginine, EDTA, ethanol, glycerol, phosphate (preferably sodium phosphate or potassium phosphate), sorbitol, potassium sorbate, fluoride (preferably sodium fluoride, sodium monofluorophosphate, calcium fluoride, or stannous fluoride), hydrogen peroxide, and mannitol. In one embodiment, the polypeptide has on par or improved effect on biofilm prevention and/or removal.

Other Enzymes with Beneficial Effects in Oral Care

The oral care compositions of the invention may also comprise one or more additional enzyme(s) that have beneficial effects for oral care.

Thus, in one aspect, the oral care compositions of the invention comprise (a) a fructanase comprising a GH32 domain, a GH32C domain, and belonging to the WMND clade and comprising the motif WMND (SEQ ID NO:12); (b) at least one oral care ingredient; and (c) at least one other enzyme; wherein the fructanase has at least two, e.g., at least three, or four, enzymatic activities selected from the group consisting of fructan-degrading activity, levan-degrading activity, inulin-degrading activity, and sucrose-degrading activity. Preferably the at least one other enzyme is selected from the group consisting of DNase, dispersin, protease, lipase, carbohydrase, dextranase, mutanase, oxidoreductase, laccase, peroxidase, oxidase, and lysozyme.

In general, the properties of the selected enzyme(s) should be compatible with the selected oral care composition, (i.e., pH-optimum, compatibility with other enzymatic and non-enzymatic ingredients, etc.), and the enzyme(s) should be present in effective amounts.

Examples of DNases, dispersins, proteases, lipases, carbohydrases, dextranases, mutanases, oxidoreductases, laccases, peroxidases, oxidases, and lysozymes suitable for use in the compositions of the invention include those that are described below as well as others available in the art, which may be readily identified by the skilled artisan.

DNases

In one aspect, the present invention relates to an oral care composition comprising (a) a fructanase comprising a GH32 domain, a GH32C domain, and belonging to the WMND clade and comprising the motif WMND (SEQ ID NO:12); (b) a DNase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

The term "DNase" means a polypeptide having DNase (deoxyribonuclease) activity that catalyzes the hydrolytic cleavage of phosphodiester linkages in a DNA backbone, thus degrading DNA. Exodeoxyribonuclease cut or cleaves residues at the end of the DNA back bone where endo-deoxyribonucleases cleaves or cut within the DNA backbone. A DNase may cleave only double-stranded DNA or may cleave double stranded and single stranded DNA.

Preferably the DNase is selected from any of the enzyme classes E.C.3.1, preferably E.C.3.1.21, e.g., such as E.C.3.1.21.X, where X=1, 2, 3, 4, 5, 6, 7, 8 or 9, or, e.g., Deoxyribonuclease 1, Deoxyribonuclease IV, Type I site-specific deoxyribonuclease, Type II site-specific deoxyribonuclease, Type III site-specific deoxyribonuclease, CC-preferring endo-deoxyribonuclease, Deoxyribonuclease V, T(4) deoxyribonuclease II, T(4) deoxyribonuclease IV or E.C. 3.1.22.Y, where Y=1, 2, 4 or 5, e.g., Deoxyribonuclease II, *Aspergillus* deoxyribonuclease K(1), Crossover junction endo-deoxyribonuclease, Deoxyribonuclease X.

Preferably, the polypeptide having DNase activity is obtained from a microorganism and the DNase is a microbial enzyme. The DNase is preferably of fungal or bacterial origin.

The DNase may be obtainable from *Bacillus*, e.g, *Bacillus licheniformis, Bacillus subtilis, Bacillus* sp-62451, *Bacillus horikoshii, Bacillus* sp-16840, *Bacillus* sp-62668, *Bacillus* sp-13395, *Bacillus horneckiae, Bacillus* sp-11238, *Bacillus cibi, Bacillus idriensis, Bacillus* sp-62520, *Bacillus* sp-16840, *Bacillus* sp-62668, *Bacillus algicola, Bacillus vietnamensis, Bacillus hwajinpoensis, Bacillus indicus, Bacillus marisflavi, Bacillus luciferensis*, and *Bacillus* sp. SA2-6.

The DNase may also be obtained from any of the following: *Pyrenochaetopsis* sp., *Vibrissea flavovirens, Setosphaeria rostrate, Endophragmiella valdina, Corynespora cassiicola, Paraphoma* sp. XZ1965, *Monilinia fructicola, Curvularia lunata, Penicillium reticulisporum, Penicillium quercetorum, Setophaeosphaeria* sp., *Alternaria, Alternaria* sp. XZ2545, *Trichoderma reesei, Chaetomium thermophilum, Scytalidium thermophilum, Metapochonia suchlasporia, Daldinia fissa, Acremonium* sp. XZ2007, *Acremonium* sp. XZ2414, *Acremonium dichromosporum, Sarocladium* sp. XZ2014, *Metarhizium* sp. HNA15-2, *Isaria tenuipes Scytalidium circinatum, Metarhizium lepidiotae, Thermobispora bispora, Sporormia fimetaria, Pycnidiophora* cf. dispera, Environmental sample D, Environmental sample O, Clavicipitaceae sp-70249, *Westerdykella* sp. AS85-2, *Humicolopsis cephalosporioides, Neosartorya massa, Roussoella intermedia, Pleosporales, Phaeosphaeria*, or *Didymosphaeria futilis*.

In are particularly preferred embodiment, the DNase exhibits improved stability in oral care formulations, e.g., toothpastes, mouthwashes, mints, lozenges, gums, etc., and/or in the presence of oral care components, e.g., sodium dodecyl sulphate (SDS) or fluoride sources such as sodium fluoride, sodium monofluorophosphate, calcium fluoride, or stannous fluoride. Examples of such DNases with improved stability are disclosed in WO 2020/099491.

In one embodiment, the DNase is obtainable from *Bacillus*, e.g., obtainable from *Bacillus cibi*, and has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, to SEQ ID NO:10, and has DNase activity. In a preferred embodiment, the DNase differs by up to 10 amino acids, e.g., 1, 2, 3, 4, 5, 6, 7, 8, 9, or 10, from the polypeptide shown in SEQ ID NO:10. In a preferred embodiment, the DNase comprises, consists essentially of, or consists of SEQ ID NO:10.

Dispersins

In one aspect, the present invention relates to an oral care composition comprising (a) a fructanase comprising a GH32 domain, a GH32C domain, and belonging to the WMND clade and comprising the motif WMND (SEQ ID NO:12); (b) a dispersin; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Dispersins are polypeptides having hexosaminidase activity, preferably poly-N-acetylglucosamine (PNAG) degrading activity. One example is dispersin B (DspB), which is a beta-N-acetylglucosamininidases belonging to the Glycoside Hydrolase 20 family. Dispersins are produced by the periodontal pathogen *Aggregatibacter actinomycetemcomitans*, a Gram-negative oral bacterium. Dispersin B is a beta-hexosaminidase that specifically hydrolyzes beta-1,6-glycosidic linkages of acetylglucosamine polymers found in biofilm. Suitable dispersin B and variants thereof are described in WO 2014/061117 and WO 2017/186936.

Other suitable dispersins include dispersin 2 and variants thereof (WO 2017/186936), dispersin 5 and variants thereof, and dispersin 8 and variants thereof.

In an embodiment, the compositions of the invention comprise a dispersin selected from dispersin B, dispersin 2, dispersin 5, and dispersin 8.

In an embodiment, the compositions of the invention comprise a polypeptide having hexosaminidase activity or a polypeptide comprising a catalytic domain belonging to the Glycoside Hydrolase family 20 (GH20, www.cazy.org).

Proteases

In one aspect, the present invention relates to an oral care composition comprising (a) a fructanase comprising a GH32 domain, a GH32C domain, and belonging to the WMND clade and comprising the motif WMND (SEQ ID NO:12); (b) a protease; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Within oral care, proteases break down salivary proteins, which are adsorbed onto the tooth surface and form the pellicle that acts as attachment point for oral biofilm. Proteases may also degrade proteins that form part of the structural components of bacterial cell walls and membranes.

Proteases suitable for compositions of the invention are enzymes classified under the Enzyme Classification number (E.C.) 3.4 in accordance with the Recommendations (1992) of the International Union of Biochemistry and Molecular Biology (IUBMB)). Examples include proteases selected from those classified under the Enzyme Classification (E.C.) numbers:

- 3.4.11 (i.e. so-called aminopeptidases), including 3.4.11.5 (Prolyl aminopeptidase), 3.4.11.9 (X-pro aminopeptidase), 3.4.11.10 (Bacterial leucyl aminopeptidase), 3.4.11.12 (Thermophilic aminopeptidase), 3.4.11.15 (Lysyl aminopeptidase), 3.4.11.17 (Tryptophanyl aminopeptidase), 3.4.11.18 (Methionyl aminopeptidase);
- 3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin);
- 3.4.22 (i.e. so-called cysteine endopeptidases), including 3.4.22.2 (Papain), 3.4.22.3 (Ficain), 3.4.22.6 (Chymopapain), 3.4.22.7 (Asclepain), 3.4.22.14 (Actinidain), 3.4.22.30 (Caricain) and 3.4.22.31 (Ananain);
- 3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and
- 3.4.24 (i.e. so-called metalloendopeptidases), including 3.4.24.28 (Bacillolysin).

Examples of relevant subtilisins comprise subtilisin BPN', subtilisin amylosacchariticus, subtilisin 168, subtilisin mesentericopeptidase, subtilisin Carlsberg, subtilisin DY, subtilisin 309, subtilisin 147, thermitase, aqualysin, *Bacillus* PB92 protease, proteinase K, Protease TVV7, and Protease TW3.

Specific examples of such readily available commercial proteases include those sold under the tradenames Esperase™, Alcalase™, Neutrase™, Dyrazym™, Savinase™, Pyrase™ Pancreatic Trypsin NOVO™ (PTN), Bio-FeedC Pro™, Clear-Lens Pro™, Maxtase™, Maxacal™ Maxapem™, Opticlean™, and Purafect™.

Proteases included in compositions of the invention are further contemplated to also include variants of the above-mentioned proteases. Examples of such protease variants are disclosed in EP 130 756; EP 214 435; WO 87/04461; WO 87/05050; EP 251 446; EP 260 105; Thomas et al., (1985), *Nature* 318, pp. 375-376; Thomas et al., (1987), *J. Mol. Biol.* 193, pp. 803-81; Russel et al., (1987), *Nature* 328, p. 496-500; WO 88/08028; WO 88/08033; WO 89/06279; WO 91/00345; EP 525 610); and WO 94/02618.

The activity of proteases can be determined as described in "Methods of Enzymatic Analysis", third edition, vol. 5, 1984, Verlag Chemie, Weinheim.

Lipases

In one aspect, the present invention relates to an oral care composition comprising (a) a fructanase comprising a GH32 domain, a GH32C domain, and belonging to the WMND clade and comprising the motif WMND (SEQ ID NO:12); (b) a lipase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Within oral care, lipases target oral bacteria by degrading the lipids that form part of the structural components of bacterial cell walls and membranes.

Lipases suitable for compositions of the invention include enzymes classified under the Enzyme Classification number (E.C.) 3.1.1 (Carboxylic Ester Hydrolases) in accordance with the Recommendations (1992) of the International Union of Biochemistry and Molecular Biology (IUBMB)). Examples include lipases selected from those classified under the Enzyme Classification (E.C.) numbers 3.1.1.3 (Triacylglycerol lipases) and 3.1.1.4 (Phospholipase A2).

Examples of suitable lipases include lipases derived from the following microorganisms: *Humicola*, e.g., *H. brevispora, H. lanuginosa, H. brevis* var. *thermoidea* and *H. insolens* (U.S. Pat. No. 4,810,414); *Pseudomonas*, e.g., *Pseudomonas fragi, Pseudomonas stutzeri, Pseudomonas cepacia* and *Pseudomonas fluorescens* (WO 89/04361), or *Pseudomonas plantarii* or *Pseudomonas gladioli* (U.S. Pat. No. 4,950,417) or *Pseudomonas alcaligenes* and *Pseudomonas pseudoalcaligenes* (EP 218 272) or *Pseudomonas mendocina* (WO 88/09367; U.S. Pat. No. 5,389,536); *Fusarium*, e.g., *F. oxysporum* (EP 130,064) or *F. solani pisi* (WO 90/09446); *Mucor* (also called *Rhizomucor*), e.g., *M. miehei* (EP 238 023); Chromobacterium (especially *C. viscosum*); *Aspergillus* (especially *A. niger*); *Candida*, e.g., *C. cylindracea* (also called *C. rugosa*) or C. *Antarctica* (WO 88/02775) or *C. antarctica* lipase A or B (WO 94/01541 and WO 89/02916); Geotricum, e.g., *G. candidum* (Schimada et al., (1989), J. Biochem., 106, 383-388); *Penicillium*, e.g., *P. camembertii* (Yamaguchi et al., (1991), Gene 103, 61-67); *Rhizopus*, e.g., *R. delemar* (Hass et al., (1991), Gene 109, 107-113) or *R. niveus* (Kugimiya et al., (1992) *Biosci. Biotech. Biochem.* 56, 716-719) or *R. oryzae; Bacillus*, e.g., *B. subtilis* (Dartois et al., (1993) *Biochemica et Biophysica Acta* 1131, 253-260) or *B. stearothermophilus* (JP 64/7744992) or *B. pumilus* (WO 91/16422).

Specific examples of readily available commercial lipases include those sold under the tradenames Lipolase™, Lipolase C Ultra™, Lipozyme™, Palatase™, Novozym 435™, and Lecitase™ (Novozymes).

Examples of other lipases are Lumafast™, Ps. mendocian lipase from Genencor Int. Inc.; Lipomax™, *Ps. pseudoalcaligenes* lipase from Gist Brocades/Genencor Int. Inc.; *Fusarium solani* lipase (cutinase) from Unilever; *Bacillus* sp. lipase from Solvay Enzymes. Other lipases are available from other companies.

It is to be understood that also lipase variants are contemplated as suitable lipases for the present invention. Examples of such are described in, e.g., WO 93/01285 and WO 95/2261.

The activity of the lipase can be determined as described in "Methods of Enzymatic Analysis", Third Edition, 1984, Verlag Chemie, Weinhein, vol. 4.

Carbohydrases

In one aspect, the present invention relates to an oral care composition comprising (a) a fructanase comprising a GH32 domain, a GH32C domain, and belonging to the WMND clade and comprising the motif WMND (SEQ ID NO:12); (b) a carbohydrase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity. Preferably the carbohydrase is an alpha-amylase.

Carbohydrases may be defined as all enzymes capable of breaking down carbohydrate chains (e.g., starches) of especially five and six membered ring structures (i.e. enzymes classified under the Enzyme Classification number (E.C.) 3.2 (glycosidases) in accordance with the Recommendations (1992) of the International Union of Biochemistry and Molecular Biology (IUBMB)). Such carbohydrate structures are an important structural component of oral biofilm.

Examples include carbohydrases selected from those classified under the Enzyme Classification (E.C.) numbers:

alpha-amylase (3.2.1.1) beta-amylase (3.2.1.2), glucan 1,4-alpha-glucosidase (3.2.1.3), cellulase (3.2.1.4), endo-1,3(4)-beta-glucanase (3.2.1.6), endo-1,4-beta-xylanase (3.2.1.8), dextranase (3.2.1.11), chitinase (3.2.1.14), polygalacturonase (3.2.1.15), beta-glucosidase (3.2.1.21), alpha-galactosidase (3.2.1.22), beta-galactosidase (3.2.1.23), amylo-1,6-glucosidase (3.2.1.33), xylan 1,4-beta-xylosidase (3.2.1.37), glucan endo-1,3-beta-D-glucosidase (3.2.1.39), alpha-dextrin endo-1,6-glucosidase (3.2.1.41), sucrose alpha-glucosidase (3.2.1.48), glucan endo-1,3-alpha-glucosidase (3.2.1.59), glucan 1,4-beta-glucosidase (3.2.1.74), glucan endo-1,6-beta-glucosidase (3.2.1.75), arabinan endo-1,5-alpha-arabinosidase (3.2.1.99), lactase (3.2.1.108), chitonanase (3.2.1.132) and xylose isomerase (5.3.1.5).

Examples of relevant carbohydrases include alpha-1,3-glucanases derived from *Trichoderma harzianum*; alpha-1,6-glucanases derived from a strain of *Paecilomyces*; beta-glucanases derived from *Bacillus subtilis*; beta-glucanases derived from *Humicola insolens*; beta-glucanases derived from *Aspergillus niger*, beta-glucanases derived from a strain of *Trichoderma*; beta-glucanases derived from a strain of *Oerskovia xanthineolytica*; exo-1,4-alpha-D-glucosidases (glucoamylases) derived from *Aspergillus niger*, alpha-amylases derived from *Bacillus subtilis*; alpha-amylases derived from *Bacillus amyloliquefaciens*; alpha-amylases derived from *Bacillus stearothermophilus*; alpha-amylases derived from *Aspergillus oryzae*; alpha-amylases derived from non-pathogenic microorganisms; alpha-galactosidases derived from *Aspergillus niger*, Pentosanases, xylanases, cellobiases, cellulases, and hemi-cellulases derived from *Humicola insolens*; cellulases derived from *Trichoderma reesei*; cellulases derived from non-pathogenic mold; pectinases, cellulases, arabinases, and hemi-celluloses derived from *Aspergillus niger*, dextranases derived from *Penicillium* lilacinum; endo-glucanase derived from non-pathogenic mold; pullulanases derived from *Bacillus acidopullyticus*; beta-galactosidases derived from *Kluyveromyces fragilis*; xylanases derived from *Trichoderma reesei.*

In an embodiment of the invention the starch-modifying enzyme is a CGTase (E.C. 2.4.1.19) or a transglucosidase (2.4.1.18).

When the starch-modifying enzyme is a CGTase, it may be derived from a strain of *Bacillus autolyticus*, a strain of *Bacillus cereus*, a strain of *Bacillus circulans*, a strain of *Bacillus circulans* var. *alkalophilus*, a strain of *Bacillus coagulans*, a strain of *Bacillus firmus*, a strain of *Bacillus halophilus*, a strain of *Bacillus macerans*, a strain of *Bacillus megaterium*, a strain of *Bacillus ohbensis*, a strain of *Bacillus stearothermophilus*, a strain of *Bacillus subtilis*, a strain of *Klebsiella pneumoniae*, a strain of *Thermoanaerobacter* sp., a strain of *Thermoanaerobacter ethanolicus*, a strain of *Thermoanaerobacter finnii*, a strain of *Clostridium thermoamylolyticum*, a strain of *Clostridium thermosaccharolyticum*, or a strain of *Thermoanaerobacterium thermosulfurigenes.*

When the starch-modifying enzyme is a transglucosidase, it may be derived from *Aspergillus niger.*

In another embodiment of the invention, the oral care composition comprises a starch-hydrolyzing enzyme. This will typically be an alpha-amylase, such as a bacterial alpha-amylase, such as BAN™ or Maltogenase™, or an alpha-amylase derived from *Bacillus subtilis*; an alpha-amylase derived from *Bacillus amyloliquefaciens*; an alpha-amylase derived from *Bacillus stearothermophilus*; an alpha-amylase derived from *Aspergillus oryzae*; or an alpha-amylase derived from a non-pathogenic microorganism.

The alpha-amylase may also be a fungal alpha-amylase, such as Fungamyl™.

The starch-hydrolyzing enzyme may in another embodiment of the invention be a debranching enzyme, in particular a pullulanase (E. C. 3.2.1.41), such as Promozyme™.

In a preferred embodiment the oral care composition comprises at least one starch-modifying enzyme as defined above, in particular a CGTase, and a mutanase and/or a dextranase.

In another preferred embodiment the oral care composition of the invention comprises at least one starch-hydrolysing enzyme as defined above, in particular a bacterial alpha-amylase, and a mutanase and/or a dextranase.

The mutanase may be derived from a strain of *Trichoderma* sp., in particular *T. harzianum*, especially *T. harzianum* CBS 243.71

The dextranase may be derived from a strain of *Paecilomyces* sp., in particular *Paecilomyces lilacinus.*

Dextranases

In one aspect, the present invention relates to an oral care composition comprising (a) a fructanase comprising a GH32 domain, a GH32C domain, and belonging to the WMND clade and comprising the motif WMND (SEQ ID NO:12); (b) a dextranase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Dextranases degrade carbohydrate molecules that are important structural components of oral biofilm.

Dextranases are alpha-1,6-glucanases (also known as 1,6-alpha-D-glucan-6-glucanohydrolases) which degrade the alpha-1,6-glycosidic linkages in dextran. Several microorganisms are capable of producing dextranases, among them fungi of *Penicillium, Paecilomyces, Aspergillus, Fusarium, Spicaria, Verticillium, Helminthosporium* and the *Chaetomium* genera; bacteria of the genera *Lactobacillus, Streptococcus, Cellvibrio, Cytophaga, Brevibacterium, Pseudomonas, Corynebacterium, Arthrobacter* and *Flavobacterium*, and yeasts such as *Lipomyces starkeyi.*

Commercially available products include Dextranase™ 50 L from Novozymes produced by fermentation of strains of *Penicillium lilacium*. Dextranase 50 L is used in the sugar industry to break down dextran in raw sugar juice or syrup.

Mutanases

In one aspect, the present invention relates to an oral care composition comprising (a) a fructanase comprising a GH32 domain, a GH32C domain, and belonging to the WMND clade and comprising the motif WMND (SEQ ID NO:12); (b) a mutanase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Mutanases degrade carbohydrate molecules that are important structural components of oral biofilm.

Mutanases are −1,3-glucanases (also known as −1,3-glucanohydrolases) which degrade the −1,3-glycosidic linkages in mutan. Mutanases have been derived from *Trichoderma* (Hasegawa et al., (1969), Journal of Biological Chemistry 244, p. 5460-5470; Guggenheim and Haller, (1972), Journal of Dental Research 51, p. 394-402) and from strains of *Streptomyces* (Takehara et al., (1981), Journal of Bacteriology 145, p. 729-735), *Cladosporium resinae* (Hare et al. (1978), Carbohydrate Research 66, p. 245-264), *Pseudomonas* sp. (U.S. Pat. No. 4,438,093), *Flavobacterium* sp. (JP 77038113), *Bacillus circulans* (JP 63301788) and *Aspergillus* sp. A mutanase gene from *Trichoderma harzianum* has been cloned and sequenced (Japanese Patent No. 4-58889/A).

A mutanase suitable for the use in an oral care composition of the invention may be produced by filamentous fungi from the group including *Trichoderma*, in particular from a strain of *Trichoderma harzianum*, such as *Trichoderma harzianum* CBS 243.71 (mature polypeptide disclosed herein as SEQ ID NO:11), or *Penicillium*, in particular a strain of *Penicillium funiculosum*, such as *Penicillium funiculosum* NRRL 1768, or a strain of *Penicillium lilacinum*, such as *Penicillium lilacinum* NRRL 896, or a strain of *Penicillium purpurogenum*, such as the strain of *Penicillium purpurogenum* CBS 238.95, or a strain of the genus *Pseudomonas*, or a strain of *Flavobacterium* sp., or a strain of *Bacillus circulans* or a strain of *Aspergillus* sp., or a strain of *Streptomyces* sp.

The mutanase may also be derived from *Penicillium purpurogenum.*

U.S. Pat. No. 4,353,981 (Guggenheim et al.) discloses the use of the *Trichoderma harzianum* CBS 243.71 mutanase (mature polypeptide disclosed herein as SEQ ID NO: 11), the *Penicillium funiculosum* NRRL 1768 mutanase and the *Penicillium lilacinum* NRRL 896 mutanase for the removal of dental plaque.

In one embodiment, the mutanase is obtainable from *Trichoderma*, e.g., obtainable from *Trichoderma harzianum*, and has a sequence identity of at least 60%, e.g., at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, to SEQ ID NO:11, and has mutanase activity. In a preferred embodiment, the mutanase differs by up to 10 amino acids, e.g., 1, 2, 3, 4, 5, 6, 7, 8, 9, or 10, from the polypeptide shown in SEQ ID NO:11. In a preferred embodiment, the mutanase comprises, consists essentially of, or consists of SEQ ID NO:11.

Oxidoreductases

In one aspect, the present invention relates to an oral care composition comprising (a) a fructanase comprising a GH32 domain, a GH32C domain, and belonging to the WMND clade and comprising the motif WMND (SEQ ID NO:12); (b) an oxidoreductase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity. Preferably the oxidoreductase is a laccase or a related enzyme, an oxidase, or a peroxidase.

Oxidoreductases are enzymes catalyzing oxidoreductions, and they have been found to bleach teeth. They are classified under the Enzyme Classification number (E.C.) 1 (Oxidoreductases) in accordance with the Recommendations (1992) of the International Union of Biochemistry and Molecular Biology (IUBMB).

According to the present invention, three types of oxidoreductases are especially contemplated: 1) laccases or related enzymes such as tyrosinase that act on molecular oxygen ($O_2$) and yield water ($H_2O$) without any need for peroxide (e.g. $H_2O_2$); 2) oxidases that act on molecular oxygen ($O_2$) and yield peroxide ($H_2O_2$); and 3) peroxidases that act on peroxide (e.g., $H_2O_2$) and yield water ($H_2O$).

Preferred oxidoreductases are of microbial origin, especially recombinant and/or substantially purified enzymes without any side activity. Microbial enzyme means in the context of the present invention enzymes derived from bacteria, filamentous fungi or yeasts.

In the case of an enzyme acting on oxygen ($O_2$) as the acceptor, said oxygen may be molecular oxygen supplied by the air.

Enzyme systems which comprise a combination of the three types of enzymes are also contemplated as being suitable for compositions of the invention. The enzyme systems may, e.g., consist of a laccase or a related enzyme and an oxidase; a laccase or a related enzyme and a peroxidase; a laccase or a related enzyme and an oxidase and a peroxidase; or an oxidase and a peroxidase.

Laccases and Related Enzymes

In one aspect, the present invention relates to an oral care composition comprising (a) a fructanase comprising a GH32 domain, a GH32C domain, and belonging to the WMND clade and comprising the motif WMND (SEQ ID NO:12); (b) a laccase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Examples of suitable enzymes within the group of laccases and related enzymes are those capable of oxidizing volatile sulphur compounds (VSCs) and nitrogen compounds in question are mono- and diphenolicoxidases, such as catechol oxidase (1.10.3.1), laccase (E.C. 1.10.3.2), tyrosinase (E.C. 1.14.18.1), and bilirubin oxidase (E.C. 1.3.3.5).

Laccase oxidizes o-diphenol as well as p-diphenol forming their corresponding quinones. Tyrosinase and catechol oxidase catalyzes the hydroxylation of monophenols in o-diphenols and the oxidation of o-diphenols in o-quinones.

Laccase is usually applied together with a suitable donor, preferably chlorogenic acid.

Laccases suitable for compositions of the invention may be derived from a strain of *Polyporus* sp., in particular a strain of *Polyporus pinsitus* (also called *Trametes villosa*) or *Polyporus versicolor*, or a strain of *Myceliophthora* sp., e.g., *M. thermophila* or a strain of *Rhizoctonia* sp., in particular a strain of *Rhizoctonia praticola* or *Rhizoctonia solani*, or a strain of *Scytalidium* sp., in particular *S. thermophilium*, or a strain of Pyricularia sp., in particular Pyricularia *oryzae*, or a strain of *Coprinus* sp., such as a *C. cinereus*. The laccase may also be derived from a fungus such as *Collybia, Fornes, Lentinus, Pleurotus, Aspergillus, Neurospora, Podospora, Phlebia*, e.g., *P. radiata* (WO 92/01046), *Coriolus* sp., e.g., *C. hirsitus* (JP 2-238885), and *Botrytis.*

In a preferred embodiment of the invention the laccase is derived from a strain of *Myceliophthora* sp., especially the *Myceliophthora thermophila* laccase described in WO 1995/33836.

Bilirubin oxidase may be derived from a strain of *Myrothecium* sp., such as a strain of M. verrucaria.

Peroxidases

In one aspect, the present invention relates to an oral care composition comprising (a) a fructanase comprising a GH32 domain, a GH32C domain, and belonging to the WMND clade and comprising the motif WMND (SEQ ID NO:12); (b) a peroxidase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Peroxidases must be used in combination with either $H_2O_2$ or an oxidase to obtain the desired result, i.e., removal or at least reduction of malodor.

Suitable peroxidases can be found within the group of enzymes acting on peroxide as acceptor, e.g., E.C. 1.11.1, especially peroxidase (E.C. 1.11.1.7).

Specific examples of suitable enzymes acting on peroxide as acceptor include peroxidases derived from a strain of the fungus species *Coprinus*, in particular a strain of *Coprinus cinereus* or *Coprinus macrorhizus*, or derived from a strain of the bacteria genus *Bacillus*, in particular a strain of *Bacillus pumilus.*

Haloperoxidases are also suitable according to the invention. Haloperoxidases form a class of enzymes which are able to oxidize halides, i.e., chloride, bromide, and iodide, in the presence of hydrogen peroxide to the corresponding hypohalous acids. A suitable haloperoxidase is derivable from *Curvularia* sp., in particular *C. verruculosa.*

Oxidases

In one aspect, the present invention relates to an oral care composition comprising (a) a fructanase comprising a GH32 domain, a GH32C domain, and belonging to the WMND clade and comprising the motif WMND (SEQ ID NO:12); (b) an oxidase; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Oxidases yielding peroxide ($H_2O_2$) must be used in combination with a peroxidase to be able to remove or at least reduce malodor. Suitable oxidases include glucose oxidase (E.C. 1.1.3.4), hexose oxidase (E.C. 1.1.3.5), L-amino-acid oxidase (E.C. 1.4.3.2), xylitol oxidase, galactose oxidase (E.C. 1.1.3.9), pyranose oxidase (E.C. 1.1.3.10), alcohol oxidase (E.C. 1.1.3.13).

If a L-amino acid oxidase is used, it may be derived from a *Trichoderma* sp. such as *Trichoderma harzianum*, such as the L-amino acid oxidase described in WO 1994/25574, or *Trichoderma viride.*

A suitable glucose oxidase may originate from *Aspergillus* sp., such as a strain of *Aspergillus niger*, or from a strain of *Cladosporium* sp. in particular *Cladosporium oxysporum.*

Hexose oxidases from the red seaweed Chondrus *crispus* (commonly known as Irish moss) (Sullivan and Ikawa, (1973), *Biochim. Biophys. Acta* 309, p. 11-22; Ikawa, (1982), Meth. in Enzymol. 89, Carbohydrate Metabolism Part D, 145-149) oxidizes a broad spectrum of carbohydrates, such as D-glucose, D-galactose, maltose, cellobiose, lactose, D-glucose 6-phosphate, D-mannose, 2-deoxy-D-glucole, 2-deoxy-D-galactose, D-fucose, D-glucuronic acid, and D-xylose.

The red seaweed *Iridophycus flaccidum* produces easily extractable hexose oxidases, which oxidize several different mono- and disaccharides (Bean and Hassid, (1956), *J. Biol. Chem* 218, p. 425; Rand et al. (1972), *J. Food Science* 37, p. 698-710).

Another suitable group of enzymes is xylitol oxidase (disclosed in JP 80892242) which oxidizes xylitol, D-sorbitol, D-galactitol, D-mannitol and D-arabinitol in the presence of oxygen. A xylitol oxidase can be obtained from strains of *Streptomyces* sp. (e.g., *Streptomyces* IKD472, FERM P-14339). Said enzyme has a pH optimum at 7.5 and is stable at pH 5.5 to 10.5 and at temperatures up to 65° C.

Lysozymes

In one aspect, the present invention relates to an oral care composition comprising (a) a fructanase comprising a GH32 domain, a GH32C domain, and belonging to the WMND clade and comprising the motif WMND (SEQ ID NO:12); (b) a lysozyme; and (c) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Lysozymes suitable for compositions of the present invention include those classified under EC 3.2.1.17. Lysozyme is also known as muramidase and occurs naturally in many organisms such as viruses, plants, insects, birds, reptiles, and mammals. In mammals, lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms. Due to its ability to degrade bacterial peptidoglycans, lysozyme functions as an antibacterial agent.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have recently been identified in fungi. The lysozyme family GH25 has been found to be structurally unrelated to the other lysozyme families. Lysozyme extracted from hen egg white is the primary product available on the commercial market.

For the compositions of the present invention, preferred lysozymes may be selected from GH22 lysozymes, GH23 lysozymes, GH24 lysozymes, GH73 lysozymes, and GH25 lysozymes. Preferably, the lysozyme is a GH25 lysozyme. Examples of GH25 lysozymes can be found in, e.g., WO 2013/076253, WO 2005/080559, PCT/CN2017/117753, and PCT/CN2017/117765.

Oral Care Ingredients and Formats

The oral care compositions of the invention comprise (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

The oral care ingredients may be varied according to the type of oral care composition as well as the desired characteristics and/or activities of the oral care compositions. For the purpose of the present invention, the terms "ingredient" and "component" are used interchangeably in relation to oral care compositions.

An oral care composition of the invention may be an internal oral care composition such as toothpaste, dental cream, mouthwash, mouth rinse, lozenges, pastilles, chewing gum, confectionary, candy, and the like, which is designed to remove biofilm inside the oral cavity, e.g., biofilm residing on teeth, on soft tissues of the oral cavity, and on dentures residing in the oral cavity.

An oral care composition of the invention may also be an external oral care composition such as denture cleaning solution, denture cleaning tablet, denture cleaning powder, and the like, which is designed to remove biofilm from dentures that have been removed from the oral cavity for cleaning.

In a preferred embodiment, the oral care composition is an internal oral care composition, and the at least one oral care component is selected from the group consisting of abrasives, humectants, solvents, thickening agents, binding agents, buffering agents, foaming agents, foaming modulators, sweetening agents, softening agents, plasticizing agents, flavoring agents, coloring agents, therapeutic agents, anti-microbial agents, tartar-controlling agents, fluoride sources, preservatives, detergents, surfactants, coloring agents, buffering agents, softeners, plasticizers, whitening agents, bleaching agents, gum-base ingredients, and bulking agents.

Although the oral care ingredients mentioned herein are categorized by a general header according to a functionality, this is not to be construed as a limitation, as an ingredient may comprise additional functionalities as will be appreciated by the skilled person.

Toothpaste, Dental Cream, Mouthwash, and Mouth Rinse

Internal oral care compositions of the invention in the form of toothpaste, dental cream, mouthwash, and mouth rinse may include ingredients and/or substances selected from the following categories:

| Type of ingredient | Examples | Amount (weight %) |
|---|---|---|
| Abrasives | Calcium Carbonate, Sodium bicarbonate, Diatomite, Charcoal, Dicalcium phosphate dehydrate, Hydrated Silica, Hydrated Alumina | 0 to 70% |
| Humectants | Glycerol, sorbitol and propylene glycol | 0 to 80% |
| Solvents | Water, ethanol, water/ethanol mixtures | 0.001 to 95% |
| Thickening/binding agents | Xanthan gum, cellulose gum (sodium carboxymethyl cellulose), hydroxyethyl cellulose, carrageenan, glycerin, potassium thiocyanate, PVM/MA copolymer, carbomer, arrowroot powder | 0.01 to 20% |
| Buffering agents | Sodium Hydroxide, Sodium phosphate, Di- and trisodium phosphate, Sodium Citrate, Calcium Glycerophosphate, | 0.001 to 10% |
| Formulation and foaming agents (detergents, surfactants) | Sodium lauryl sulfate (SLS), sodium lauryl sarcosinate, sodium lauroyl glutamate, sodium methyl cocoyl taurate, Steareth-30, coco-glucoside, propylene glycol (1,2-propanediol), Poloxamer 407, Polysorbate 20, Polysorbate 80 | 0.001 to 10% |
| Foaming agents/modulators | PEG's (polyethylene glycols) | 0.001 to 10% |
| Sweetening agents | Xylitol, Sorbitol, Erythritol, mannitol, Sodium Saccharin, Maltitol, Stevia, Sucralose, Acesulfame K, aspartame, Hydrogenated Starch Hydrolysate | 0.001 to 60% |
| Softener/plasticizer | Lecithin, Hydrogenated vegetable oils, Glycerol ester, Lanolin, Methyl ester, Pentaerythritol ester, Stearic Acid, sodium and Potassium Stearates | 0.001 to 5% |
| Flavoring agents | Peppermint oil, spearmint oil | 0.001 to 5% |
| Coloring agents | Titanium dioxide, beta-carotene, FD&C Blue 1 Aluminum Lake, FD&C Blue 2 Lake, FD&C Yellow 5 Aluminum Lake, FD&C Yellow 5 | 0.001 to 20% |

-continued

| Type of ingredient | Examples | Amount (weight %) |
|---|---|---|
| Enzymes | DNases, dispersins, proteases, lipases, carbohydrases, dextranases, mutanases, oxidoreductases, laccases, peroxidases, oxidases, and lysozymes | 0.001 to 20% |
| Preservatives | Sodium Benzoate, Methyl Paraben, Ethyl Paraben, Citric acid, Potassium Sorbate, Calcium Citrate, Propylene glycol | 0.001 to 30% |
| Whitening/bleaching agents | Hydrogen peroxide, sodium hypochlorite, sodium perborate | 0.01 to 10% |
| Therapeutic agents (including anti-bacterial, anti-carries, anti-inflammatory agents) | Calcium Fluoride, Sodium Fluoride, Triclosan, Alcohol, various essential oils (Thymol, Menthol), Benzoic acid, Sodium benzoate, zinc Gluconate, Aloe Vera, chloride, cetylpyridinuim chloride, Domiphen bromide, Methyl salicylate, Chlorhexidine digluconate | 0.001 to 50% |

Toothpaste

Toothpastes and dental creams/gels typically include abrasives, solvents, humectants, detergents/surfactants, thickening and binding agents, buffering agents, flavoring agents, sweetening agents, fluoride sources, therapeutic agents, enzymes, coloring agents, and preservatives.

In a preferred embodiment, the present invention relates to oral care compositions in the form of a toothpaste or dental cream comprising (a) a fructanase comprising a GH32 domain, a GH32C domain, and belonging to the WMND cade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity, and wherein the at least one oral care ingredient is selected from the following ingredients:

| Type of ingredient | Examples | Amount (weight %) |
|---|---|---|
| Abrasive | Calcium carbonate, sodium bicarbonate, hydrated silica, hydrated Alumina | 10 to 50% |
| Solvent | Water | 5 to 40% |
| Humectant | Glycerin and sorbitol | 20 to 70% |
| Detergent/ Surfactant | Sodium lauryl sulphate (SLS), sodium lauryl sarcosinate, cocamidopopybetaine and steareth-30 | 1 to 3% |
| Thickening and binding agent | Natural gums (e.g. xanthan gum, cellulose gum) or synthetic polymers (e.g., PVM/MA copolymer, carbomer). hydroxyethyl cellulose, carrageenan, glycerin. | 1 to 2% |
| Buffering agent | Sodium citrate, calcium glycerophosphate, sodium hydroxide, di- and trisodium pyrophosphate, disodium phosphate | 1 to 60% |
| Flavoring agent | Peppermint oil, spearmint oil | 0 to 2% |
| Sweetening agent | Xylitol, sorbitol, erythritol, saccharin, stevia, sucralose | 0 to 2% |
| Fluoride source | Sodium fluoride, calcium fluoride, stannous fluoride, sodium monofluorophosphate | 0.001 to 10% |
| Therapeutic agent | Triclosan, zinc gluconate, aloe vera extracts, chloride, cetylpyridinuim chloride, domiphen bromide, methyl salicylate, chlorhexidine, chlorhexidine digluconate | 0.001 to 50% |
| Enzyme | DNases, dispersins, proteases, lipases, carbohydrases, dextranases, mutanases, oxidoreductases, laccases, peroxidases, oxidases, and lysozymes | 0.001 to 20% |
| Coloring agent | Titanium dioxide | 0 to 0.5% |
| Preservative | Sodium gluconate, citric acid, sodium benzoate | 0.05 to 0.5% |

An oral care composition of the invention may be a toothpaste comprising the following ingredients (in weight % of the final toothpaste composition):

Abrasive: 10 to 70%

Humectant: 0 to 80%

Thickening agent: 0.1 to 20%

Binding agent: 0.01 to 10%

Sweetening agent: 0.1 to 5%

Foaming agent: 0 to 15%

Fructanase: 0.01 to 10%

Other enzyme(s) with action(s) on oral cavity: 0.01 to 20%

Mouthwash

Mouthwashes and mouth rinses of the invention, including plaque removing liquids, typically comprise a fructanase, a carrier liquid, detergents/surfactants, buffering agents, flavoring agents, humectants, sweetening agents, therapeutic agents, fluoride sources, coloring agents, preservatives, and enzymes.

In a preferred embodiment, the present invention relates to oral care compositions in the form of a mouthwash or mouth rinse comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity; and wherein the at least one oral care ingredient is selected from the following ingredients:

| Type of ingredient | Example |
|---|---|
| Carrier liquid, usually 60-99% | Water, ethanol (18-27%), water/ethanol mixture |
| Detergent/surfactant | Poloxamer 407, Polysorbate 20, Polysorbate 80, Steareth-30 |
| Buffering agent | Sodium Hydroxide, (Di)-Sodium phosphate, Sodium citrate, Benzoic acid, Sodium Benzoate |
| Flavoring agent | Peppermint oil, spearmint oil |
| Humectants | Glycerin, Sorbitol |
| Sweetening agents | Saccharin, Xylitol |
| Therapeutic agent | Triclosan, zinc gluconate, aloe vera extracts, chloride, cetylpyridinuim chloride, domiphen bromide, methyl salicylate, chlorhexidine, chlorhexidine digluconate |
| Fluoride source | Sodium fluoride, calcium fluoride, stannous fluoride, or sodium monofluorophosphate |
| Coloring agent | Titanium oxide |
| Preservative | Sodium Benzoate, Benzoic acid, Citric acid, Propylene glycol |
| Enzyme | Dispersins, proteases, lipases, carbohydrases, dextranases, mutanases, oxidoreductases, laccases, peroxidases, oxidases, and lysozymes |

An oral care composition of the invention may be a mouthwash comprising the following ingredients (in weight % of the final mouthwash composition):

Water: 0 to 70%

Ethanol: 0 to 20%

Humectant: 0 to 20%

Surfactant: 0 to 2%

Fructanase: 0.01 to 10%

Enzyme(s) with action(s) on oral cavity: 0.01 to 20%

Other ingredients: 0 to 2% (e.g., flavors, sweeteners, fluoride sources).

The mouthwash composition may be buffered with an appropriate buffer, e.g., sodium citrate or phosphate in the pH range 6-7.5.

Relevant oral care components suitable for toothpastes, dental creams, mouthwashes, and mouth rinses is further detailed below. The skilled person is capable of varying the oral care components according to the type of oral care composition as well as the desired characteristics and/or activities of the specific oral care composition. An oral care composition may not necessarily comprise all of the mentioned ingredients.

Abrasives

Abrasive polishing material might be incorporated into the oral care composition of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, bentonite, silicium dioxide, sodium bicarbonate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels, and the like.

Also suitable as abrasive agents are calcium pyrophosphate, water-insoluble alkali metaphosphates, poly-metaphosphates, dicalcium phosphate and/or its dihydrate, dicalcium orthophosphate, tricalcium phosphate, particulate hydroxyapatite, and the like. It is also possible to employ mixtures of these substances.

Silica dental abrasives of various types are preferred because of their unique benefits of exceptional dental cleaning and polishing performance without unduly abrading tooth enamel or dentine and which have a good compatibility with other possible ingredients, like metal ions and fluoride.

Dependent on the oral care composition, the abrasive product may be present in from 0 to 70% by weight, preferably from 1% to 70%.

For toothpastes the abrasive material content typically lies in the range of from 10% to 70% by weight of the final tooth-paste product.

Humectants

Humectants are employed to prevent loss of water from, e.g., toothpastes and to avoid hardening of toothpastes upon exposure to air. Some humectants also give a desirable sweetness of flavor to toothpaste and mouthwash compositions. Suitable humectants for use in oral care compositions according to the invention include the following compounds and mixtures thereof: glycerol, polyol, sorbitol, xylitol, maltitol, lactitol, polyoxyethylene, polyethylene glycols (PEG), polypropylene glycols, propylene glycol, 1,3-propanediol, 1,4-butanediol, hydrogenated partially hydrolyzed polysaccharides and the like, coconut fatty acid, amide of N-methyl-taurine, and Pluronic®.

Humectants are in generally present in from 0% to 80%, preferably 5 to 70% by weight.

Thickening/Binding Agents

Suitable thickening and/or binding agents include silica, starch, tragacanth gum, xanthan gum, karaya gum, carrageenans (extracts of Irish moss), gum arabic, alginates, pectin, cellulose derivatives, such as hydroxyethyl cellulose, sodium carboxymethyl cellulose, hydroxypropyl cellulose and hydroxyethyl propyl cellulose, polyacrylic acid and its salts, polyvinylpyrrolidone and carboxyvinyl polymers, as well as inorganic thickeners such as amorphous silica compounds. These agents stabilize the oral care compositions of the invention.

Thickeners may be present in toothpaste, dental creams and gels as well as in mouthwashes in an amount of from 0.1 to 20% by weight, and binders to the extent of from 0.01 to 10% by weight of the final product.

Foaming Agents and Foaming Modulators

As foaming agent soap, anionic, cationic, non-ionic, amphoteric and/or zwitterionic surfactants can be used, either alone or in combinations. These may be present at levels of from 0% to 15%, preferably from 0.1% to 13%, more preferably from 0.25% to 10% by weight of the final product. Surfactants are only suitable to the extent that they do not exert an inactivation effect on the enzymes and other components included in the oral care composition. Useful surface-active agents include anionic, nonionic, and ampholytic compounds, with anionic compounds being preferred.

Examples of suitable surfactants include salts of the higher alkyl sulfates, such as sodium lauryl sulfate or other suitable alkyl sulfates having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isotopic acid or with glycerol monosulfate; such as the sodium salt of monosulfated monoglyceride of hydrogenated coconut oil fatty acids; salts of olefin sulfonates, e.g., alkene sulfonates or alkene sulfonates or mixtures thereof having 12 to 16 carbon atoms in the carbon chain of the molecule; and soaps of higher fatty acids, such as those of 12 to 18 carbon atoms, e.g., coconut fatty acids.

The cation of the salt may be sodium, potassium or mono-, di or triethanol amine. The nonionic surfactants include sucrose/fatty acid esters, maltose/fatty acid esters, maltitol/fatty acid esters, maltotriitol/fatty acid esters, maltotetraitol/fatty acid esters, maltopentaitol/fatty acid esters, maltohexaitol/fatty acid esters, mahoheptaitol/fatty acid esters, sorbitan/fatty acid esters, lactose/fatty acid esters, lactinose/fatty acid esters, polyoxyethylene/polyoxypropylene copolymers, polyoxyethylene alkyl ethers, polyoxyethylene/fatty acid esters, fatty acid alkanolamides, polyoxyethylene sorbitan/fatty acid esters, polyoxyethylene/hydrogenated castor oil, and polyglycerin/fatty acid esters.

Most preferred are sodium lauryl sulphate, sodium dodecylbenzene sulphonate and sodium lauryl sarcosinate.

Preferred foaming modulators include polyethylene glycols.

Foaming agents and foaming modulators may be present from in an amount of from 0% to 15% by weight, preferably from 0.01% to 10% by weight.

Sweetening Agents

Suitable sweeteners include, but are not limited to, saccharin and water-soluble salts thereof, dextrose, sucrose, lactose, maltose, levulose, aspartame, cyclamate salts, D-tryptophan, dihydrochalchones, acesulphame, stevioside, levaudioside, glycyrrhizins, pellartine, thaumatin, p-methoxycinnamic aldehyde, hydrogenated starch hydrolysates, xylitol, sorbitol, erythritol, mannitol, and mixtures thereof.

Sweeteners may be present from in an amount of from 0.001% to 60% by weight, preferably from 0.01% to 50% by weight.

Flavoring Agents

Flavoring agents are usually present in low amounts, such as from 0.01% to about 5% by weight, especially from 0.1% to 5%. The flavors that may be used in the invention include, but are not limited to, wintergreen oil, peppermint oil, spearmint oil, clove bud oil, menthol, anethole, methyl salicylate, eucalyptol, cassia, 1-inenthvl acetate, sage, eugenol, parsley oil, oxanone, alpha-irisone, marjoram, lemon, orange, cranberry, propenyl guaethol, cinnamon, vanillin, ethyl vanillin, heliotropine, 4-cis-heptenal, diacetyl, methylpara-tert-butyl phenyl acetate, carvone, cineole, menthone, cinnamic aldehyde, limonene, ocimene, n-decyl alcohol, citronellol, alpha-terpineol, methyl acetate, citronellyl acetate, methyl eugenol, linalool, thymol, rosemary oil, pimento oil, diatomaceous oil, *eucalyptus* oil, and mixtures thereof.

Coolants may also be part of the flavor system or added separately to the composition. Preferred coolants in the present compositions are the paramenthan carboxyamide agents such as N-ethyl-p-menthan-3-carboxamide (known commercially as 'WS-3"), menthol, 3-1-menthoxypropane-1,2-diol ("TK-10"), menthone glycerol acetal ("MGA"), menthyl lactate and mixtures thereof.

Whitening/Bleaching Agents

Whitening/bleaching agents include $H_2O_2$ and may be added in amounts less than 5%, preferably from 0.05 to 4%, calculated on the basis of the weight of the final composition.

Other bleaching components which might be comprised by the present invention include, peroxydiphosphate, urea, peroxide, metal peroxides such as calcium peroxide, sodium peroxide, stronthium peroxide, magnesium peroxide, hypochlorite salts such as sodium hypochlorite, and the salts of perborate, persilicate, perphosphate and percarbonate such as sodium perborate, potassium persilicate and sodium percarbonate. The peroxide compounds can be stabilized by addition of a triphenylmethane dye, a chelating agent or antioxidants such as butylated hydroxy anisole (BHA) or butylated hydroxy toluene (BHT).

Solvent

A solvent is usually added to compositions of the invention in an amount sufficient for giving the compositions a flowable form in case the compositions is; e.g., a tooth paste, dental cream or gel, or to dissolve the other components of a compositions, in case of, e.g., a mouthwash or mouth rinse.

Suitable solvents include water, ethanol and water/ethanol mixtures, which may be present in an amount of from 0.1% to 70%.

Anti-Microbial Agents

The present invention also includes water-soluble anti-microbial agents, such as chlorhexidine, triclosan, digluconate, hexetidine, alexidine, quaternary ammonium antibacterial compounds, and water-soluble sources of certain metal ions such as zinc, copper, silver and stannous (e.g., zinc, copper and stannous chloride, and silver nitrate) may also be included.

Sparingly soluble zinc salts such as zinc citrate, zinc C14-alkyl maleate, zinc benzoate, zinc caproate, zinc carbonate might also be included used in the compositions of the present invention to prolong the anti-microbial effectiveness of zinc ions due to the slow dissolution of these zinc salts in saliva.

Anti-microbial agents may be present in an amount of from 0% to 50% by weight, preferably from 0.01% to 40% by weight, most preferably from 0.1% to 30% by weight.

Tartar-Controlling Agent

Compositions of the invention may comprise a tartar-controlling agent such as inorganic phosphorous tartar-controlling agents including any of the pyrophosphates such as disodium pyrophosphate, dipotassium pyrophosphate, tetrapotassium pyrophosphate, tetrasodium pyrophosphate, and mixtures thereof.

Organic phosphorous compounds that may serve as tartar-controlling agents include polyphosphonates such as disodium ethane-1-hydroxy-1, 1-diphosphonate (EHDP), methanediphosphonic acid, and 2-phosphonobutane-1 2,4-tricarboxylic acid.

Tartar-controlling agents may be present in an amount of from 0% to 10% by weight, preferably from 0.1% to 5% by weight.

Preservatives

Suitable preservatives include sodium benzoate, potassium sorbate, p-hydroxybenzoate esters, methyl paraben, ethyl paraben, propyl paraben, citric acid, calcium citrate, and mixtures thereof.

Preservatives may be present in an amount of from 0% to 40% by weight, preferably from 0.01% to 30% by weight.

Fluoride Sources

Compositions of the invention may also comprise ingredients that can be used as fluoride source. Preferred soluble fluoride sources include sodium fluoride, potassium fluoride, stannous fluoride, indium fluoride, sodium monofluorophosphate, sodium hexafluorosilicate, zinc fluoride, lithium fluoride, aluminum fluoride, acidulated phosphate fluoride, ammonium bifluoride, titanium tetrafluoride, and amine fluoride.

Especially preferred are sodium fluoride and sodium monofluorophosphate.

Fluoride sources may be present in an amount of from 0% to 20% by weight, preferably from 0.01% to 15% by weight, most preferably from 0.1% to 10% by weight.

In a preferred embodiment, the at least one oral care ingredient is a fluoride source; preferably the fluoride source is selected from the group consisting of sodium fluoride, calcium fluoride, stannous fluoride, or sodium monofluorophosphate Coloring Agents Coloring agents or pigments suitable for oral care compositions of the invention include non-toxic, water-insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green No. 1 lake, FD&C Blue No. 2 lake, FD&C Red No. 30 lake, FD&C Yellow No. 16 lake, and FD&C Yellow No. 10.

A preferred opacifier is titanium dioxide.

Coloring agents may be present in an amount of from 0% to 20% by weight, preferably from 0.01% to 15% by weight, most preferably from 0.1% to 10% by weight.

Buffering Agents

The oral care compositions of present invention may also include buffering agents, i.e., pH-adjusting agents, such as alkali metal hydroxides, carbonates, sesquicarbonates, borates, silicates, phosphates, imidazole, and mixtures thereof.

Specific buffering agents include monosodium phosphate, trisodium phosphate, sodium hydroxide, potassium hydroxide, alkali metal carbonate salts, sodium carbonate, imidazole, pyrophosphate salts, sodium citrate, hydrochloric acid, sodium hydroxide, triethanolamine, triethylamine, lactic acid, malic acid, fumaric acid, tartaric acid, phosphoric acid and mixtures of these.

Buffering agents may be present in an amount of from 0% to 10% by weight, preferably from 0.01% to 5% by weight.

Chewing Gum

When the oral composition according to the invention is a chewing gum, it can be any known type of chewing gum, such as chewing gum pieces optionally coated, as well as sticks or chewing gum provided with an arbitrary desired shape in response to the intended use. The chewing gum preparation can be of any quality including the bubble gum quality.

In a preferred embodiment, the present invention relates to oral care compositions in the form of a chewing gum comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity; and wherein the at least one oral care ingredient is selected from elastomer, softening agent, plasticizing agent, emulsifier, wax, coloring agent, sweetening agent, flavoring agent, bulking agent, and thickening agent.

Gum Base Ingredients

Chewing gum is traditionally considered as being comprised of a water-insoluble or base portion and a water-soluble portion that contains flavoring agents, sweetening agents, and coloring agents. The gum base part of the gum is a masticatory substance which imparts the chew characteristics to the final product. It defines the release profile of flavors and the sweeteners and plays a significant role in the gum product. The flavors, sweeteners and colors can be thought of as providing the sensory appeal aspects of the chewing gum. No limitations as to the chewing gum bases used in a chewing gum preparation according to the invention exist. Conventional chewing gum bases available for instance from Dansk Tyggegummi Fabrik A/S, L.A. Dreyfus or Cafasa Gum SIA, are usually suitable, but specially made formulations can also be used. The formulation depends on the desired type of chewing gum or the desired type of structure. Suitable raw materials for gum bases include the substances according to the U.S. Chewing Gum Base Regulations—Code of Federal Regulations, Title 21, Section 172,615 and in accordance with other national and international lists (or positive lists) and include elastomers, resins, waxes, polyvinyl acetates, oils, fats, emulsifiers, fillers and antioxidants.

The gum base usually comprises from 15 to 90% by weight, preferably from 30 to 40% by weight, more preferably from 5 to 25% of the final product.

Elastomers provide the chew, springiness or bounce to the base and control bubble and flavor release in the final chewing gum. They may be any water-insoluble polymer known in the art. They include styrene butadiene copolymers (SBR) and non-SBR types, both natural and synthetic. Examples of natural elastomers include, without limitation, rubbers such as rubber latex (natural rubber) and guayule, and gums such as chicle, jelutong, balata, guttapercha, lechi capsi, sorva, crown gum, nispero, rosidinha, perillo, niger gutta, tunu, gutta kay, pendare, leche de vaca, chiquibul, crown gum, and the like, and mixtures thereof. Examples of synthetic elastomers include, without limitation, polyisobutylene, isobutylene-isoprene copolymers (butylrubber), polyethylene, polybutadiene, styrenebutadiene copolymers, polyisoprene, and the like, and mixtures thereof.

The amounts of elastomer (rubbers) employed in the gum base composition will vary greatly depending upon various factors such as the, type of gum base used (adhesive, or conventional, bubble or standard) the consistency of the gum base composition desired, and the other components used in the composition to make the final chewing gum product. In general, the elastomer is present in the gum base composition in an amount of from about 15% to about 60%, preferably from about 25% to about 30%, by weight based on the total weight of the gum base composition.

Elastomer solvents aid in softening or plasticizing the elastomer component. In doing so they provide a bulkiness to the chew.

Elastomer solvents include, but are not limited to, natural rosin esters and synthetic derivatives of, e.g., terpenes. Examples of elastomer solvents suitable for use herein include tall oil rosin ester; partially hydrogenated wood and gum rosin; the glycerol esters of wood and gum rosin, partially hydrogenated wood/gum rosin, partially dimerized wood and gum rosin, polymerized wood and gum rosin, and tall oil rosin; the deodorized glycerol ester of wood rosin; the pentaerythritol esters of wood and gum rosin; partially hydrogenated wood and gum rosin; the methyl ester of partially hydrogenated wood rosin; methyl, glycerol and pentaerythritol esters of rosins and modified rosins such as hydrogenated, dimerized and polymerized rosins; terpene resins such as polymers of alpha-pinene or beta-pinene, terpene hydrocarbon resins; polyterpene; and the like, and mixtures thereof. The elastomer solvent may be employed in the gum base composition in an amount of from about 2% to about 40%, and preferably from about 7% to about 15% by weight of the gum base composition.

Polyvinyl acetates provide stretch or elasticity to the gum base. They also affect chew bulkiness, softness and bubble, hydrophilic character and flavor release.

The amounts of the different molecular weight polyvinyl acetates present in the gum base composition should be effective to provide the finished chewing gum with the desired chew properties, such as integrity, softness, chew bulkiness, film-forming characteristic, hydrophilic character, and flavor release. The total amount of polyvinyl acetate used in the gum base composition is usually from about 45% to about 92% by weight based on the total gum base composition. The vinyl polymers may possess a molecular weight ranging from about 2000 Da up to about 95,000 Da.

Typically, the low molecular weight polyvinyl acetate has a weight average molecular weight of from about 2,000 Da to about 14,000 Da. The medium molecular weight polyvinyl acetate typically has a weight average molecular weight of from about 15,000 Da to 55,000 Da. The high molecular weight polyvinyl acetate typically has a weight average molecular weight of from 55,000 Da to about 95,000 Da but may range as high as 500,000 Da.

Waxes, fats, and oils plasticize the elastomer mixture and improve the elasticity of the gum base. Waxes can provide a soft or firm chew, affect the flavor release and provide bulkiness and smoothness to the gum base. Fats and oils provide a soft chew. The fats, oils and waxes may be use individually or in combination or the gum base may be a wax free gum base.

Waxes when used, may be of mineral, animal vegetable or synthetic origin. Non-limiting examples of mineral waxes include petroleum waxes such as paraffin and microcrystalline waxes, animal waxes include beeswax, vegetable waxes include carnauba, candelilla, rice bran, esparto, flax and sugarcane, and synthetic waxes include those produced by the Fischer-Tropsch synthesis, and mixtures thereof.

Suitable oils and fats usable in gum compositions include hydrogenated or partially hydrogenated vegetable or animal fats, such as cottonseed oil, soybean oil, coconut oil, palm kernel oil, beef tallow, hydrogenated tallow, lard, cocoa butter, lanolin and the like; fatty acids such as palmitic, oleic, stearic, linoleic, lauric, myristic, caproic, caprylic, decanoic or esters and salts as sodium stearate and potassium stearate. These ingredients when used are generally present in amounts up to about 7% by weight of the gum composition, and preferably up to about 3.5% by weight of the gum composition.

Preferred as softeners are the hydrogenated vegetable oils and include soybean oil and cottonseed oil which may be employed alone or in combination. These softeners provide the gum base composition with good texture and soft chew characteristics. These softeners are generally employed in an amount from about 5% to about 14% by weight of the gum base composition.

Emulsifiers aid in dispersing the immiscible components of the gum base composition into a single stable system. They provide hydrophilic character to a gum base and aid in plasticizing the resins and polyvinyl acetates. They also affect the softness of the base and the, bubble character of the base. Typical emulsifiers include acetylated monoglyceride, glyceryl monostearate, lecithin, fatty acid monoglycerides, diglycerides, propylene glycol monostearate, lecithin, triacetin, glyceryl triacetate and the like, and mixtures thereof.

Preferred emulsifiers are glyceryl monostearate and acetylated monogylcerides. These serve as plasticizing agents. The emulsifiers may be employed in an amount of from about 2% to about 15% by weight of the gum base composition, and preferably from about 7% to about 11% by weight of the gum base composition.

The fats, oils, waxes, emulsifiers and certain sugar bulking agents are often grouped together and referred to as softening agents. Because of the low molecular weight of these ingredients, the softeners are able to penetrate the fundamental structure of the gum base making it plastic and less viscous. Useful plasticizers and softeners of the above include lanolin, palmitic acid, oleic acid, stearic acid, sodium stearate, potassium stearate, glyceryl triacetate, glyceryl lecithin, glyceryl monostearate, propylene glycol nonastearate, acetylated monoglyceride, glycerin, fully unsaturated vegetable oils such as nonhydrogenated cottonseed oil, hydrogenated vegetable oils, petroleum waxes, sorbitan monostearate, tallow, and the like, and mixtures thereof and also include high fructose corn syrup, corn syrup, sorbitol solution, hydrogenated starch hydrolysate, and the like, and mixtures thereof.

The amount of softener present should he an effective amount to provide a finished chewing gum with the desired chew bulkiness and softness. When used as softeners these materials are generally employed in the gum base composition in an amount of up to about 25%, and preferably in an amount of from about 1% to about 17%, by weight of the gum base composition.

The gum base may further contain a surfactant. Examples of suitable surfactants include polyoxyethylene (20) sorbitan monoleate, polyoxyethylene (20) sorbitan monolaurate, polyethylene (4) sorbitan monolaurate, polyoxyethylene (20) sorbitan monopalmitate, polyoxyethylene (20) sorbitan monostearate, polyoxyethylene, (4) sorbitan monostearate, polyoxyethylene (20) sorbitan tristearate, polyoxyethylene (5) sorbitan monooleate, polyoxyethylene (20) sorbitan trioleate, sorbitan monolaurate, and the like. The amount of surfactant present should be effective to provide the finished chewing gum with the desired softness. Typically, the surfactant is employed in the base in an amount of from about 0.5% to about 3.0% by weight based on the total weight of the gum base.

The gum base composition of this invention may also include effective amounts of fillers sometimes referred to as bulking agents. These materials add firmness and bulk and affect the texture and the flavor release of the chewing gum. Useful fillers include organic and inorganic compounds (mineral adjuvants) such as calcium carbonate, magnesium carbonate, ground limestone, magnesium silicate, calcium phosphate, cellulose polymers, clay, alumina, aluminum hydroxide, aluminum silicate, talc, tricalcium phosphate, dicalcium phosphate, and the like, and mixtures thereof. These fillers or adjuvants may be used in the gum base compositions in various amounts. The amount of the filler present should be effective to provide a finished chewing gum with the desired flavor release and integrity. Typically, the filler is employed in the gum base composition in an amount from about 1% to about 40%, and preferably from about 5% to about 20%, by weight of the gum base composition.

The gum base may also comprise an antioxidant to provide improved stability, lessen any oil-taste and provide longer shelf life. Typical non-limiting examples of antioxidants are butylated hydroxytoluene (BHT), butylated hydroxy anisole (BHA), propyl gallate. Mixtures thereof may also be used.

Other Gum Ingredients

The remaining ingredients in chewing gum compositions are conventional and usually comprise from 10 to 85% by weight of the final product.

Examples thereof are sweetening agents, softeners, coloring agents, bulking agents, thickening agents, and flavoring agents of the type and in the amounts conventionally used for chewing gum.

Suitable flavoring agents those flavors known to the skilled artisan such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, wintergreen oil (methyl salicylate), peppermint oil, clove oil, bay oil, anise oil, *eucalyptus* oil, thyme oil, cedar leaf oil, oil of nutmeg, allspice, oil of sage, mace, oil of bitter almonds, and *cassia* oil. Other useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixtures. Commonly used flavors include mints such as peppermint, menthol, artificial vanilla, cinnamon derivatives, and various fruit flavors, whether employed individually or in admixture.

Other useful flavoring agents include aldehydes and esters such as cinnamyl acetate, cinnamaldehyde, citrate diethylacetal, dihydrocarvyl acetate, eugenyl formate, p-methyl anisole, and so forth may be used. Generally, any flavoring or food additive may be used.

Further examples of aldehyde flavorings include, but are not limited to, acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2-hexenal (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The amount of flavoring agent employed herein is normally a matter of preference subject to such factors as the type of final chewing gum composition, the individual flavor, the gum employed, and the strength of flavor desired. Thus, the amount of flavoring may be varied in order to obtain the result desired in the final product and such variations are within the capabilities of those skilled in the art without the need for undue experimentation. In gum compositions, the flavoring agent is generally present in amounts from about 0.02% to about 5% by weight of the chewing gum composition.

The chewing gum compositions generally include bulking agents. These bulking agents (carders, extenders) may be water-soluble and include bulking agents selected from the group consisting of, but not limited to, monosaccharides, disaccharides, polysaccharides, sugar alcohols, and mixtures thereof; sorbitol, xylitol, maltitol, mannitol, isomalt (a racemic mixture of alpha-D-glucopyranosyl-1,6-mannitol and alpha-D-glucopyranosyl-1,6-sorbitol manufactured under the tradename Palatinit™ by Suddeutsche Zucker), glycerol, aspartame, Lycasin® glycerol, galactitol acesulphame K, saccharine and salts thereof, cyclamate and salts thereof, neohesperidine dihydrochalcone, glycyrrhizinic acid and salts thereof, thaumantine and sucralose as well as mixtures thereof or mixtures thereof with other suitable sweeteners, maltodextrins; hydrogenated starch hydrolysates; hydrogenated hexoses; hydrogenated disaccharides; minerals, such as calcium carbonate, talc, titanium dioxide, dicalcium phosphate, celluloses and the and the like, and mixtures thereof. Bulking agents may be used in amounts up to about 60%, and preferably in amounts from about 25% to about 60%, by weight of the chewing gum composition.

The chewing gum compositions may also include a high intensity sweetening agent (sweeteners). High intensity sweetening agents have a sweetness intensity substantially greater than that of sucrose. Examples of suitable intense sweeteners include:

a) water-soluble naturally-occurring intense sweeteners such as dihydrochalcones, monellin, steviosides, glycyrrhizin, dihydroflavenol, and L-aminodicarboxylic acid aminoalkonoic acid ester amides, such as those disclosed in in U.S. Pat. No. 4,619,834, and mixtures thereof;

b) water-soluble artificial sweeteners including the soluble saccharin salts such as sodium or calcium saccharin salts, cyclamate salts, the sodium, ammonium or calcium salts of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfam-K), the free acid form of saccharin, and the like, and mixtures thereof;

c) dipeptide based sweeteners including L-aspartic acid derived sweeteners such as 1-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2.5-dihydro-L-phenylalanine, L-aspartyl-L-(1-cyclohexen)-alanine, and the like, and mixtures thereof;

d) water-soluble intense, sweeteners derived from naturally-occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose®; examples of chlorodeoxysucrose and chlorodeoxygalactosucrose derivatives include but are not limited to: to 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1'-deoxy-beta-D-fructofuranoside, or 4,1'-dichloro-4,1'-dideoxygalactosucrose; 1',6'-dichloro-1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fluctofuranoside, or 4,6,1',6'-tetrachloro-4,6,1',6'-tetradeoxygalacto-sucrose; and 4,6,1',6'-tetradeoxy-sucrose, and mixtures thereof; and e) protein based intense sweeteners such as *Thaumaoccous daniclii* (Thaumatin I and II). The amount of sweetener employed in the chewing gum composition will vary with the sweetener selected for a particular chewing gum. Thus, for any given sweetener a sufficient amount of sweetener is used to provide the level of sweetness desired. The saccharide sweeteners and sugar alcohols described above are usually used in an amount of from about 1% to about 70% and preferably in an amount of from about 40% to about 50%, by weight based on the total weight of the chewing gum composition. The intense sweeteners described above are usually used in an amount of up to about 1%, preferably from about 0.05% to about 0.4%, by weight based on the total weight of the chewing gum composition.

The coloring agents useful in the present invention are used in amounts effective to produce the desired color. These coloring agents include pigments, which may be incorporated in amounts up to about 6%, by weight of the gum composition. A preferred pigment, titanium dioxide, may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative non-limiting examples include the indigoid dye known as F.D.& C. Blue No. 2, which is the disodium salt of 5,5-indigotindisulfonic acid. Similarly, the dye known as F.D.& C. Green No. 1 comprises a triphenylmethane dye and is the monosodium salt of 4-[4-(N-ethyl-N-p-sulfoniumbenzylamino)diphenylmethylene]-[1-(N-ethyl-N-p-sulfoniumbenzyl)-delta-2,5-cyclohexadieneimine].

Examples of thickening agents include methyl cellulose, alginates, carrageenan, xanthan gum, gelatin, carob, tragacanth, and locust bean, emulsifiers, such as lecithin and glyceryl monostearate, acidulants such as malic acid, adipic acid, citric acid, tartaric acid, fumaric acid, and mixtures thereof.

The plasticizers, softening agents, emulsifiers, waxes, and antioxidants discussed above as being suitable for use in the gum base may also be used in the chewing gum composition.

Active Gum Ingredients

Oral care compositions of the invention in the form of a chewing gum may also contain various active ingredients such as antimicrobial agents, Zn salts, fluorides, and urea.

Moreover, the oral composition according to the invention may, if desired, include any other active ingredients, such as anti-caries agents, anti-calculus agents, anti-plaque agents, anti-periodontal agents, anti-fungal agents, anti-smoking agents, anti-cold agents, agents against gingivitis, etc.

The antimicrobials used in the compositions can be any of a wide of cationic antimicrobial agents such as quaternary ammonium compounds (e.g., cetyl pyridinium chloride) and substituted guanidines such as chlorhexidine and the corresponding compound alexidine. Mixtures of cationic antimicrobials may also be used in the present invention.

Antimicrobial quaternary ammonium compounds include those in which one or two of the substituents on the quaternary nitrogen has a carbon chain length (typically alkyl group) of some 8 to 20, typically 10 to 18 carbon atoms while the remaining substituents (typically alkyl or benzyl group) have a lower number of carbon atoms, such as 1 to 7 carbon atoms, typically methyl or ethyl groups. Dodecyl trimethyl ammonium bromide, tetradecyl pyridinium chloride, tetradecyl ethyl pyridinium chloride, dodecyl dimethyl (2-phenoxyethyl) ammonium bromide, benzyl dimethylstearyl ammonium chloride, cetyl pyridinium chloride, quaternized 5-amino-1,3-bis 2-ethyl-hexyl)-5-methyl hexa hydropyrimidine and benzethonium chloride are exemplary of typical quaternary ammonium antibacterial agents. Other compounds are the bis[4-(R-amino)-1-pyridinium] alkanes as disclosed in U.S. Pat. No. 4,206,215, Jun. 3, 1980 to Bailey incorporated herein by reference. The pyridinium compounds are the preferred quaternary ammonium compounds.

The cationic antimicrobial is generally used in the present compositions at a level of from about 0.02% to about 1%, preferably from about 0.3% to about 0.7% most preferably from about 0.3% to about 0.5%.

As easily soluble zinc salt it is in principle possible to use any physiologically acceptable, easily soluble zinc salt of an inorganic or organic acid, said salt being able to release zinc ions and being approved for the intended use, such as in foodstuffs, cosmetics or pharmaceutical products. Non-limiting examples are for instance zinc citrate, zinc sulphate, zinc lactate, zinc chloride, zinc acetate as well as mixtures thereof. Among these salts zinc acetate is preferred.

The zinc salt used must be easily soluble such that a release is ensured in the oral cavity of an amount of zinc ions efficient for the purpose aimed at within a suitable period of time.

Advantageously, the zinc salt is present in the oral composition in an amount of from 0.001 to 1.25% by weight. The amount used depends on the administration form and the intended use and is adapted such that an amount of zinc ions efficient for the intended use is released.

As taste-masking salt is used at least one salt selected among sodium chloride, ammonium chloride and physiologically acceptable alkali metal, alkaline earth metal and/or ammonium carbonates.

The alkali metal is in particular sodium or potassium, whereas the alkaline earth metal advantageously is calcium or magnesium. Particularly preferred taste-masking salts are sodium, potassium and magnesium carbonates, sodium chloride, ammonium chloride as well as mixtures thereof.

The taste-masking salt is advantageously used in the oral composition in an amount of from 0.05 to 6.25% by weight, more preferred from 0.25 to 3.50% by weight, such as from 0.50 to 2.50% by weight.

The amount used of taste-masking salt for masking the taste of zinc can in each case be determined by a person skilled in the art and depends on the particular zinc salt in question and the selected administration form.

Urea is used as an anticariogenic product for neutralizing the acid produced in dental plaque subsequent to eating or drinking. Beyond urea the composition also can contain pharmacologically acceptable substances capable of releasing urea under the conditions prevailing in the mouth. Examples thereof are: Salts and addition compounds between urea and inorganic compounds such as magnesium sulphate, calcium phosphate, sodium chloride, etc.

The urea content of the composition according to the invention varies between 0.05% by weight and 80% by weight, preferably between 0.2% by weight and 25% by weight.

The chewing gum compositions may be prepared using standard techniques and equipment known to those skilled in the art. The apparatus useful in accordance with the present invention comprises mixing and beating apparatus as well.

Lozenges and Pastilles

Lozenges are flavored medicated dosage forms intended to be sucked and held in the mouth or pharynx. They may contain vitamins, antibiotics, antiseptics, local anesthetics, antihistamines, decongestants, corticosteroids, astringents, analgesics, aromatics, demulcents, or combinations of these ingredients. Lozenges may take various shapes, the most common being the flat, circular, octagonal, and biconvex forms. Another type, called bacilli, are in the form of short rods or cylinders. A soft variety of lozenge, called a pastille, consists of medicament in a gelatin or glycerogelatin base or in base of acacia, sucrose, and water (H. A. Lieberman, Pharmaceutical Dosage Forms: Tablets, Volume 1 (1980), Marcel Dekker, Inc., New York, N.Y.).

In a preferred embodiment, the present invention relates to oral care compositions in the form of a lozenge or pastille comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity; and wherein the at least one oral care ingredient is selected from lubricant, bulking agent, sweetening agent, and flavoring agent.

Lubricants

The use of a lubricant in the manufacture of compressed lozenges is to facilitate the release of the lozenge from the die in which it is formed. The lubricant used in the present invention is a solid material which is not charged, and which will not interfere (e.g., complex) with the cationic antimicrobial. The material should preferably be water insoluble. One type of suitable material meeting these requirements is a non-toxic hydrocarbon fat or derivative. Examples include hydrogenated tallow and hydrogenated vegetable oil. Polyethylene glycols may also be used as a lubricant so long as they are solid materials which generally means having a molecular weight in the 4000 Da to 6000 Da range. These materials can also be used as a filler as noted below.

Mixtures of lubricants may also be used in the present invention. The lubricant is used at level of from about 0.1% to about 4.0% preferably from about 0.5% to about 2%.

Lozenge Vehicle

The term "lozenge vehicle" is used herein to denote the material(s) which carries the active ingredients, such fructanase(s), other enzymes, and therapeutic agents, as well as the lubricant. These materials are also known as bulking agents or fillers. Since the vehicle is non-cariogenic, the vehicle should be free of sucrose and similar materials.

Acceptable filler materials include mannitol, sorbitol, xylitol, polyethylene glycol and non-cariogenic dextrans. The fillers may be used alone or in combination.

Mannitol is a naturally occurring sugar alcohol and is available as a fine powder. It has a sweetness of only about 50% of that of sucrose. However, mannitol's negative heat of solution enables it to impart a pleasant, cooling sensation in the mouth as the lozenge dissolves.

Sorbitol is a chemical isomer of mannitol and possesses a similar degree of sweetness. Its heat of solution, being negative, also provides for a pleasant, cooling sensation in the mouth. Sorbitol is available either as free flowing granules or as a crystalline powder. Polyethylene glycols (PEG's) can also be used in the present compositions. These materials are polymers of ethylene oxide with the generalized formula $HOCH_2\ (CH_2OCH_2)_nCH_2OH$. The use of PEG's alone is not favored but their use in combination with other fillers is acceptable. The molecular weights found most desirable are between 4000 Da and 6000 Da.

Fillers are generally used in the present invention at a level of from about 85% to about 99.8%, preferably from about 90% to about 98%, most preferably from about 94% to about 97%.

Other Lozenge Components

Acceptable lozenges may be manufactured using just an active ingredient, the lubricant and the filler material as outlined above. However, in order to make the lozenges more acceptable from an aesthetic viewpoint, generally included are materials such as spray-dried or encapsulated flavors or liquid flavors adsorbed onto a suitable diluent. Spray-dried or encapsulated flavors are preferred. Suitable flavors include oil of peppermint, oil of wintergreen, oil of *sassafras*, oil of spearmint and oil of clove. Sweetening agents are also acceptable for use in the present compositions. Suitable agents include aspartame, acesulfame, saccharin, dextrose and levulose. Sweetening and flavoring agents are generally used in the compositions of this invention at levels of from about 0.1% to about 2%, preferably from about 0.25% to about 1.5%.

It is also acceptable to have a solid form of a water-soluble fluoride compound present in the present lozenges in an amount sufficient to give a fluoride concentration of from about 0.0025% to about 5.0% by weight, preferably from about 0.005% to about 2.0% by weight, to provide additionally anticaries effectiveness. Preferred fluorides are sodium fluoride, stannous fluoride, indium fluoride and sodium monofluorophosphate. The lozenges may also contain various active ingredients such as anti-microbial agents, Zn salts, fluorides, and urea (supra).

Confectionaries and Candy

In a preferred embodiment, the present invention relates to oral care compositions in the form of a confectionary or candy comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity; and wherein the at least one oral care ingredient is selected from coloring agent, sweetening agent, flavoring agent, and oil-modifying agent.

The preparation of confectionery formulations is historically well known and has changed little through the years. Confectionery items have been classified as either "hard" confectionery or "soft" confectionery. The volatile oil-modifying agent of the present invention can be incorporated by admixing the modifying agent into conventional hard and soft confections.

Hard confectionery may be processed and formulated by conventional means. In general, a hard confectionery has a base composed of a mixture of sugar and other carbohydrate bulking agents kept in an amorphous or glassy condition. This form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose but may include other materials. Further ingredients such as flavorings, sweeteners, acidulants, colorants and so forth may also be added.

Such confectionery may be routinely prepared by conventional methods such as those involving fire cookers, vacuum cookers, and scraped-surface cookers also referred to as high speed atmospheric cookers.

Fire cookers involve the traditional method of making a candy base. In this method, the desired quantity of carbohydrate bulking agent is dissolved in water by heating the agent in a kettle until the bulking agent dissolves. Additional bulking agent may then be added, and cooking continued until a final temperature of 145 to 156° C. is achieved. The batch is then cooled and worked as a plastic-like mass to incorporate additives such as flavor, colorants and the like.

A high-speed atmospheric cooker uses a beat-exchanger surface, which involves spreading a film of candy on a heat exchange surface, the candy is heated to 165 to 170° C. in a few minutes. The candy is then rapidly cooled to 100 to 120° C. and worked as a plastic-like mass enabling incorporation of the additives, such as flavors, colorants and the like.

In vacuum cookers, the carbohydrate bulking agent is boiled to 125 to 132° C., vacuum is applied, and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavors, colorants and other additives during conventional manufacturing of hard confectionery is determined by the time needed to obtain a uniform distribution of the materials. Normally, mixing times of from 4 to 10 minutes have been found to be acceptable.

Once the candy mass has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms: Tablets, Volume 1 (1980), Marcel Dekker, Inc., New York, N.Y.

The apparatus useful in accordance with the present invention comprises cooking and mixing apparatus well known in the confectionery manufacturing arts, and election of the specific apparatus will be apparent to the artisan. In contrast, compressed tablet confections contain particular materials and are formed into structures under pressure.

These confections generally contain sugars in amounts up to about 95%, by weight of the composition, and typical tablet excipients such as binders and lubricants as well as flavoring agent, colorants and so forth. Similar to hard confectionery, soft confectionery may be utilized in this invention. The preparation of soft confections, such as nougat, involves conventional methods, such as the combination of two primary components, namely (1) a high boiling syrup such as corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The flavoring components of the confection are flavors having an associated bitter taste or other unpleasant after taste. These flavoring components may be chosen from natural and synthetic flavoring liquids such as volatile oils, synthetic flavor oils, flavoring aromatic and oils, liquids, oleoresins or extracts derived from plants, leaves, flowers, fruits, stew and combinations thereof. Non-limiting representative examples of volatile oils include spearmint oil, cinnamon oil, oil of wintergreen (methyl salicylate), peppermint oil, menthol, clove oil, bay oil, anise oil, *eucalyptus* oil, thyme oil, cedar leaf oil, oil of nutmeg, allspice oil, oil of sage, mace extract, oil of bitter almonds, and *cassia* oil. In addition, the confection may also contain artificial, natural or synthetic flavors including fruit flavors such as vanilla, and citrus oils including lemon, orange, grape, lime and grapefruit and fruit essences including apple, pear, peach, grape, strawberry, raspberry, cherry, plum, pineapple, apricot and so forth individual and mixed.

Other useful flavorings include aldehydes and esters such as benzaldehyde (cherry, almond), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyl-octanal (green fruit), and 2-dodecenal (citrus, mandarin), mixtures thereof and the like.

In the instance where sweeteners are utilized, the present invention contemplates the inclusion of those sweeteners well known in the art, including both natural and artificial sweeteners. The sweeteners may be chosen from the following non-limiting list: sugars such as sucrose, glucose (corn syrup), dextrose, invert sugar, fructose, and mixtures thereof, saccharin and its various salts such as the sodium or calcium salt; cyclamic acid and its various salts such as the sodium salt; the dipeptide sweeteners such as aspartame, dihydrachalcone compounds, glycyrrhizin; *Stevia Rebaudiana* (Stevioside); chloro-derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated is the synthetic sweetener 3,6-dihydro-6-methyl-1,2,3-oxathiazin-4-one-2,2-dioxide, particularly the potassium (acesulfame-K), sodium and calcium salts thereof.

The confection may also include a colorant. The colorants may be selected from any of the numerous dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino)diphenylmethylane]-[1-(N-ethyl-N-p-sulfoniumbenzyl)-2-5-cyclohexadieneimine]. A full recitation of all FD&C and D&C dyes and their corresponding chemical structures may be found in the Kirk-Othmer Encyclopedia of Chemical Technology, in Volume 5.

The confectionary may also include a volatile oil-modifying agent such as *capsicum* oleoresin. An oil-modifying agent is present in an amount, which is undetected as a separate ingredient in the oral cavity, but nevertheless has the ability to modify sensory perception of the volatile oil.

The oil-modifying agent is present in an amount of from about 1 to about 150 ppm of the confection. The *capsicum* is available from *Capsicum* minimum, *Capsicum frutescens, Capsicum annuum*, and similar varieties. Commercially, the fruits of *capsicum* are referred to as chilies or as peppers. These fruits are known for their extreme potency of bite, pungency and characteristic odor.

With respect to confectionery compressed tablet formulations, such will contain a tablet granulation base and various additives such as sweeteners and flavors. The tablet granulation base employed will vary depending upon factors such as the type of base used, friability desired and other components used to make the final product. These confections generally contain sugars in amounts up to 95% by weight of the composition.

The confectionery compressed tablet may additionally include tablet excipients such as binders or lubricants, as well as flavoring agents, coloring agents, and volatile oils and volatile oil-modifying agents.

The variations that one may practice with regard to these confections are wide ranging and within the ability of those skilled in the art particularly with regard to the use of additional composition fillers, flavoring agents, the use of coloring agents, etc.

External Oral Care Compositions

An external oral care formulation, e.g., denture cleaning solution, denture cleaning tablet, denture cleaning powder, and the like, may include ingredients and/or substances selected from the following categories:

| Type of component | Examples | Amount (weight %) |
|---|---|---|
| Carrier liquid | Water, ethanol (18-27%), water/ethanol mixture | 0 to 95% |
| Disinfectant and bleaching agents | Sodium hypochlorite, Potassium Monopersulfate, Sodium Perborate | 0.001 to 95% |
| Cleaning agents | Sodium bicarbonate, citric acid, sodium perborate, sodium polyphosphate, potassium monopersulfate | 0.001 to 95% |
| Detergents and surfactants | Sodium lauryl sulfate (SLS) | 0.001 to 10% |
| Foaming agents | Polyethylene glycols (PEGs) | 0.0001 to 10% |
| Preservatives | Sodium benzoate, citric acid, | 0.001 to 75% |
| Flavoring agents | Peppermint, spearmint | 0.001 to 5% |

In a preferred embodiment the at least on oral care ingredient is selected from the group consisting of carrier liquids, disinfectant and bleaching agents, cleaning agents, detergents and surfactants, foaming agents, preservatives, and flavoring agents.

Other Oral Care Compositions

Oral compositions of the invention may also be included in filaments suitable for use in dental cleaning, e.g., filaments useful as dental floss. Preferably, the oral care composition is coated onto the exterior of the filament. Thus, in a preferred embodiment, the present invention relates to a filament comprising an oral care composition comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity; and wherein the filament is suitable for dental cleaning.

Oral care compositions of the invention may also be included in an animal treat and thereby be used for improving oral health of an animal. Thus, in a preferred embodiment, the present invention relates to an oral care composition of the invention in the form of an animal treat.

Preferably, the animal treat is a pet treat. Most preferably, the animal treat is a dog treat.

The oral composition may be coated onto the outer surface of the animal treat, mixed in with the other treat ingredients, or comprised in an inner compartment of the treat. Preferably, the oral care composition is comprised in an inner compartment of the treat.

Suitable types of animal treats as well as methods for making such treats are well-known to the skilled person and are described in, e.g., EP 0 258 037 A2, U.S. Pat. No. 4,892,748 B2, and U.S. Pat. No. 8,496,985 B2.

In an alternative aspect, the present invention relates to an animal treat comprising an oral care composition comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity.

Preferably, the animal treat is a pet treat. Most preferably, the animal treat is a dog treat.

The oral composition may be coated onto the outer surface of the animal treat, mixed in with the other treat ingredients, or comprised in an inner compartment of the treat. Preferably, the oral care composition is comprised in an inner compartment of the treat.

Treatment of Oral Disease

The oral care compositions of the invention are suitable for use in the treatment of oral disease, wherein removal of biofilm is desired. The compositions of the invention are particularly suitable for treating periodontal diseases and dental caries.

Periodontal disease, also known as gum disease, is a set of inflammatory conditions caused by bacterial infection and subsequent biofilm build-up on the test and the tissues surrounding the teeth. Periodontal disease may be divided in terms of severity into the following categories: gingivitis (including plaque-induced gingivitis), chronic periodontitis, aggressive periodontitis, periodontitis as a manifestation of systemic disease, necrotizing ulcerative gingivitis/periodontitis, abscesses of the periodontium, and combined periodontic-endodontic lesions. Periodontal disease may further be considered either localized or generalized depending on the extent of the affected area.

Dental caries, also known as tooth decay or cavities, is caused by organic acids, such as lactic acid, being released by certain biofilm-forming bacteria residing in the oral cavity, including *Streptococcus mutans* and some *Lactobacillus* species. Dental caries may be associated with further complications such as inflammation of the tissue around the teeth, tooth loss, and infection or abscess formation. Dental caries may be classified by location, etiology, rate of progression, and affected hard tissues, for instance according to the G.V. Black classification (class I, II, III, IV, V, and VI).

In one aspect, the present invention relates to an oral care composition comprising:

(a) a fructanase comprising a GH32 domain, a GH32C domain, and belonging to the WMND clade and comprising the motif WMND (SEQ ID NO:12); and (b) at least one oral care ingredient;

for use as a medicament;

wherein the fructanase has at least two, e.g., at least three, or four, enzymatic activities selected from the group consisting of fructan-degrading activity, levan-degrading activity, inulin-degrading activity, and sucrose-degrading activity.

In one aspect, the present invention relates to an oral care composition comprising:

(a) a fructanase comprising a GH32 domain, a GH32C domain, and belonging to the WMND clade and comprising the motif WMND (SEQ ID NO:12); and (b) at least one oral care ingredient;

for use in the treatment of oral disease;

wherein the fructanase has at least two, e.g., at least three, or four, enzymatic activities selected from the group consisting of fructan-degrading activity, levan-degrading activity, inulin-degrading activity, and sucrose-degrading activity.

In a preferred embodiment, the present invention relates to an oral care composition comprising:

(a) a fructanase comprising a GH32 domain, a GH32C domain, and belonging to the WMND clade and comprising the motif WMND (SEQ ID NO:12); and (b) at least one oral care ingredient;

for use in the treatment of periodontal disease and/or dental caries;

wherein the fructanase has at least two, e.g., at least three, or four, enzymatic activities selected from the group consisting of fructan-degrading activity, levan-degrading activity, inulin-degrading activity, and sucrose-degrading activity.

In one aspect, the present invention relates to use of an oral care composition comprising:

(a) a fructanase comprising a GH32 domain, a GH32C domain, and belonging to the WMND clade and comprising the motif WMND (SEQ ID NO:12); and (b) at least one oral care ingredient;

for treatment or prophylactic treatment of a human or animal subject;

wherein the fructanase has at least two, e.g., at least three, or four, enzymatic activities selected from the group consisting of fructan-degrading activity, levan-degrading activity, inulin-degrading activity, and sucrose-degrading activity.

In one aspect, the present invention relates to a method of treatment of a human or animal subject, the method comprising administering an oral care composition comprising:

(a) a fructanase comprising a GH32 domain, a GH32C domain, and belonging to the WMND clade and comprising the motif WMND (SEQ ID NO:12); and (b) at least one oral care ingredient;

to a human or animal subject;

wherein the fructanase has at least two, e.g., at least three, or four, enzymatic activities selected from the group consisting of fructan-degrading activity, levan-degrading activity, inulin-degrading activity, and sucrose-degrading activity. Preferably, the oral care composition is administered to the oral cavity of said subject.

In one aspect, the present invention relates to a method for removing oral biofilm, the method comprising contacting the biofilm with an oral care composition comprising (a) a fructanase comprising a GH32 domain, a GH32C domain, and belonging to the WMND clade and comprising the motif WMND (SEQ ID NO:12); and (b) at least one oral care ingredient; wherein the fructanase has at least two, e.g., at least three, or four, enzymatic activities selected from the group consisting of fructan-degrading activity, levan-degrading activity, inulin-degrading activity, and sucrose-degrading activity. In one embodiment, the oral care composition is an external oral care composition, and the biofilm is located on an object; preferably the object is a denture. In one embodiment, object is located inside or outside the oral cavity.

EXAMPLES

Assays

DNase Activity Assay 1

DNase activity was determined on DNase Test Agar with Methyl Green (BD, Franklin Lakes, NJ, USA), which was prepared according to the manual from supplier. Briefly, 21 g of agar was dissolved in 500 ml water and then autoclaved for 15 min at 121° C. Autoclaved agar was tempered to 48° C. in water bath, and 20 ml of agar was poured into petri dishes with and allowed to solidify by incubation o/n at room temperature. On solidified agar plates, 5 µl of enzyme solutions are added and DNase activity is observed as colorless zones around the spotted enzyme solutions.

DNase Activity Assay 2

DNase activity was determined by using the DNaseAlert Kit (11-02-01-04, IDT Integrated DNA Technologies) according to the supplier's manual. Briefly, 95 µl DNase sample was mixed with 5 µl substrate in a microtiter plate, and fluorescence was immediately measured using a Clariostar microtiter reader from BMG Labtech (536 nm excitation, 556 nm emission).

Example 1: Cloning and Expression of Fructanases

SEQ ID NOs:2-6

The DNA encoding SEQ ID NO:2 and SEQ ID NO:6 was isolated from strain of *Bacillus licheniformis* and *Flavobacterium banpakuense*, respectively, collected in United States of America (see Table 1). Chromosomal DNA from the strain was subjected to full genome sequencing using Next Generation Sequencing technology. The genome sequence was analyzed for protein sequences that contained glycosyl hydrolase domains, as defined in the CAZy database (www.cazy.org, Lombard V, et al. 2014, Nucleic Acids Res 42:D490-D495). A sequence containing a Glycoside Hydrolase Family GH32 domain (GH32, CAZy database, www.cazy.org, Lombard V, et al. 2014, Nucleic Acids Res 42:D490-D495) was identified in the genomes.

The DNA encoding SEQ ID NO:3, SEQ ID NO:4, and SEQ ID NO:5 originating from strains of *Bacillus licheniformis, Arthrobacter* sp. Leaf337, and *Bacillus subtilis*, respectively, was identified in public databases (see Table 1).

The DNA encoding SEQ ID NO:2, SEQ ID NO:3, SEQ ID NO:4, SEQ ID NO:5, and SEQ ID NO:6 was ordered as synthetic genes from Twist Bioscience. The synthetic DNA fragments were directionally assembled to a *Bacillus* expression vector described in WO 2012/025577 by the standard Golden Gate cloning method using BsaI and T4 DNA ligase enzymes. Briefly, the DNA encoding the mature peptide of the gene was cloned in frame to a *Bacillus clausii* secretion signal (BcSP; with the following amino acid sequence: MKKPLGKIVASTALLISVAFSSSIASA (SEQ ID NO:8). BcSP replaced the native secretion signal in the gene. Downstream of the BcSP sequence, an affinity tag sequence was introduced to ease the purification process (His-tag; with the following amino acid sequence: HHHHHHPR, SEQ ID NO:9). The gene that was expressed therefore comprised the BcSP sequence followed by the His-tag sequence followed by the mature fructanase sequence.

The final expression plasmids were transformed into a *Bacillus subtilis* expression host. The gene was integrated by homologous recombination into the *Bacillus subtilis* host cell genome upon transformation. The gene construct was expressed under the control of a triple promoter system (as described in WO 1999/43835). A gene encoding chloramphenicol acetyltransferase was used as maker (as described in Diderichsen et al., 1993, *Plasmid* 30: 312-315). Transformants were selected on LB media agar supplemented with 6 microgram of chloramphenicol per ml. One recombinant *Bacillus subtilis* clone containing the expression constructs was selected and was cultivated on a rotary shaking table in 500 ml baffled Erlenmeyer flasks each containing 100 ml yeast extract-based media. After 3-5 days of cultivation at 30° C. to 37° C., the enzyme containing supernatant was harvested by centrifugation and the enzymes was purified by His-tag purification by immobilized metal chromatography (IMAC) using $Ni^{2+}$ as the metal ion on 5 mL HisTrap Excel columns (GE Healthcare Life Sciences). The purification took place at pH 7 and the bound protein was eluted with imidazole. The purity of the purified enzymes was checked by SDS-PAGE and the concentration of the enzyme determined by absorbance at 280 nm after a buffer exchange in 50 mM HEPES, 100 mM NaCl, pH 7.0

SEQ ID NO:1 and SEQ ID NO:7

Cloning and expression of SEQ ID NO:1 was done as described in Example 14 of WO 2018/113745 with sequence specific primers SEQ ID NO:13 and SEQ ID NO:14 and PCR amplification using gDNA from *P. ochrochloron*, prepared as described in Example 2 of WO 2018/113745.

Cloning and expression of SEQ ID NO:7 was done using the strain ColS1300 and the strategy described in US 2019/0225988 with three overlapping fragments for integration in the niiA/niiD locus. The middle fragment, corresponding to the gene encoding SEQ ID NO:7 was PCR-amplified from *A. niger* gDNA prepared as described in Example 2 of WO 2018/113745 using primers SEQ ID NO:15 and SEQ ID NO:16.

Purification

Hydrophobic Interaction Chromatography purification was used for recovery of SEQ ID NOs:1-7 from fermentation broth: ammonium sulfate was added to a final concentration of 1.8 M and the sample was stirred for min 30 min before the final filtration step through a 0.2 μM membrane. The sample was applied to a 5 ml HiTrap™ Phenyl (HS) column on an Äkta Explorer. Prior to loading, the column was equilibrated in 5 column volumes (CV) with 50 mM HEPES+1.8 M AMS pH 7. In order to remove unbound material, the column was washed with 5 CV of 50 mM HEPES+1.8 M AMS pH 7 after sample application. The target protein was eluted from the column into a 10 ml loop using 50 mM HEPES+20% ethanol pH 7. From the loop, the sample was loaded onto a ~50 mL desalting column (HiPrep™ 26/10 Desalting), which was equilibrated with 3 CV of 50 mM HEPES+100 mM NaCl pH 7.0 before sample application. The target protein was transferred from the loop to the desalting column with 50 mM HEPES+100 mM NaCl pH 7.0. The target protein was eluted based on peak fractionation to obtain the sample in one tube. The flow rate was 10 ml/min. Concentration estimate was obtained by A280 analysis and purity of the sample by SDS-PAGE analysis.

TABLE 1

Countries of origin.

| SEQ ID NO: | Organism | Country of origin |
|---|---|---|
| 1 | *Penicilium ochrochloron* | Denmark |
| 2 | *Bacillus licheniformis* | USA |
| 3 | *Bacillus licheniformis* S16 | Pakistan |
| 4 | *Arthrobacter* sp. Leaf337 | Switzerland |
| 5 | *Bacillus subtilis* | Unknown |
| 6 | *Flavobacterium banpakuense* | USA |
| 7 | *Aspergillus niger* | Unknown |

Example 2: CONSTRUCTION OF PHYLOGENETIC TREES AND CLADES

GH32 Phylogenetic Tree

A phylogenetic tree of polypeptide sequences of the invention containing a GH32 domain was constructed as defined in CAZY (Lombard, Henrissat et al, 2014. The carbohydrate-active enzymes database (CAZy) in 2013. Nucleic Acids Res. 42, http://www.cazy.org/). The phylogenetic tree was constructed from a multiple alignment of mature polypeptide sequences containing at least one GH32 domain. The sequences were aligned using the MUSCLE algorithm version 3.8.31 (Edgar, 2004. *Nucleic Acids Research* 32(5): 1792-1797), and the trees were constructed using FastTree version 2.1.8 (Price et al., 2010, *PloS one* 5(3)) and visualized using iTOL (Letunic & Bork, 2007. *Bioinformatics* 23(1): 127-128).

A subset of polypeptides containing a GH32 domain, also contains a Glycosyl hydrolase family 32 C terminal domain, as defined by Pfam domain ID PF08244 (The Pfam protein families database: towards a more sustainable future: R. D. Finn, P. Coggill, R. Y. Eberhardt, S. R. Eddy, J. Mistry, A.

L. Mitchell, S. C. Potter, M. Punta, M. Qureshi, A. Sangrador-Vegas, G. A. Salazar, J. Tate, A. Bateman, *Nucleic Acids Research* (2016) Database Issue 44:D279-D285). All polypeptides of the invention contain a GH32 domain, as well as a glycosyl hydrolase family 32 C terminal domain. The glycosyl hydrolase family 32 C terminal domain will be denoted the GH32C domain. As an example, in SEQ ID NO:2 from *Bacillus licheniformis*, the GH32C domain is located at positions 328 to 483.

Generation of WMND Clade

Using the phylogenetic tree generated as described above, the polypeptides containing a GH32 domain and a GH32C domain can be separated into distinct polypeptide sequence clades. These clusters are defined by one or more short sequence motifs, as well as containing a GH32 and a GH32C domain.

In addition to containing a GH32 domain as well as a GH32C domain, the fructanases belong to the WMND clade. Fructanases of the WMND clade contain a GH32 domain, a GH32C domain, and comprise the motif WMND (SEQ ID NO:12), corresponding to amino acids WMND (Trp-Met-Asn-Asp) at positions 22 to 25 of the *Bacillus licheniformis* fructanase (SEQ ID NO:2). The aspartate at position 25 is part of the active site (W. Lammens et al. (2009), Journal of Experimental Botany, 60(3), 727-740).

All of SEQ ID NO:1, SEQ ID NO:2, SEQ ID NO:3, SEQ ID NO:4, SEQ ID NO:5, SEQ ID NO:6, and SEQ ID NO:7 belong to the WMD clade and comprise a GH32 domain, a GH32C domain, and the motif WMND (see Table 2 below).

TABLE 2

Amino acid positions of GH32 domain, GH32C domain, and WMND motif in SEQ ID NOS: 1-7

| SEQ ID NO: | GH32 domain | GH32C domain | WMND motif |
|---|---|---|---|
| 1 | 17 . . . 273 | 709 . . . 859 | 19 . . . 22 |
| 2 | 9 . . . 325 | 327 . . . 482 | 22 . . . 25 |
| 3 | 9 . . . 325 | 327 . . . 482 | 22 . . . 25 |
| 4 | 140 . . . 442 | 140 . . . 442 | 153 . . . 156 |
| 5 | 19 . . . 327 | 486 . . . 623 | 22 . . . 25 |
| 6 | 25 . . . 345 | 360 . . . 491 | 28 . . . 31 |
| 7 | 16 . . . 353 | 376 . . . 509 | 19 . . . 22 |

Example 3: Thermal Stability in Presence of Oral Care Components

Preparation of Oral Care Formulations for Thermal Stability Measurements

The thermal unfolding transition midpoint (Tm) of fructanases were measured in the presence of widely used components of oral care compositions within concentration ranges commonly used in oral care product formulations and selected oral care commercial products. The Tm parameter was used to evaluate the thermal stabilities as this is the temperature at which there are equal populations of folded and unfolded protein molecules. Tm is a widely accepted parameter to use when evaluating thermal stability.

TABLE 3

Oral care formulation ingredients used in this study to test mid-point of the thermal unfolding transition midpoint (Tm) of fructanases.

| Oral care component | Source | Product Number |
|---|---|---|
| Sodium benzoate | Sigma | 18106 |
| Arginine | Sigma | A1270000 |
| EDTA | Sigma | E5134 |
| Ethanol | VWR Chemicals | 20824.296 |
| Glycerol | Sigma | G5516 |
| Sodium phosphate | Sigma | 71643 |
| Sorbitol | Sigma | S6021 |
| Potassium sorbate | Sigma | 85520 |
| Sodium fluoride | Sigma | 919 |
| Hydrogen peroxide | Sigma | H1009 |
| Mannitol | Sigma | M9546 |

Highly pure and biotechnology grade reagents were obtained from various suppliers and stock solutions were freshly prepared using MilliQ water. These formulation chemicals and their stock as well as the final concentrations used in the Tm measurement are listed in the Table 3.

Purified preparations of fructanases were diluted to a stock concentration of 2 mg/ml prior to a further ten times dilution in model oral care formulations consisting of individual oral care components, citrate phosphate buffer (McIlvaine buffer) and MilliQ water corresponds to a final protein concentration of 0.2 mg/ml. All dilutions were made in a 384 well small volume deep well plate (Greiner Bio-One International, item number 784201) with a final volume of 70 μl and used for thermal stability measurements.

The Tm measurements for each fructanase was performed close to the physiological pH range of oral cavity using McIlvaine buffer at pH 5.0 and pH 6.0. 100 ml of McIlvaine buffer pH 5.0 was prepared by mixing 51.50 ml 0.2 M $Na_2HPO_4$ and 48.50 ml 0.1 M citric acid, and pH 6.0 McIlvaine buffer was prepared by mixing 63.15 ml 0.2 M $Na_2HPO_4$ and 36.85 ml 0.1 M citric acid.

Thermal Stability Measurements

Thermal stability measurements were performed using a capillary based nano differential scanning fluorescence instrument (nanoDSF); Prometheus NT.Plex (NanoTemper Technologies GmbH, München, Germany). Standard nanoDSF grade capillary chips were used (Cat #: PR-AC002) from NanoTemper Technologies.

The fructanase samples were loaded into the capillaries (each sample in triplicate) by capillary action. The emission intensities at 330 and 350 nm were optimized by altering the LED power on the instrument to ensure sufficient signal. The fluorescence signals at 330 and 350 nm were monitored continuously as a function of temperature (heating rate used for thermal unfolding was 3.3° C. per minute from 20° C. to 95° C.). The data was analyzed using the PR.StabilityAnalysis 1.1.0.11077 software provided by the manufacturer. The analysis is model independent and simply takes the peak maximum of the first derivative which corresponds to the approximate thermal unfolding transition midpoint, defined as Tm (see FIG. 1).

Reproducibility of Thermal Stability Data

FIG. 1 shows an example of the thermal stability data generated using the nanoDSF instrument. Panel A is an example of the data obtained (the ratio of the fluorescence emission at 350 nm to 330 nm) in triplicate for SEQ ID NO:2 as a function of temperature. Panel B shows the first derivative of the raw data in Panel A. The peak maximum in the first derivative plot corresponds to the mid-point of the thermal unfolding transition, referred to as Tm. In this example, Tm corresponds to 66.1° C. at pH 5.0 and is highly reproducible within the three replicates.

The data shown in FIG. 1 is an example of the type of data that was generated for fructanases in the presence of widely used oral care components using nanoDSF. In all cases, the data showed a clear unfolding transition, and a clearly defined peak in the first derivative, and were highly reproducible.

Results

Table 4 shows the average Tm values of fructanases originated from triplicate measurements at pH 5.0. The results of similar measurements conducted at pH 6.0 is shown in Table 5.

From the data shown in the Tables 4 and 5, it is clear that the fructanases have on par or improved thermal stability in the presence of a large number of formulation ingredients used in oral care, including such sodium fluoride, arginine, and hydrogen peroxide. In this context, the term "on par chemical stability" means that the Tm value of a fructanase co-formulated with an oral care component is within +/−5% of the Tm value of the same fructanase alone (i.e., the control), and the term "improved chemical stability" means that the Tm value of a fructanase co-formulated with an oral care component is increased more than 5%, e.g., 10%, 15%, 20%, 25%, 30%, 40%, 50%, 60%, 70%, 80%, 90%, 100%, or even more, compared to the Tm value of the same fructanase alone (i.e., the control).

Despite the adverse chemical reactions imparted by hydrogen peroxide, Tables 4 and 5 show that the fructanases exhibit good thermal stability at both high and low hydrogen peroxide concentrations.

Furthermore, it is evident that all evaluated formulation ingredients individually have no adverse effect on the thermal stability across the pH range tested compare to the control (Tables 4 and 5)

Taken together, the data presented in this Example clearly shows that these fructanases have high thermal stabilities in the presence of widely used oral care components, making them compatible with common oral care formulations.

TABLE 4

Mid-point of the thermal unfolding transition midpoint (Tm) for fructanases derived from first derivative under various formulation ingredients concentrations at pH 5.0.

| Reagent | Concentration (mM) | Tm (° C.) at pH 5.0 SEQ ID NO: 2 | SEQ ID NO: 3 | SEQ ID NO: 4 |
|---|---|---|---|---|
| Control | 0 | 66.1 | 64.5 | 46.9 |
| Sodium Benzoate | 10 | 65.5 | 64.0 | 46.9 |
| | 35 | 63.6 | 63.7 | 46.4 |
| Arginine | 30 | 60.8 | 62.0 | 32.8 |
| | 90 | 59.2 | 61.0 | 45.3 |
| EDTA | 1 | 65.9 | 64.4 | 46.6 |
| Ethanol | 1000 | 64.7 | 62.7 | 45.8 |
| Glycerol | 1000 | 67.6 | 65.9 | 47.7 |
| | 3250 | 70.6 | 68.2 | 49.7 |
| Sodium phosphate | 5 | 64.4 | 64.7 | 48.1 |
| | 10 | 65.8 | 63.9 | 46.7 |
| Sorbitol | 550 | 67.4 | 66.6 | 49.5 |
| | 2200 | 67.6 | 72.8 | 59.0 |
| Potassium Sorbate | 10 | 66.1 | 64.2 | 47.2 |
| | 35 | 65.1 | 64.3 | 46.5 |
| Sodium fluoride | 20 | 66.1 | 64.4 | 45.0 |
| | 40 | 65.8 | 64.6 | 46.8 |
| Hydrogen peroxide | 100 | 64.7 | 63.5 | N.D. |
| | 500 | 62.3 | 60.8 | N.D. |
| Mannitol | 250 | 66.2 | 65.2 | 48.1 |
| | 550 | 67.5 | 66.4 | 49.7 |

TABLE 5

Mid-point of the thermal unfolding transition midpoint (Tm) for fructanases derived from first derivative under various formulation ingredients concentrations at pH 6.0.

| Reagent | Concentration (mM) | Tm (° C.) at pH 6.0 SEQ ID NO: 2 | SEQ ID NO: 3 | SEQ ID NO: 4 |
|---|---|---|---|---|
| Control | 0 | 66.2 | 64.1 | 47.9 |
| Sodium benzoate | 10 | 66.1 | 64.3 | 47.5 |
| | 35 | 65.3 | 63.7 | 46.9 |
| Arginine | 30 | 59.8 | 62.0 | 46.7 |
| | 90 | 58.5 | 60.9 | 45.0 |
| EDTA | 1 | 66.5 | 64.6 | 47.9 |
| Ethanol | 1000 | 65.3 | 62.9 | 46.0 |
| Glycerol | 1000 | 67.8 | 65.8 | 48.7 |
| | 3250 | 70.7 | 68.4 | 51.2 |
| Sodium phosphate | 5 | 66.2 | 64.3 | 46.5 |
| | 10 | 65.8 | 64.0 | 45.4 |
| Sorbitol | 550 | 67.2 | 66.3 | 50.8 |
| | 2200 | 74.7 | 73.3 | 59.7 |
| Potassium Sorbate | 10 | 66.1 | 64.1 | 47.6 |
| | 35 | 66.2 | 63.8 | 46.5 |
| Sodium fluoride | 20 | 65.4 | 64.3 | 47.7 |
| | 40 | 64.9 | 64.2 | 47.8 |
| Hydrogen peroxide | 100 | 65.1 | 62.7 | N.D. |
| | 500 | 64.5 | 61.5 | N.D. |
| Mannitol | 250 | 67.3 | 65.3 | 48.8 |
| | 550 | 68.4 | 66.3 | 50.8 |

Example 4: Fructanase Activity Assays

Assay Descriptions

Fructanases were incubated with four different substrates:

1) Sucrose (1% w/v-CHE02134, 500 mg added to 50 mL MilliQ water)
2) Fructan (Megazyme K-FRUCHK, 3 mg dissolved in 25 mM Universal buffer, pH 6 (acetic acid, MES, HEPES and glycine) to a final volume of 300 μL)
3) Inulin (from chicory root; DP2-60 from Megazyme P-INUL, 0.1% w/v, 10 mg added to 10 mL MilliQ water)
4) Levan (Megazyme P-levan, 3 mg dissolved in 25 mM Universal buffer, pH 6 (acetic acid, MES, HEPES, and glycine) to a final volume of 300 μL)

Each sample was diluted 10× into 25 mM Universal buffer pH 6 (Acetic acid, MES, HEPES, and Glycine). Samples were added to a final concentration of 50 ppm (0.05 mg/mL). Samples containing fructanase and the respective substrates were incubated for 60 min at 37° C. at 1400 rpm, and samples without enzyme addition were used as substrate controls.

After incubation, samples were spun down for 5 min at 16100×G at room temperature. The supernatants were analyzed by 1) liquid chromatography and 2) reducing sugars assay, as follows:

1) Liquid chromatography was performed on a Dionex IC300 system with a PD10 column (ThermoFisher Scientific) using the following gradient:

| Time (min) | Flow (mL/min) | % Water | % NaOH 0.5M | % NaOAc 0.5M |
|---|---|---|---|---|
| 0 | 0.8 | 97 | 3 | 0 |
| 4.5 | 0.8 | 96 | 4 | 0 |
| 7 | 0.8 | 93 | 7 | 0 |
| 10 | 0.8 | 80 | 15 | 5 |
| 25 | 0.8 | 50 | 15 | 35 |
| 28.1 | 0.8 | 85 | 15 | 0 |
| 29 | 0.8 | 90 | 10 | 0 |
| 30.1 | 0.8 | 97 | 3 | 0 |
| 33 | 0.8 | 97 | 3 | 0 |
| 33.1 | 0 | — | — | — |

Fructose and glucose (Sigma) were used as standard references. Fructose release was measured by liquid chromatography as area in nano Coulombs per minute (nC*min). Here, the area is proportional to the fructose release.

2) For the reducing sugars assay, the working buffer was prepared by weighing 50 g of potassium sodium tartrate (K—Na-tartrate, Merck 8087) and 20 g of NaOH (Merck 1.06498) into 1 L of water.

For the reducing agent, also called PAHBAH reagent, a solution of PAHBAH (4-hydroxybenzoic hydrazide, Sigma H-9882) was prepared by weighing 225 mg PAHBAH into 15 ml of buffer.

The colorimetric reaction was made by transferring 75 µL of the respective sample supernatant to a PCR plate and adding 150 µL PAHBAH reagent. After incubation at 95° C. for 10 min in a PCR machine, 150 µL of each sample was transferred to a microtiter plate to read the absorbance at 405 nm (A405).

Results

The two different assays, liquid chromatography and colorimetric reducing ends, showed that the evaluated fructanases can hydrolyze fructan with a high level of activity. These fructanases can degrade at least two of the four substrates tested, including at least two out of fructan, levan, and inulin. The fructanases are able to produce the monosaccharide fructose, indicating an exo-acting mechanism.

| | Fructan | | Levan | | Inulin | | Sucrose | |
|---|---|---|---|---|---|---|---|---|
| SEQ ID NO: | Fructose release (nC*min) | Reducing sugars (A405) | Fructose release (nC*min) | Reducing sugars (A405) | Fructose release (nC*min) | Reducing sugars (A405) | Fructose release (nC*min) | Reducing sugars (A405) |
| 1 | 1399 | 2.700 | 1767 | 2.372 | 1845 | 3.095 | 467 | 2.544 |
| 2 | 644 | 2.397 | 204 | 2.789 | 237 | 0.437 | 916 | 1.00 |
| 3 | 745 | 2.489 | 211 | 3.063 | 237 | 0.433 | 818 | 1.106 |
| 4 | 611 | 1.107 | 1498 | 1.920 | 4 | 0.754 | 57 | 1.159 |
| 5 | 723 | 2.460 | 416 | 2.965 | 240 | 0.427 | 729 | 1.121 |
| 6 | 644 | 1.756 | 145 | 3.225 | 238 | 0.443 | 750 | 0.71 |
| 7 | 708 | 2.342 | 161 | 2.890 | 241 | 0.435 | 1129 | 0.919 |
| Control | 38 | 0.221 | 27 | 0.698 | 10 | 0.101 | 58 | 0.065 |

Example 5: Single- and Multi-Species Biofilm Prevention Assays

A subset of fructanases was further evaluated for their ability prevent formation of oral biofilm. The preventive effect on biofilm formation was evaluated for three different biofilms grown in 96-well microtiter plates. Two biofilms were single-species biofilms of *Streptococcus mutans* UA159 and *Streptococcus downei* DSM5635, respectively, and one was a mixed-species biofilm consisting of the three dental pathogens *S. mutans* UA159, *Actinomyces naeslundii* ATCC 12104, and *Streptococcus oralis* ATCC 35037 (H. Koo et al., Journal of Bacteriology 2010; K. B. Ahn et al., PLoS ONE, 2018; H. M. Nassar and R. L. Gregory, Journal of Oral Microbiology, 2017).

96-well microtiter plates (Nunclon Delta surface, ThermoScientific #167008) were filled with 75 μl of Tripticase Soy Broth (TSB)+1% sucrose containing 1×107 CFU/ml bacterial inoculum of either *S. mutans* UA159, *S. downei* DSM5635, or a mix of *S. mutans* UA159, *A. naeslundii* ATCC 12104, and *S. oralis* ATCC 35037. For fructanase treatment samples, 25 μl of enzyme solution in buffer (50 mM HEPES, 100 mM NaCl, pH 7) was added to yield a final concentration of 80 ppm. For control treatment samples, the enzyme solution was replaced with buffer (50 mM HEPES, 100 mM NaCl, pH 7).

Plates were incubated at 37° C. for 21 hours without shaking in a ThermoFisher Scientific Rectangular AnaeroBox™ container (2.5 L, #AN0025A) under anaerobic conditions. Enzyme and control samples were evaluated in eight replicates.

After incubation, planktonic bacteria were removed by two gentle washes with 100 μl 0.9% NaCl and biofilms were stained with 0.95% crystal violet solution for 15 min at room temperature. Plates were rinsed twice with 100 μL 0.9% NaCl and adhered dye was dissolved with a solution of 96% ethanol and 0.1% acetic acid in water. Absorbance was measured at 600 nm with a microplate reader SpectraMax M3, Molecular Devices.

For the data processing, the absorbance was taken to be proportional to the extent of remaining biofilm after enzyme or buffer treatment. The results were expressed as percentage of biofilm prevention and was calculated as follows:

$$100-((A600\text{ nm enzyme treated sample})/(A600\text{ nm buffer control treated sample})\times 100),$$

where A600 nm refers to the average of eight absorbances measured at 600 nm of either enzyme or buffer treated samples. Results are listed in Tables 6-8 below:

TABLE 6

Single-species *S. downei* biofilm prevention assay

| Treatment | Average A600 | STD Dev | Biofilm prevention (%) |
|---|---|---|---|
| Control | 0.37 | 0.01 | 0 |
| SEQ ID NO: 1 | 0.14 | 0.02 | 61.6 |
| SEQ ID NO: 2 | 0.11 | 0.01 | 70.6 |

TABLE 7

Single-species *S. mutans* biofilm prevention assay

| Treatment | Average A600 | STD Dev | Biofilm prevention (%) |
|---|---|---|---|
| Control | 0.44 | 0.01 | 0 |
| SEQ ID NO: 1 | 0.21 | 0.02 | 52.3 |
| SEQ ID NO: 2 | 0.11 | 0.01 | 75.4 |

TABLE 8

Multi-species biofilm *S. mutans*, *S. oralis*, *A. naeslundii* prevention assay

| Treatment | Average A600 | STD Dev | Biofilm prevention (%) |
|---|---|---|---|
| Control | 0.41 | 0.02 | 0 |
| SEQ ID NO: 1 | 0.26 | 0.02 | 36.4 |
| SEQ ID NO: 2 | 0.14 | 0.01 | 65.1 |

As seen from Tables 6-8 above, the fructanases of SEQ ID NO: 1 and SEQ ID NO:2 have a preventive effect on formation of single-species biofilm (*S. mutans* and *S. downei*, respectively) as well as multi-species biofilm (*S. mutans, S. oralis*, and *A. naeslundii*) formed by known dental pathogens.

Example 6: Human Saliva Biofilm Prevention Assay

Fructanases were evaluated for their ability to prevent biofilm growth from human saliva. A biofilm prevention assay was carried out according to the method described in WO 2020/099490 with a few modifications. Briefly, the fructanase treatment samples were made by preparing an enzyme solution of 40 ppm in McIlvaine buffer, pH6 (prepared by mixing 12.63 ml 0.2 M $Na_2HPO_4$+7.37 ml 0.1 M citric acid), with control treatment samples consisting of McIlvaine buffer, pH6. Enzyme and control samples were evaluated in eight replicates.

For data processing, the absorbance was taken to be proportional to the extent of remaining biofilm after enzyme or buffer treatment. The percentage of biofilm prevention was calculated as follows:

$$100-((A600\text{ nm enzyme treated sample})/(A600\text{ nm buffer control treated sample})\times 100),$$

where A600 nm refers to the average of eight absorbance measurements performed at 600 nm using SpectraMax M3, Molecular Devices, of either enzyme or buffer treated samples. Results are listed in Table 9 below:

TABLE 9

Human saliva biofilm prevention assay

| Treatment | Average A600 | STD Dev | Biofilm prevention (%) |
|---|---|---|---|
| Experiment 1 | | | |
| Control | 0.817 | 0.037 | 0 |
| SEQ ID NO: 2 | 0.151 | 0.010 | 81.5 |
| SEQ ID NO: 3 | 0.152 | 0.015 | 81.2 |
| SEQ ID NO: 4 | 0.145 | 0.016 | 82.1 |
| SEQ ID NO: 5 | 0.148 | 0.012 | 81.8 |
| SEQ ID NO: 6 | 0.176 | 0.012 | 78.4 |

TABLE 9-continued

| Human saliva biofilm prevention assay | | | |
|---|---|---|---|
| Treatment | Average A600 | STD Dev | Biofilm prevention (%) |
| Experiment 2 | | | |
| Control | 0.766 | 0.074 | 0 |
| SEQ ID NO: 7 | 0.244 | 0.032 | 68.2 |

As seen from Table 9, fructanases are capable of preventing biofilm growth from human saliva.

Example 7: Human Saliva Biofilm Removal Assay

The fructanase of SEQ ID NO:2 was evaluated for its ability to remove biofilm grown from human saliva. A biofilm removal assay was carried out according to the method described in WO 2020/099490 with a few modifications. Briefly, the fructanase treatment samples were made by preparing an enzyme solution of 20 ppm in 50 mM HEPES, 100 mM NaCl, pH7, with control treatment samples consisting 50 mM HEPES, 100 mM, NaCl pH7. Enzyme and control samples were evaluated in four replicates.

For data processing, the absorbance was taken to be proportional to the extent of remaining biofilm after enzyme or buffer treatment. The percentage of biofilm removal was calculated as follows:

$$100-((A600\text{ nm enzyme treated sample})/(A600\text{ nm buffer control treated sample})\times 100),$$

where A600 nm refers to the average of four absorbances measured at 600 nm using SpectraMax M3, Molecular Devices, of either enzyme or buffer treated samples. Results are listed in Table 10 below:

TABLE 10

| Human saliva biofilm removal assay | | | |
|---|---|---|---|
| Treatment | Average A600 | STD dev | Biofilm removal (%) |
| Control | 0.41 | 0.06 | 0 |
| SEQ ID NO: 2 | 0.27 | 0.02 | 34.1 |

As seen from Table 10, fructanases (exemplified by SEQ ID NO:2) are capable of removing biofilm grown from human saliva.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An oral care composition comprising (a) a fructanase comprising the motif WMND (SEQ ID NO: 12); and (b) at least one oral care ingredient;

wherein the fructanase has at least two enzymatic activities selected from the group consisting of fructan-degrading activity, levan-degrading activity, inulin-degrading activity, and sucrose-degrading activity;

wherein the fructanase has a sequence identity of at least 95% to SEQ ID NO: 2; and wherein the composition is in the form of a toothpaste, dental cream, mouthwash, mouth rinse, lozenge, pastille, chewing gum, confectionary, candy, denture cleaning solution, denture cleaning tablet, or denture cleaning powder.

2. The oral care compositions according to claim 1, wherein the fructanase has at least two enzymatic activities selected from the group consisting of fructan-degrading activity, levan-degrading activity, and inulin-degrading activity.

3. The oral care composition according to claim 1, wherein the fructanase has at least two enzymatic activities selected from the group consisting of inulinase activity, 2,6-β-fructan 6-levanbiohydrolase activity, levanase activity, fructan β-fructosidase activity, fructan β-(2,1)-fructosidase activity, and fructan β-(2,6)-fructosidase activity, and wherein the fructanase degrades at least two polysaccharides selected from the group consisting of fructan, levan, and inulin.

4. The oral care composition according to claim 1, wherein the fructanase is a polypeptide comprising, consisting essentially of, or consisting of SEQ ID NO: 2.

5. The oral care composition according to claim 1, wherein the fructanase has on par or improved chemical stability in the presence of at least one oral care ingredient selected from the group consisting of benzoate, arginine, EDTA, ethanol, glycerol, phosphate, sorbitol, potassium sorbate, fluoride, hydrogen peroxide, and mannitol.

6. The oral care composition according to claim 1, which further comprises at least one other enzyme.

7. The oral care composition according to claim 6, wherein the at least one other enzyme is selected from the group consisting of DNase dispersin, protease, lipase, carbohydrase, dextranase, mutanase, oxidoreductase, laccase, peroxidase, oxidase, and lysozyme.

8. The oral care composition according to claim 6, wherein the at least one other enzyme is a DNase or a mutanase.

9. A method of treatment of a human or animal subject, the method comprising administering an oral care composition according to claim 1 to the human or animal subject.

10. The method of claim 9, wherein the oral care composition is administered to the oral cavity of said subject.

11. A method for removing oral biofilm, the method comprising contacting the oral biofilm with an oral care composition according to claim 1.

12. A kit of parts comprising:

a) an oral care composition according to claim 1; and b) instructions for use.

13. The oral care composition according to claim 1, wherein the at least one oral care ingredient is selected from abrasives, humectants, solvents, thickening agents, binding agents, buffering agents, foaming agents, foaming modulators, sweetening agents, softening agents, plasticizing agents, flavoring agents, coloring agents, therapeutic agents, anti-microbial agents, tartar-controlling agents, fluoride sources, preservatives, detergents, surfactants, coloring agents, buffering agents, softeners, plasticizers, whitening agents, bleaching agents, gum-base ingredients, and bulking agents.

14. The oral care composition according to claim 1, wherein the at least one oral care ingredient is selected from sodium fluoride, calcium fluoride, stannous fluoride, and sodium monofluorophosphate.

15. The oral care composition according to claim 1, wherein the fructanase has a sequence identity of at least 96% to SEQ ID NO: 2.

16. The oral care composition according to claim 1, wherein the fructanase has a sequence identity of at least 97% to SEQ ID NO: 2.

17. The oral care composition according to claim 1, wherein the fructanase has a sequence identity of at least 98% to SEQ ID NO: 2.

18. The oral care composition according to claim 1, wherein the fructanase has a sequence identity of at least 99% to SEQ ID NO: 2.

* * * * *